US008841436B2

(12) United States Patent
Gorodeski et al.

(10) Patent No.: US 8,841,436 B2
(45) Date of Patent: Sep. 23, 2014

(54) SCREENING, DIAGNOSING, TREATING AND PROGNOSIS OF PATHOPHYSIOLOGIC STATUS BY RNA REGULATION

(75) Inventors: George Gorodeski, Beachwood, OH (US); Judith Potashkin, Gurnee, IL (US); Bentley Cheatham, Durham, NC (US)

(73) Assignees: University Hospitals Cleveland Medical Center, Cleveland, OH (US); Rosalind Franklin University of Medicine and Science, an Illinois Corporation, North Chicago, IL (US)

( * ) Notice: Subject to any disclaimer, the term of this patent is extended or adjusted under 35 U.S.C. 154(b) by 54 days.

(21) Appl. No.: 12/450,124

(22) PCT Filed: Mar. 13, 2008

(86) PCT No.: PCT/US2008/003298
§ 371 (c)(1),
(2), (4) Date: Apr. 14, 2010

(87) PCT Pub. No.: WO2008/115387
PCT Pub. Date: Sep. 25, 2008

(65) Prior Publication Data
US 2010/0196886 A1    Aug. 5, 2010

Related U.S. Application Data

(60) Provisional application No. 60/918,242, filed on Mar. 15, 2007.

(51) Int. Cl.
C07H 21/04        (2006.01)
C12N 15/113       (2010.01)
C12Q 1/68         (2006.01)

(52) U.S. Cl.
CPC ........ *C12N 15/1138* (2013.01); *C12N 2320/11* (2013.01); *C12Q 2600/106* (2013.01); *C12Q 1/6809* (2013.01); *C12N 2310/14* (2013.01); *C12Q 2600/178* (2013.01); *C12N 2330/10* (2013.01); *C12Q 2600/118* (2013.01); *C12Q 1/6886* (2013.01)
USPC .......... 536/24.5; 536/24.31; 536/24.1; 435/6; 435/325; 435/375

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. | 424/450 |
| 4,501,728 A | 2/1985 | Geho et al. | 424/450 |
| 4,837,028 A | 6/1989 | Allen | 424/1.21 |
| 4,987,071 A | 1/1991 | Cech et al. | 435/91.31 |
| 5,019,369 A | 5/1991 | Presant et al. | 424/1.21 |
| 5,139,941 A | 8/1992 | Muzyczka et al. | 435/456 |
| 5,252,479 A | 10/1993 | Srivastava | 435/235.1 |
| 5,427,916 A | 6/1995 | Gewirtz et al. | 435/5 |
| 5,849,902 A | 12/1998 | Arrow et al. | 536/24.5 |
| 2002/0086356 A1 | 7/2002 | Tuschl et al. | 435/69.1 |
| 2002/0173478 A1 | 11/2002 | Gewirtz | 514/44 A |
| 2004/0014113 A1 | 1/2004 | Yang et al. | 435/6.11 |
| 2004/0018176 A1 | 1/2004 | Tolentino et al. | 424/93.21 |
| 2005/0022725 A1 | 2/2005 | Jurgensen et al. | 117/104 |
| 2005/0153918 A1 | 7/2005 | Chabot et al. | 514/44 A |
| 2006/0105360 A1 | 5/2006 | Croce et al. | 435/6.18 |
| 2006/0292616 A1 | 12/2006 | Neely et al. | 435/6.12 |
| 2007/0026403 A1 | 2/2007 | Hatzigeorgiou et al. | 435/6.11 |
| 2008/0171715 A1* | 7/2008 | Brown et al. | 514/44 |

FOREIGN PATENT DOCUMENTS

| | | |
|---|---|---|
| WO | WO 93/24641 | 12/1993 |
| WO | WO 94/13788 | 6/1994 |
| WO | WO 2005078139 A2 | 8/2005 |
| WO | WO 2005118806 A2 | 12/2005 |
| WO | WO 2005118806 A2 | 2/2006 |
| WO | WO 2005118806 A | 6/2006 |
| WO | WO 2005118806 B | 7/2006 |

OTHER PUBLICATIONS

Kong et al. P2X7 nucleotide receptors mediate caspase-8/9/3-dependent apoptosis in rat primary cortical neurons. Purinergic Signaling 2005, 1:337-347.*

Lagos-Quintana et al. New microRNAs from mouse and human. RNA 2003, 9: 175-179.*

Ambros, "miRNAs: tiny regulators with great potential" *Cell*, 107:823-826 (2001).

Ambros, "The functions of animal microRNAs." *Nature*, 431:350-355 (2004).

Anderson, "Human gene therapy." *Nature*, Supplement, 392:25-30 (1998).

Bartel, et al., "MicroRNAs: At the Root of Plant Development?" *Plant Physiol.*, 132:709-717 (2003).

(Continued)

*Primary Examiner* — Kimberly Chong
(74) *Attorney, Agent, or Firm* — Medlen & Carroll, LLP

(57) ABSTRACT

A relationship between cancer and ribonucleic acid (RNA) regulation is described by determining intracellular levels of niRNA regulators. Generally, mRNA levels are decreased in cancer cells that may be a reflection of either reduced mRNA expression and/or increased mRNA degradation. miRNAs are identified that hybridize to an mRNA that are suspected to mediate intracellular mRNA steady state levels. Alternatively, ribonucleic acid binding protein (RBP) levels may also mediate intracellular mRNA steady state levels. In particular, this invention demonstrates an effective clinical management strategy for uterine cell cancers may be implemented by taking advantage of an exemplary relationship between $P2X_7$ mRNA and miRNAs including, but not limited to, miR-186 and/or miR-150.

9 Claims, 18 Drawing Sheets

(56) References Cited

OTHER PUBLICATIONS

Bartel, et al., "MicroRNAs: genomics, biogenesis, mechanism, and function." *Cell*, 116:281-297 (2004).
Brummelkamp, et al., "A System for Stable Expression of Short Interfering RNAs in Mammalian Cells." *Science*, 296:550-553 (2002).
Brummelkamp, et al., "A System for Stable Expression of Short Interfering RNAs in Mammalian Cells." Supplemental Data. *Science*, 296:550-553 (2002).
Brummelkamp, et al., "A System for Stable Expression of Short Interfering RNAs in Mammalian Cells." Supplemental Data Figure. *Science*, 296:550-553 (2002).
Buell, et al., "Gene structure and chromosomal localization of the human P2X7 receptor." *Receptors Channels* 5:347-354 (1998).
Burd, et al., "Conserved structures and diversity of functions of RNA-binding proteins." *Science*, 265:615-621 (1994).
Calin, et al., "Frequent deletions and down-regulation of miRNA genes miR-15 and miR-16 at 13q14 in chronic lymphocytic leukemia." *Proc. Natl Acad. Sci. USA*, 99:15524-15529 (2002).
Chen, et al., "MicroRNAs Modulate Hematopoietic Lineage Differentiation." *Science*, 303:83-86 (2004).
Chen, et al., "MicroRNAs Modulate Hematopoietic Lineage Differentiation." *Science*, 303:83-86 Supplemental Online Material Revised (2004).
Cheng, et al., "Antisense inhibition of human mRNAs and indications for an involvement of miRNA in cell growth and apoptosis." *Nucleic Acids Research*, 33:1290-1297 (2005).
Colas, et al., "Genetic selection of peptide aptamers that recognize and inhibit cyclin-dependent kinase 2." *Nature*, 380:548-550 (1996).
Corpet, "Multiple sequence alignment with hierarchical clustering." *Nucleic Acids Research*, 16:10881-90 (1988).
Couzin, "Breakthrough of the Year. Small RNAs Make Big Splash." *Science*, 298:2296-2297 (2002).
Croce, et al., "miRNAs, cancer, and stem cell division." *Cell*, 122:6-7 (2005).
Dennis, "Small RNAs: The genome's guiding hand?" Nature, 420:732 (2002).
Doench, et al., "siRNAs can function as miRNAs." *Genes Dev.*, 17:438-442 (2003).
Doench, et al., "Specificity of microRNA target selection in translational repression." *Genes, Dev.* 18:504-511 (2004).
Dornburg, "Reticuloendotheliosis viruses and derived vectors." *Gene Therap.*, 2:301-310 (1995).
Eglitis, et al., "Retroviral Vectors for Introduction of Genes into Mammalian Cells." *Biotechniques*, 6(7):608-614 (1988).
Elbashir, et al., "RNA interference is mediated by 21- and 22-nucleotide RNAs." *Genes Dev.*, 15:188-200 (2001).
Fienberg, et al.,"A technique for radiolabeling DNA restriction endonuclease fragments to high specific activity." *Anal. Biochem.*, 132:6-13 (1983).
Fienberg, et al., "A technique for radiolabeling DNA restriction endonuclease fragments to high specific activity." Addendum. *Anal. Biochem.*, 137(1):266-7 (1983).
Feng, et al., "ATP ligation stimulates GRK-3-mediated phosphorylation and β-arrestin-2- and dynamin-dependent internalization of the $P2X_7$-receptor." *Am J Physiol.*, 288:C1342-C1356 (2005).
Feng, et al., "A truncated $P2X_7$ receptor variant ($P2X_{7-j}$) endogenously expressed in cervical cancer cells antagonizes the full-length $P2X_7$ receptor through hetero-oligomerizaton." *J. Biol. Chem.*, 281:17228-17237 (2006).
Ferrandon, et al., "Staufen protein associates with the 3'UTR of bicoid mRNA to form particles that move in a microtubule-dependent manner." *Cell*, 79:1221-1232 (1994).
Fisher, et al., "Transduction with recombinant adeno-associated virus for gene therapy is limited by leading-strand synthesis." *J. Virol.*, 70:520-532 (1996).
Gabizon, et al., "Liposome formulations with prolonged circulation time in blood and enhanced uptake by tumors." *Proc. Natl. Acad. Sci., USA*, 18:6949-6953 (1988).

Gerlach, et al., "Multidrug resistance." *Cancer Surveys*, 5:25-46 (1986).
Goldie and Coldman, "The Genetic Origin of Drug Resistance in Neoplasms: Implications for Systemic Therapy." *Cancer Research*, 44:3643-3653 (1984).
Gorodeski, et al., "Retinoids, sex steroids, and glucocorticoids regulate ectocervical cell envelope formation but not the level of the envelope precursor, involucrin." *Differentiation*, 42:75-80 (1989).
Gorodeski, et al., "Characterization of paracellular permeability in cultured human cervical epithelium: regulation by extracellular ATP." *J Soc Gynecol Investig.*, 1:225-233 (1994a).
Gorodeski, et al., "Human uterine cervical epithelial cells grown on permeable support-a new model for the study of differentiation and transepithelial transport." *Differentiation*, 56:107-118 (1994b).
Guhaniyogi, et al., "Regulation of mRNA stability in mammalian cells." *Gene*, 265:11-23 (2001).
Hammann, et al., "Length variation of helix III in a hammerhead ribozyme and its influence on cleavage activity." *Antisense and Nucleic Acid Drug Dev.*, 9:25-31 (1999).
Hentze, "Translational regulation: versatile mechanisms for metabolic and developmental control." *Curr. Op. Biol.*, 7:393-398 (1995).
Higgins, et al., "CLUSTAL: a package for performing multiple sequence alignment on a microcomputer." *Gene*, 73:237-244 (1988).
Huang, et al., "Dynamic programming algorithms for restriction map comparison." *Computer Applications in the Biosciences*, 8:1-6 (1992).
Hutvagner, et al., "A microRNA in a multiple-turnover RNAi enzyme complex" *Science*, 297:2056-2060 (2002).
James, "Nucleic acid and polypeptide aptamers: a powerful approach to ligand discovery." *Current Opinion in Pharmacology*, 1:540-546 (2001).
Kidner, et al., "Macro effects of microRNAs in plants." *Trends Genet.*, 19:13-16 (2003).
Kohler, et al., "Continuous cultures of fused cells secreting antibody of predefined specificity." *Nature*, 256:495-497 (1975).
Kozbor, et al., "The Production of Monoclonal Antibodies From Human Lymphocytes." *Immunology Today*, 4:72 (1983).
Lee, et al., "The *C. elegans* heterochronic gene lin-4 encodes small RNAs with antisense complementarity to lin-14." *Cell*, 75:843-854 (1993).
Lee, et al., "Expression of small interfering RNAs targeted against HIV-1 rev transcripts in human cells." *Nat. Biotechnol.*, 20:500-505 (2002).
Lewis, et al., "Prediction of mammalian miRNA targets." *Cell*, 115:787-798 (2003).
Lewis, et al., "Conserved seed pairing, often flanked by adenosines, indicates that thousands of human genes are microRNA targets." *Cell*, 120:15-20 (2005).
Li, et al., "The $P2X_7$ Receptor: A novel biomarker of uterine epithelial cancers." *Cancer Epidemiology Biomarkers and Prevention*, 15:1-8 (2006a).
Li, et al., "The $P2X_7$ receptor: A novel biomarker of uterine epithelial cancers." *Cancer Epidemiology Biomarkers and Prevention*, 15:1906-1913 (2006b).
Llave, et al., "Cleavage of Scarecrow-like mRNA targets directed by a class of *Arabidopsis* miRNA." *Science*, 297:2053-2056 (2002).
Llave, et al., "Cleavage of Scarecrow-like mRNA targets directed by a class of *Arabidopsis* miRNA." Supporting Online Material. *Science*, 297:2053-2056 (2002).
Metzler, et al., "High expression of precursor miRNA-155/BIC RNA in children with Burkitt lymphoma." *Genes Chromosomes Cancer*, 2:167-169 (2004).
Michael, et al., "Reduced accumulation of specific miRNAs in colorectal neoplasia." *Mol. Cancer Res.*, 1:882-891 (2003).
Miller, "Retrovirus packaging cells." *Hum. Gene Therap.*, 1:5-14 (1990).
Mitchell, et al., "mRNA turnover." *Curr Opin Biol.*, 13:320-325 (2001).
Miyagishi, et al., "U6 promoter-driven siRNAs with four uridine 3' overhangs efficiently suppress targeted gene expression in mammalian cells." *Nat. Biotechnol.*, 20:497-500 (2002).

(56) References Cited

OTHER PUBLICATIONS

Moss, et al., "The cold shock domain protein LIN-28 controls developmental timing in *C. elegans* and is regulated by the lin-4 RNA." *Cell*, 88:637-646 (1997).
Needleman, et al., "A general method applicable to the search for similarities in the amino acid sequence of two proteins." *Mol. Biol.*, 48: 443 (1970).
Olsen, et al., "The lin-4 regulatory RNA controls developmental timing in *Caenorhabditis elegans* by blocking LIN-14 protein synthesis after the initiation of translation." *Dev Biol*, 216:671-680 (1999).
Paddison, et al., "Stable suppression of gene expression by RNAi in mammalian cells." *Genes, Dev.* 16:948-958 (2002).
Paul, et al., "Effective expression of small interfering RNA in human cells." *Nat. Biotechnol.*, 20:505-508 (2002).
Pearson, et al., "Improved tools for biological sequence comparison." *Proc. Natl. Acad. Sci, USA*, 8:2444 (1988).
Pearson, et al., "Using the FASTA Program to Search Protein and DNA Sequence Databases." Chapter 26 in *Methods in Molecular Biology*. 24:7-331 (1994).
Rabinowitz, et al., "Cross-Packaging of a Single Adeno-Associated Virus (AAV) Type 2 Vector Genome into Multiple AAV Serotypes Enables Transduction with Broad Specificity." *J Virol.*, 76:791-801 (2002).
Ralevic, et al., "Receptors for purines and pyrimidines." *Pharmacol Rev* 50:413-492 (1998).
Reinhart, et al., "The 21-nucleotide let-7 RNA regulates developmental timing in *Caenorhabditis elegans*." *Nature* 403:901-906 (2000).
Rhoades, et al., "Prediction of plant microRNA targets." *Cell*, 110:513-520 (2002).
Rigby, et al., "Labeling Deoxyribonucleic Acid to High Specific Activity in Vitro by Nick Translation With DNA Polymerase I." *J. Mol. Biol.*, 113:237-251 (1977).
Samulski, et al., "A recombinant plasmid from which an infectious adeno-associated virus genome can be excised in vitro and its use to study viral replication." *J. Virol.*, 61:3096-3101 (1987).
Samulski, et al., "Helper-free stocks of recombinant adeno-associated viruses: normal integration does not require viral gene expression." *J. Virol.*, 63:3822-3826 (1989).
Seggerson, et al., "Two genetic circuits repress the *Caenorhabditis elegans* heterochronic gene lin-28 after translation initiation." *Dev Biol.*, 243:213-225 (2002).
Seitz, et al., "Imprinted microRNA genes transcribed antisense to a reciprocally imprinted retrotransposon-like gene." *Nat Genet.*, 34:261-262 (2003).
Smith, et al., "Comparison of biosequences." *Adv. Appl.* Math 2: 482 (1981).
Stein, et al., "Antisense oligonucleotides as therapeutic agents—is the bullet really magical?" *Science*, 261:1004 (1993).
Sugito et al., "RNASEN Regulates cell proliferation and affects survival in esophageal cancer patients." *Clin Cancer Res.*, 12:OF1-OF7 (2006).
Szoka, et al., "Comparative properties and methods of preparation of lipid vesicles (liposomes)." *Ann. Rev. Biophys. Bioeng.*, 9:467 (1980).
Tuschl, "Expanding small RNA interference." *Nat. Biotechno.*, 20:446-448 (2002).
Wang, et al., "$P2X_7$-receptor mediated apoptosis of human cervical epithelial cells." *Am J. Physiol.*, 287:C1349-C1358 (2004a).
Wang, et al., "Anti-apototic effects of estrogen in normal and in cancer human cervical epithelial cells." *Endocrinology*, 145:5568-5579 (2004b).
Wang, et al., "Epidermal Growth Factor facilitates epinephrine inhibition of $P2X_7$-receptor mediated pore formation and apoptosis: a novel signaling network." *Endocrinology*,146:164-174 (2005).
Wang, et al., "MicroRNA: past and present." *Front Biosci.*, 12:2316-2329 (2007).
Werner, et al., "The effect of base mismatches in the substrate recognition helices of hammerhead ribozymes on binding and catalysis." *Nucl. Acids Res.*, 23:2092-96 (1995).
Wienholds, et al., "MiRNA function in animal development." *FEBS Lett.*, 579:5911-5922 (2005).
Wightman, et al., "Posttranscriptional regulation of the heterochronic gene lin-14 by lin-4 mediates temporal pattern formation in C. elegan." *Cell*, 75:855-862 (1993).
Xia, et al., "siRNA-mediated gene silencing in vitro and in vivo." *Nat. Biotech.* 20:1006-1010 (2002).
Yi, et al., "Exportin-5 mediates the nuclear export of pre-microRNAs and short hairpin RNAs." *Genes Dev.*, 17:3011-3016 (2003).
Zeng, et al., "Both natural and designed micro RNAs can inhibit the expression of cognate mRNAs when expressed in human cells." *Mol Cell*, 9:1327-1333 (2002).
Zeng, et al., "Sequence requirements for micro RNA processing and function in human cells." *RNA*, 9:112-123 (2003).
Zeng, et al., "Estrogen abrogates transcervical tight junctional resistance by acceleration of occludin modulation." *J Clin Endocrinol Metab.*, 89:5145-5155 (2004).
Zhu, et al., "Changes in tight junctional resistance of the cervical epithelium are associated with modulation of content and phosphorylation of occludin 65-kilodalton and 50-kilodalton forms." *Endocrinology*, 147:977-989 (2006).
Dostie, et al., "Numerous microRNPs in neuronal cells containing novel microRNAs." *RNA*, 9(2):180-186 (2003).
Martin, et al., "miRNA expression signatures in cervical cancer." XP008123519, *Laboratory Investigation*, vol. 86, Suppl. p. 189A, 95th Annual Meeting of the United-States-And-Canadian-Academy-Of-Pathology; Atlanta, GA, USA, (2006a).
Martin, et al., "Molecular profiling of cervical neoplasia." *Expert Review of Molecular Diagnostics*, Expert Reviews Ltd, 6(2):217-229 (2006b).
Monticelli, et al., "MicroRNA profiling of the murine hematopoietic system." *Genome Biology*, 20053, 6(8):R71.1-R71.15 (2005); and.
Zhou, et al., "MicroRNAs miR-186 and miR-150 down-regulate expression of the pro-apoptotic purinergic P2X(7) receptor by activation of instability sites at the 3'-untranslated region of the gene that decrease steady-state levels of the transcript." *Journal of Biological Chemistry*, 283(42):28274-28286 (2008).

\* cited by examiner

SEQUENCE LISTING

```
<160> NUMBER OF SEQ ID NOS: 25

<210> SEQ ID NO 1
<211> LENGTH: 64
<212> TYPE: DNA
<213> ORGANISM: Artificial Sequence
<220> FEATURE:
<223> OTHER INFORMATION: Synthetic

<400> SEQUENCE: 1
ccctgtctcc caaccttgt accagtgctg ggctcagacc ctggtacagg cctgggggac    60
aggg                                                              64

<210> SEQ ID NO 2
<211> LENGTH: 86
<212> TYPE: DNA
```

<213> ORGANISM: Artificial Sequence
<220> FEATURE:
<223> OTHER INFORMATION: Synthetic

<400> SEQUENCE: 2
tgcttgtaac tttccaaaga attctccttt tgggctttct ggtttattt taagcccaaa    60 ggtgaatttt ttgggaagtt tgagct    86

<210> SEQ ID NO 3
<211> LENGTH: 71
<212> TYPE: DNA
<213> ORGANISM: Artificial Sequence
<220> FEATURE:
<223> OTHER INFORMATION: Synthetic

<400> SEQUENCE: 3
actttccaaa gaattctcct tttgggcttt ctggttttat tttaagccca aaggtgaatt    60
ttttgggaag t    71

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7
<211> LENGTH: 48
<212> TYPE: DNA
<213> ORGANISM: Artificial Sequence
<220> FEATURE:
<223> OTHER INFORMATION: Synthetic

<400> SEQUENCE: 7
ccttgtaccc tggctacaac ttcagatacg ccaagtacta caaggaaa    48

<210> SEQ ID NO 8
<211> LENGTH: 43
<212> TYPE: DNA
<213> ORGANISM: Artificial Sequence
<220> FEATURE:
<223> OTHER INFORMATION: Synthetic

<400> SEQUENCE: 8
ttcagatgtg gcaattcaga tacgccaagt actacaaggg aaa    43

<210> SEQ ID NO 9
<211> LENGTH: 47
<212> TYPE: DNA
<213> ORGANISM: Artificial Sequence
<220> FEATURE:
<223> OTHER INFORMATION: Synthetic

<400> SEQUENCE: 9

```
tgtaatacga ctcactatag ggcaattcag ggcggaataa tgggcat                       47

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
agggtacaag gacacgttgg                                                     20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
caattcaggg cggaataatg                                                     20

<210> SEQ ID NO 12
<211> LENGTH: 47
<212> TYPE: DNA
<213> ORGANISM: Artificial Sequence
<220> FEATURE:
<223> OTHER INFORMATION: Synthetic

<400> SEQUENCE: 12
tgtaatacga ctcactatag ggtagccagg gtacaaggac acgttgg                       47

<210> SEQ ID NO 13
<211> LENGTH: 39
<212> TYPE: DNA
<213> ORGANISM: Artificial Sequence
<220> FEATURE:
<223> OTHER INFORMATION: Synthetic

<400> SEQUENCE: 13 tttttctag aagccaggca ccgtggctca cgtctgtaa                                 39

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
agccaggatg aaaagggttt                                                     20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ctgtccccag gaagttgtgt                                                     20

<210> SEQ ID NO 16
<211> LENGTH: 54
<212> TYPE: DNA
<213> ORGANISM: Artificial Sequence
```

```
<220> FEATURE:
<223> OTHER INFORMATION: Synthetic

<400> SEQUENCE: 16 tttttttctag attttttttt tttttttgaga tggagtctcg ctctgtcacc cagc            54

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
tatgaagaga tacgccctgg tt                                                22

<210> SEQ ID NO 18
<211> LENGTH: 22
<212> TYPE: DNA
<213> ORGANISM: Artificial Sequence
<220> FEATURE:
<223> OTHER INFORMATION: Synthetic

<400> SEQUENCE: 18
cttcgatact ttgctatacc cg                                                22

<210> SEQ ID NO 19
<211> LENGTH: 1271
<212> TYPE: DNA
<213> ORGANISM: Homo sapiens

<400> SEQUENCE: 19
agccaggcac cgtggctcac gtctgtaatc ccagcgcttt gggaggccga ggcaggcaga         60
tcacctgagg tcgggagttg agacccgcc tggctaacaa ggcgaaatcc tgtctgtact        120
aaaaatacaa aaatcagcca gacatggtgg catgcacctg caatcccagc tactcgggag       180
gctgaggcac aagaatcact tgaacccggg aggcagaggt tgtagtgagc ccagattgtg       240
ccactgctct ccagcctggg aggcacagca aactgtcccc caaaaaaaaa aaagagtcct       300
taccaatagc aggggctgca gtagccatgt taacatgaca tttaccagca acttgaactt       360
cacctgcaaa gctctgtggc cacattttca gccaagggga aatatgcttt catcttctgt       420
tgctctctgt gtctgagagc aaagtgacct ggttaaacaa accagaatcc ctctacatgg       480
actcagagaa aagagattga gatgtaagtc tcaactctgt ccccaggaag ttgtgtgacc       540
ctaggcctct cacctctgtg cctctgtctc cttgttgccc aactactatc tcagagatat       600
tgtgaggaca aattgagaca gtgcacatga actgtctttt aatgtgtaaa gatctacatg       660
aatgcaaaac atttcattat gaggtcagac taggataatg tccaactaaa aacaaaccct       720
tttcatcctg gctggagaat gtggagaact aaaggtggcc acaaattctt tgacactcaa       780
gtcccccaag acctaagggt tttatctcct cccccttgaat atgggtggct ctgattgctt     840
tatccaaaag tggaagtgac attgtgtcag tttcagatcc tgatcttaag aggctgacag       900
cttctacttg ctgtcccttg gaactcttgc tatcggggaa gccagacgcc atttaaaagt       960
ctgcctatcc tggccaggtg tggtggctca cacctgtaat cccagcactt tgggagacca      1020
aggcgggcgg atcacttaaa gtcaggagtc caagaccaga ctcgccaaca tggtgaaacc      1080
gtatctctaa taaaaataca aaaattagct gggcatggtg cgggcacctg tagtcctagc      1140
tatcaagagg ctgagacagg agaaacactt gaacctggga ggtggaggtt gcattgagct      1200
```

```
gagatcgtgc cactgcactc caggctgggt gacagagcga gactccatct caaaaaaaaa      1260
aaaaagaaaa a                                                           1271
```

<210> SEQ ID NO 20
<211> LENGTH: 23
<212> TYPE: DNA
<213> ORGANISM: Artificial Sequence
<220> FEATURE:
<223> OTHER INFORMATION: Synthetic

<400> SEQUENCE: 20

```
caaagaattc tcctttttggg ctt                                             23
```

<210> SEQ ID NO 21
<211> LENGTH: 22
<212> TYPE: DNA
<213> ORGANISM: Artificial Sequence
<220> FEATURE:
<223> OTHER INFORMATION: Synthetic

<400> SEQUENCE: 21

```
tctcccaacc cttgtaccag tg                                               22
```

<210> SEQ ID NO 22
<211> LENGTH: 34
<212> TYPE: DNA
<213> ORGANISM: Artificial Sequence
<220> FEATURE:
<223> OTHER INFORMATION: Synthetic

<400> SEQUENCE: 22

```
gagaactaaa ggtggccaca aattctttga cact                                  34
```

<210> SEQ ID NO 23
<211> LENGTH: 34
<212> TYPE: DNA
<213> ORGANISM: Artificial Sequence
<220> FEATURE:
<223> OTHER INFORMATION: Synthetic

<400> SEQUENCE: 23

```
gagaactaaa ggtggccaca aatagattga cact                                  34
```

<210> SEQ ID NO 24
<211> LENGTH: 27
<212> TYPE: DNA
<213> ORGANISM: Artificial Sequence
<220> FEATURE:
<223> OTHER INFORMATION: Synthetic

<400> SEQUENCE: 24

```
cacctgtaat cccagcactt tgggaga                                          27
```

<210> SEQ ID NO 25
<211> LENGTH: 27
<212> TYPE: DNA
<213> ORGANISM: Artificial Sequence
<220> FEATURE:
<223> OTHER INFORMATION: Synthetic

<400> SEQUENCE: 25

```
cacctgtaat cccagcactt tcccaga                                          27
```

SCREENING, DIAGNOSING, TREATING AND PROGNOSIS OF PATHOPHYSIOLOGIC STATUS BY RNA REGULATION

STATEMENT OF GOVERNMENT INTEREST

This invention was made with government support awarded by the National Institutes of Health (grant number NIH AG 15955). The government has certain rights in the invention.

FIELD OF INVENTION

The present invention is related to the field of ribonucleic acid (RNA) regulation of pathophysiological states. In one embodiment, microRNAs (miRNAs) are involved in regulating pathophysiological conditions. In another embodiment, RNA Binding Proteins (RPBs) are involved in regulating pathophysiological conditions. In particular, RNAs may be used to screen, diagnose, treat, and/or provide prognoses for pathophysiologic conditions in either animals or plants. In one embodiment, an miRNA capable of hybridizing with a $P2X_7$ gene is selected from the group consisting of miR-150 and/or miR-186 and may be used to screen, diagnose, treat, and/or provide prognoses for uterine cancer.

BACKGROUND

The term "chemotherapy" simply means the treatment of disease with chemical substances. The father of chemotherapy, Paul Ehrlich, imagined the perfect chemotherapeutic as a "magic bullet;" such a compound would kill invading organisms without harming the host. This target specificity is sought in all types of chemotherapeutics, including anticancer agents.

However, specificity has been the major problem with anticancer agents. In the case of anticancer agents, the drug needs to distinguish between host cells that are cancerous and host cells that are not cancerous. The vast bulk of anticancer drugs are indiscriminate at this level. Typically anticancer agents have negative hematological effects (e.g., cessation of mitosis and disintegration of formed elements in marrow and lymphoid tissues), and immunosuppressive action (e.g., depressed cell counts); as well as a severe impact on epithelial tissues (e.g., intestinal mucosa), reproductive tissues (e.g., impairment of spermatogenesis), and the nervous system. P. Calabresi and B. A. Chabner, In: Goodman and Gilman The Pharmacological Basis of Therapeutics (Pergamon Press, 10th Edition) (pp. 1381-1388).

Success with chemotherapeutics as anticancer agents has also been hampered by the phenomenon of multiple drug resistance, resistance to a wide range of structurally unrelated cytotoxic anticancer compounds. J. H. Gerlach et al., Cancer Surveys, 5:25-46 (1986). The underlying cause of progressive drug resistance may be due to a small population of drug-resistant cells within the tumor (e.g., mutant cells) at the time of diagnosis. J. H. Goldie and Andrew J. Coldman, Cancer Research, 44:3643-3653 (1984). Treating such a tumor with a single drug first results in a remission, where the tumor shrinks in size as a result of the killing of the predominant drug-sensitive cells. With the drug-sensitive cells gone, the remaining drug-resistant cells continue to multiply and eventually dominate the cell population of the tumor.

What is needed are compositions and methods to specifically identify biochemically altered cancer cells and correct this biochemical alteration.

SUMMARY OF THE INVENTION

The present invention is related to the field of ribonucleic acid (RNA) regulation of pathophysiological states. In one embodiment, microRNAs (miRNAs) are involved in regulating pathophysiological conditions. In another embodiment, RNA Binding Proteins (RPBs) are involved in regulating pathophysiological conditions. In particular, RNAs may be used to screen, diagnose, treat, and/or provide prognoses for pathophysiologic conditions in either animals or plants. In one embodiment, an miRNA capable of hybridizing with a $P2X_7$ gene is selected from the group consisting of miR-150 and/or miR-186 and may be used to screen, diagnose, treat, and/or provide prognoses for uterine cancer.

In one embodiment, the present invention contemplates a composition comprising a pathophysiological biomarker, wherein at least a portion of the biomarker is capable of hybridizing to a portion of a $P2X_7$ mRNA. In one embodiment, the $P2X_7$ mRNA portion comprises a 3'UTR. In one embodiment, the biomarker is capable of hybridizing under stringent conditions. In one embodiment, the biomarker is derived from a normal cell. In one embodiment, the biomarker is derived from a cancer cell. In one embodiment, the cancer cell comprises a uterine cell. In one embodiment, the biomarker comprises a microRNA. In one embodiment, the biomarker comprises miR-186. In one embodiment, the biomarker comprises miR-150.

In one embodiment, the present invention contemplates a method, comprising:
a) providing; i) a first sample comprising uterine cells suspected to be cancer cells; ii) a second sample comprising normal cells derived from a non-cancerous tissue cell; b) determining intracellular levels of at least one miRNA in said uterine cells and in said normal cells. In one embodiment, the intracellular levels of said at least one miRNA in said uterine cells is higher than said intracellular levels in normal cells such that said uterine cells are deemed to be cancer cells. In one embodiment, the higher levels of said at least one miRNA is selected from the group consisting of miR-150 and miR-186. In one embodiment, the cancer cells and said normal cells are derived from a mammal. In one embodiment, the mammal comprises a human. In one embodiment, the mammal comprises a non-human.

In one embodiment, the present invention contemplates a method, comprising: a) providing; i) an organism in need of a diagnosis for uterine cancer; ii) a first sample derived from said organism, wherein said sample comprises suspected uterine cancer cells; iii) a second sample derived from a non-cancerous tissue cell; b) determining intracellular levels of at least one miRNA in said uterine cells and in said non-cancerous tissue cells; d) comparing said intracellular levels of said at least one miRNA between said uterine cells and said non-cancerous tissue cells under conditions such that a diagnosis for uterine cancer is obtained. In one embodiment, the comparing identifies that said at least one miRNA level is elevated in said uterine cancer cells versus said non-cancerous cells. In one embodiment, the elevated at least one miRNA is selected from the group consisting of miR-150 and miR-186. In one embodiment, the organism comprises an animal. In one embodiment, the animal comprises a mammal. In one embodiment, the mammal comprises a human. In one embodiment, the mammal comprises a non-human.

In one embodiment, the present invention contemplates a method, comprising:
a) providing; i) a first sample comprising uterine cells suspected to be cancer cells; ii) a second sample comprising normal cells derived from a non-cancerous tissue; b) determining intracellular levels of at least one ribonucleic acid binding protein in said uterine cells and in said normal cells. In one embodiment, the intracellular levels of said at least one ribonucleic acid binding protein is higher than said intracellular levels in said normal cells such that said uterine cells are deemed to be cancer cells. In one embodiment, the higher levels of said at least ribonucleic acid binding protein is selected from the group consisting of those proteins described in Table 2. In one embodiment, the cancer cells and said normal cells are derived from a mammal. In one embodiment, the mammal comprises a human. In one embodiment, the mammal comprises a non-human.

In one embodiment, the present invention contemplates a method, comprising:
a) providing; i) an organism in need of a diagnosis for uterine cancer; ii) a first sample derived from said organism, wherein said sample comprises suspected uterine cancer cells; iii) a second sample derived from a non-cancerous tissue cell; b) determining intracellular levels of at least one ribonucleic acid binding protein in said uterine cells and in said non-cancerous tissue cells; d) comparing said intracellular levels of said at least one ribonucleic acid binding protein between said uterine cells and said non-cancerous tissue cells under conditions such that a diagnosis for uterine cancer is obtained. In one embodiment, the comparing identifies that said at least one ribonucleic acid binding protein level is elevated in said uterine cancer cells versus said non-cancerous cells. In one embodiment, the elevated at least ribonucleic acid binding protein is selected from the group consisting of those proteins described in Table 2. In one embodiment, the organism comprises an animal. In one embodiment, the animal comprises a mammal. In one embodiment, the mammal comprises a human. In one embodiment, the mammal comprises a non-human.

In one embodiment, the present invention contemplates a method comprising detecting a miRNA biomarker capable of hybridizing to a mRNA, thereby creating a biomarker binding pair. In one embodiment, the mRNA comprises a $P2X_7$ mRNA. In one embodiment, the miRNA biomarker comprises miR-150. In one embodiment, the miRNA biomarker comprises miR-186. In one embodiment, the mRNA comprises a 3'-UTR, wherein said 3'-UTR comprises at least one miRNA hybridization site. In one embodiment, the binding pair modulates mRNA degradation. In one embodiment, the binding pair modulates mRNA transcription. In one embodiment, the mRNA is derived from a tissue. In one embodiment, the tissue comprises a cancer cell. In one embodiment, the cancer cell comprises an epithelial cancer cell. In one embodiment, the tissue comprises a nerve cell. In one embodiment, the tissue comprises a neuroendocrine cell. In one embodiment, the tissue comprises an embryonic cell.

In one embodiment, the present invention contemplates a method of screening for pathophysiological conditions. In one embodiment, the method of screening comprises detecting an miRNA. In one embodiment, the miRNA is selected from the group comprising miR-150 and/or miR-186. In one embodiment, the detected miRNA levels is elevated when compared to normal levels, thereby suggesting the presence of the pathophysiological condition. In one embodiment, the detected miRNA levels is reduced when compared to normal levels. In one embodiment, the method of screening for pathophysiological conditions comprises modulating an miRNA expression pathway (i.e., for example, a small molecule drug, protein and/or hormone). In one embodiment, the method of screening for pathophysiological conditions comprises modulating an miRNA expression pathway stimulating agent (i.e., for example, a small molecule drug, protein and/or hormone). In one embodiment, the pathophysiological conditions are selected from the group consisting of precancerous and cancerous conditions, neurodegenerative diseases (i.e., for example, Alzheimer's and Parkinson's), inflammatory diseases, neuroendocrine disorders, pain management, embryogenesis and developmental disorders. In one embodiment, the method further comprises screening for the pathophysiological condition in a living organism. In one embodiment, the organism comprises an animal. In one embodiment, the animal comprises a mammal. In one embodiment, the mammal comprises a human. In one embodiment, the mammal is non-human (i.e., for example, a dog, cat, horse, cow, sheet, goat, pig etc). In one embodiment, the animal comprises an avian (i.e., for example, chicken, turkey, ostrich etc.). In one embodiment, the organism comprises a plant. In one embodiment, the plant comprises a grain. In one embodiment, the plant comprises a tobacco. In one embodiment, the plant comprises a vegetable. In one embodiment, the vegetable may be selected from the group comprising corns, potatoes, lettuces, roots, or sprouts. In one embodiment, the plant comprises a fruit. In one embodiment, the fruit may be selected from the group comprising legumes, avocados, citrus fruits, apples, pears, or peaches. In one embodiment, the plant comprises a lettuce.

In one embodiment, the present invention contemplates a method of diagnosing pathophysiological conditions. In one embodiment, the method of diagnosing comprises identifying an miRNA. In one embodiment, the miRNA is selected from the group comprising miR-150 and/or miR-186. In one embodiment, the identified miRNA level is elevated when compared to normal levels, thereby diagnosing a specific pathophysiological condition. In one embodiment, the identified miRNA levels is reduced when compared to normal levels. In one embodiment, the method of diagnosing pathophysiological conditions comprises modulating an miRNA expression pathway (i.e., for example, a small molecule drug, protein and/or hormone). In one embodiment, the method of diagnosing pathophysiological conditions comprises modulating an miRNA expression pathway stimulating agent (i.e., for example, a small molecule drug, protein and/or hormone). In one embodiment, the pathophysiological conditions are selected from the group consisting of precancerous and cancerous conditions, neurodegenerative diseases (i.e., for example, Alzheimer's and Parkinson's), inflammatory diseases, neuroendocrine disorders, pain management, embryogenesis and developmental disorders. In one embodiment, the method further comprises diagnosing pathophysiological conditions in a living organism. In one embodiment, the organism comprises an animal. In one embodiment, the animal comprises a mammal. In one embodiment, the mammal comprises a human. In one embodiment, the mammal is non-human (i.e., for example, a dog, cat, horse, cow, sheet, goat, pig etc). In one embodiment, the animal comprises an avian (i.e., for example, chicken, turkey, ostrich etc.). In one embodiment, the organism comprises a plant. In one embodiment, the plant comprises a grain. In one embodiment, the plant comprises a tobacco. In one embodiment, the plant comprises a vegetable. In one embodiment, the vegetable may be selected from the group comprising corns, potatoes, lettuces, roots, or sprouts. In one embodiment, the plant comprises a fruit. In one embodiment, the fruit may be selected from the group comprising legumes, avocados, citrus fruits, apples, pears, or peaches. In one embodiment, the plant comprises a lettuce.

In one embodiment, the present invention contemplates a method of treating pathophysiological conditions. In one embodiment, the method of treating comprises administering an miRNA molecule capable of interacting with an nucleic acid binding site. In one embodiment, the miRNA molecule is administered in the form of a naked oligonucleotide, sense molecule, antisense molecule, or a vector, wherein the miRNA interacts with an mRNA, wherein the vector is a plasmid, cosmid, bacteriophage, or a virus, wherein the virus is for example, a retrovirus, an adenovirus, or other suitable viral vector. In one embodiment, the miRNA antisense is selected from the group comprising miR-150 antisense and/or miR-186 antisense. In one embodiment, the method of treating pathophysiological conditions comprises modulating an miRNA expression pathway (i.e., for example, a small molecule drug, protein and/or hormone). In one embodiment, the method of treating pathophysiological conditions comprises modulating an miRNA expression pathway stimulating agent (i.e., for example, a small molecule drug, protein and/or hormone). In one embodiment, the pathophysiological conditions are selected from the group consisting of precancerous and cancerous conditions, neurodegenerative diseases (i.e., for example, Alzheimer's and Parkinson's), inflammatory diseases, neuroendocrine disorders, pain management, embryogenesis and developmental disorders. In one embodiment, the method further comprises treating pathophysiological conditions in a living organism. In one embodiment, the organism comprises an animal. In one embodiment, the animal comprises a mammal. In one embodiment, the mammal comprises a human. In one embodiment, the mammal is non-human (i.e., for example, a dog, cat, horse, cow, sheet, goat, pig etc). In one embodiment, the animal comprises an avian (i.e., for example, chicken, turkey, ostrich etc.). In one embodiment, the organism comprises a plant. In one embodiment, the plant comprises a grain. In one embodiment, the plant comprises a tobacco. In one embodiment, the plant comprises a vegetable. In one embodiment, the vegetable may be selected from the group comprising corns, potatoes, lettuces, roots, or sprouts. In one embodiment, the plant comprises a fruit. In one embodiment, the fruit may be selected from the group comprising legumes, avocados, citrus fruits, apples, pears, or peaches. In one embodiment, the plant comprises a lettuce.

In one embodiment, the present invention contemplates a method of providing a prognosis for pathophysiological conditions comprising a plurality of symptoms. In one embodiment, the method of providing a prognosis comprises measuring an miRNA. In one embodiment, the miRNA is selected from the group comprising miR-150 and/or miR-186. In one embodiment, the measured miRNA is within a range predicting a complete reduction of the symptoms. In one embodiment, the measured miRNA is within a range predicting a partial reduction of the symptoms. In one embodiment, the measured miRNA is within a range predicting no change in the symptoms. In one embodiment, the measured miRNA is within a range predicting a partial increase of the symptoms. In one embodiment, the measured miRNA is within a range predicting a maximal increase of the symptoms. In one embodiment, the method of providing a prognosis comprises modulating an miRNA expression pathway (i.e., for example, a small molecule drug, protein and/or hormone). In one embodiment, the method of providing a prognosis comprises modulating an miRNA expression pathway stimulating agent (i.e., for example, a small molecule drug, protein and/or hormone). In one embodiment, the pathophysiological conditions are selected from the group consisting of precancerous and cancerous conditions, neurodegenerative diseases (i.e., for example, Alzheimer's and Parkinson's), inflammatory diseases, neuroendocrine disorders, pain management, embryogenesis and developmental disorders. In one embodiment, the method further comprises providing a prognosis for medical conditions in a living organism. In one embodiment, the organism comprises an animal. In one embodiment, the animal comprises a mammal. In one embodiment, the mammal comprises a human. In one embodiment, the mammal is non-human (i.e., for example, a dog, cat, horse, cow, sheet, goat, pig etc). In one embodiment, the animal comprises an avian (i.e., for example, chicken, turkey, ostrich etc.). In one embodiment, the organism comprises a plant. In one embodiment, the plant comprises a grain. In one embodiment, the plant comprises a tobacco. In one embodiment, the plant comprises a vegetable. In one embodiment, the vegetable may be selected from the group comprising corns, potatoes, lettuces, roots, or sprouts. In one embodiment, the plant comprises a fruit. In one embodiment, the fruit may be selected from the group comprising legumes, avocados, citrus fruits, apples, pears, or peaches. In one embodiment, the plant comprises a lettuce.

In one embodiment, the present invention contemplates a method of screening for pathophysiological conditions. In one embodiment, the method of screening comprises detecting a ribonucleotide binding protein (RBP). In one embodiment, the RBP includes, but is not limited to, those described in Table 2. In one embodiment, the detected RBP level is elevated when compared to normal levels, thereby suggesting the presence of the pathophysiological condition. In one embodiment, the detected RBP level is reduced when compared to normal levels. In one embodiment, the method of screening for pathophysiological conditions comprises modulating an RPB expression pathway (i.e., for example, a small molecule drug, protein and/or hormone). In one embodiment, the method of screening for pathophysiological conditions comprises modulating an RPB expression pathway stimulating agent (i.e., for example, a small molecule drug, protein and/or hormone). In one embodiment, the pathophysiological conditions are selected from the group consisting of precancerous and cancerous conditions, neurodegenerative diseases (i.e., for example, Alzheimer's and Parkinson's), inflammatory diseases, neuroendocrine disorders, pain management, embryogenesis and developmental disorders. In one embodiment, the method further comprises screening for the pathophysiological condition in a living organism. In one embodiment, the organism comprises an animal. In one embodiment, the animal comprises a mammal. In one embodiment, the mammal comprises a human. In one embodiment, the mammal is non-human (i.e., for example, a dog, cat, horse, cow, sheet, goat, pig etc). In one embodiment, the animal comprises an avian (i.e., for example, chicken, turkey, ostrich etc.). In one embodiment, the organism comprises a plant. In one embodiment, the plant comprises a grain. In one embodiment, the plant comprises a tobacco. In one embodiment, the plant comprises a vegetable. In one embodiment, the vegetable may be selected from the group comprising corns, potatoes, lettuces, roots, or sprouts. In one embodiment, the plant comprises a fruit. In one embodiment, the fruit may be selected from the group comprising legumes, avocados, citrus fruits, apples, pears, or peaches. In one embodiment, the plant comprises a lettuce.

In one embodiment, the present invention contemplates a method of diagnosing pathophysiological conditions. In one embodiment, the method of diagnosing comprises identifying a ribonucleotide binding protein (RBP). In one embodiment, the RBP includes, but is not limited to, those RBPs described in Table 2. In one embodiment, the identified RBP level is elevated when compared to normal levels, thereby diagnosing a specific pathophysiological condition. In one embodiment, the identified RBP level is reduced when compared to normal levels. In one embodiment, the method of diagnosing pathophysiological conditions comprises modulating an RBP expression pathway (i.e., for example, a small molecule drug, protein and/or hormone). In one embodiment, the method of diagnosing pathophysiological conditions comprises modulating an RBP expression pathway stimulating agent (i.e., for example, a small molecule drug, protein and/or hormone). In one embodiment, the pathophysiological conditions are selected from the group consisting of precancerous and cancerous conditions, neurodegenerative diseases (i.e., for example, Alzheimer's and Parkinson's), inflammatory diseases, neuroendocrine disorders, pain management, embryogenesis and developmental disorders. In one embodiment, the method further comprises diagnosing pathophysiological conditions in a living organism. In one embodiment, the organism comprises an animal. In one embodiment, the animal comprises a mammal. In one embodiment, the mammal comprises a human. In one embodiment, the mammal is non-human (i.e., for example, a dog, cat, horse, cow, sheet, goat, pig etc). In one embodiment, the animal comprises an avian (i.e., for example, chicken, turkey, ostrich etc.). In one embodiment, the organism comprises a plant. In one embodiment, the plant comprises a grain. In one embodiment, the plant comprises a tobacco. In one embodiment, the plant comprises a vegetable. In one embodiment, the vegetable may be selected from the group comprising corns, potatoes, lettuces, roots, or sprouts. In one embodiment, the plant comprises a fruit. In one embodiment, the fruit may be selected from the group comprising legumes, avocados, citrus fruits, apples, pears, or peaches. In one embodiment, the plant comprises a lettuce.

In one embodiment, the present invention contemplates a method, of treating pathophysiological conditions. In one embodiment, the method comprises administering a molecule capable of interacting with a ribonucleic acid protein (RBP). In one embodiment, the molecule is administered in the form of a naked oligonucleotide, sense molecule, antisense molecule, or a vector. In one embodiment, the molecule interacts with mRNA-RPB binding. In one embodiment, the method further comprises a vector encoding a molecule capable of interacting with a ribonucleic acid protein (RBP). In one embodiment, the vector comprises a plasmid, cosmid, bacteriophage, or a virus, wherein the virus is for example, a retrovirus, an adenovirus, or other suitable viral vector. In one embodiment, the RPB antisense includes, antisense directed to RBPs including, but not limited to, those described in Table 2. In one embodiment, the method of treating pathophysiological conditions comprises modulating an RBP expression pathway (i.e., for example, a small molecule drug, protein and/or hormone). In one embodiment, the method of treating pathophysiological conditions comprises modulating an RBP expression pathway stimulating agent (i.e., for example, a small molecule drug, protein and/or hormone). In one embodiment, the pathophysiological conditions are selected from the group consisting of precancerous and cancerous conditions, neurodegenerative diseases (i.e., for example, Alzheimer's and Parkinson's), inflammatory diseases, neuroendocrine disorders, pain management, embryogenesis and developmental disorders. In one embodiment, the method further comprises treating pathophysiological conditions in a living organism. In one embodiment, the organism comprises an animal. In one embodiment, the animal comprises a mammal. In one embodiment, the mammal comprises a human. In one embodiment, the mammal is non-human (i.e., for example, a dog, cat, horse, cow, sheet, goat, pig etc). In one embodiment, the animal comprises an avian (i.e., for example, chicken, turkey, ostrich etc.). In one embodiment, the organism comprises a plant. In one embodiment, the plant comprises a grain. In one embodiment, the plant comprises a tobacco. In one embodiment, the plant comprises a vegetable. In one embodiment, the vegetable may be selected from the group comprising corns, potatoes, lettuces, roots, or sprouts. In one embodiment, the plant comprises a fruit. In one embodiment, the fruit may be selected from the group comprising legumes, avocados, citrus fruits, apples, pears, or peaches. In one embodiment, the plant comprises a lettuce.

In one embodiment, the present invention contemplates a method of providing a prognosis for pathophysiological conditions comprising a plurality of symptoms. In one embodiment, the method of providing a prognosis comprises measuring a ribonucleotide binding protein (RBP). In one embodiment, the RBP includes, but is not limited to, those RBPs described in Table 2. In one embodiment, the measured RBP is within a range predicting a complete reduction of the symptoms. In one embodiment, the measured RBP is within a range predicting a partial reduction of the symptoms. In one embodiment, the measured RBP is within a range predicting no change in the symptoms. In one embodiment, the measured RBP is within a range predicting a partial increase of the symptoms. In one embodiment, the measured RBP is within a range predicting a maximal increase of the symptoms. In one embodiment, the method of providing a prognosis comprises modulating an RBP expression pathway (i.e., for example, a small molecule drug, protein and/or hormone). In one embodiment, the method of providing a prognosis comprises modulating an RBP expression pathway stimulating agent (i.e., for example, a small molecule drug, protein and/or hormone). In one embodiment, the pathophysiological conditions are selected from the group consisting of precancerous and cancerous conditions, neurodegenerative diseases (i.e., for example, Alzheimer's and Parkinson's), inflammatory diseases, neuroendocrine disorders, pain management, embryogenesis and developmental disorders. In one embodiment, the method further comprises providing a prognosis for medical conditions in a living organism. In one embodiment, the organism comprises an animal. In one embodiment, the animal comprises a mammal. In one embodiment, the mammal comprises a human. In one embodiment, the mammal is non-human (i.e., for example, a dog, cat, horse, cow, sheet, goat, pig etc). In one embodiment, the animal comprises an avian (i.e., for example, chicken, turkey, ostrich etc.). In one embodiment, the organism comprises a plant. In one embodiment, the plant comprises a grain. In one embodiment, the plant comprises a tobacco. In one embodiment, the plant comprises a vegetable. In one embodiment, the vegetable may be selected from the group comprising corns, potatoes, lettuces, roots, or sprouts. In one embodiment, the plant comprises a fruit. In one embodiment, the fruit may be selected from the group comprising legumes, avocados, citrus fruits, apples, pears, or peaches. In one embodiment, the plant comprises a lettuce.

In one embodiment, the present invention contemplates a method, comprising: a) providing; i) a cell capable of expressing a pathophysiological biomarker; and ii) an environmental stimuli capable of modulating expression of said biomarker; b) contacting said cell with said environmental stimuli under conditions such that said biomarker expression is altered. In one embodiment, the method further comprises determining a biological impact of said environmental stimuli. In one embodiment, the biomarker expression is increased. In one embodiment, the biomarker expression is decreased. In one embodiment, the environmental stimuli comprises a carcinogen (i.e., for example, thereby causing cancer). In one embodiment, the environmental stimuli comprises a toxin (i.e., for example, thereby causing a neurodegenerative disease). In one embodiment, the environmental stimuli comprises a hormone (i.e., for example, thereby causing a neuroendocrine disease). In one embodiment, the environmental stimuli comprises a virus (i.e., for example, thereby causing a developmental disease). In one embodiment, the environmental stimuli comprises a peptide (i.e., for example, thereby causing an inflammatory disease). In one embodiment, the environmental stimuli comprises a small organic molecule (i.e., for example, thereby causing a pain management disorder). In one embodiment, the pathophysiological biomarker comprises microRNA. In one embodiment, the microRNA biomarker comprises miR-150. In one embodiment, the microRNA biomarker comprises miR-186. In one embodiment, the pathophysiological biomarker comprises mRNA. In one embodiment, the mRNA comprises $P2X_7$ mRNA.

DEFINITIONS

The term "cancer", as used herein refers to any presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. The number of cancer cells in a subject's body can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The term "inhibit the proliferation of a cancer cell" as used herein, means to kill a cancer cell, or permanently or temporarily arrest or slow the growth of a cancer cell. Inhibition of cancer cell proliferation can be inferred if the number of cancer cells in a subject remains constant or decreases after administration of a miRNA gene product and/or an miRNA gene expression-inhibiting compound. An inhibition of cancer cell proliferation can also be inferred if the absolute number of such cells increases, but the rate of tumor growth decreases.

The term "detecting" as used herein, refers to obtaining indirect evidence regarding the likelihood of the presence of a pathophysiological condition or assessing the predisposition of an organism to the development of the pathophysiological condition (i.e., for example, uterine cancer).

The term "diagnosing" as used herein, refers to establishing scientific evidence demonstrating the actual presence of a pathophysiological condition (i.e., for example, uterine cancer).

The term "tumor" as used herein, refers to all neoplastic cell growth and proliferation, whether malignant or benign, and all precancerous and cancerous cells and tissues. The size of a tumor can be ascertained by direct visual observation, or by diagnostic imaging methods, including, but not limited to, X-ray, magnetic resonance imaging, ultrasound, and scintigraphy. Diagnostic imaging methods used to ascertain size of the tumor can be employed with or without contrast agents. The size of a tumor can also be ascertained by physical means, such as palpation of the tissue mass or measurement of the tissue mass with a measuring instrument, such as a caliper.

The term "precancerous" as used herein, refers to cells or tissues having characteristics relating to changes that may lead to malignancy or cancer. Examples include, but are not limited to; adenomatous growths in uterus, skin, colon, ovary, breast, or prostate. Examples also include, abnormal neoplastic, in addition to dysplastic nevus syndromes, polyposis syndromes, prostatic dysplasia, and other such neoplasms, whether the precancerous lesions are clinically identifiable or not.

The term "differentially expressed gene transcript", as used herein, refers to any gene transcript that is found in different numbers of copies in different cell or tissue types of an organism. For example, a first cell having a tumor or cancer may have different number of copies (either more or less) than a second cell not having a tumor or cancer (i.e., a normal or healthy cell). The differences in copy number may result from either differential transcription rates or differential degradation rates of the gene transcript.

The term "target gene" as used herein, refers to any differentially expressed gene transcript in which modulation of the level of gene expression or of gene product activity prevents and/or ameliorates pathophysiological condition symptoms. Thus, compounds that modulate the expression of a target gene, the target genes, or the activity of a target gene product can be used in the screening, diagnosis, treatment or prognoses of the pathophysiological condition. One particular target gene of the present invention is the $P2X_7$ gene.

The term "gene" as used herein, refers to any region on the genome that is capable of being transcribed to an RNA that either has a regulatory function, a catalytic function, and/or encodes a protein. An eukaryotic gene typically has introns and exons, which may organize to produce different RNA splice variants that encode alternative versions of a mature protein. For example, $P2X_7$-encoding transcripts that may be found, including, but not limited to, splice variants, allelic variants and transcripts that occur because of alternative promoter sites or alternative poly-adenylation sites.

The term "full-length gene" or "full length RNA" as used herein, encompasses any naturally occurring splice variants, allelic variants, other alternative transcripts, splice variants generated by recombinant technologies which bear the same function as the naturally occurring variants, and the resulting RNA molecules.

The term "gene fragment" as used herein, refers to any portion from a gene, which may or may not represent a functional domain, for example, a catalytic domain, a DNA binding domain, etc. A fragment may preferably include nucleotide sequences that encode for at least 25 contiguous amino acids, and preferably at least about 30, 40, 50, 60, 65, 70, 75 or more contiguous amino acids or any integer thereabout or therebetween.

The term "detectable RNA expression level" as used herein, refers to any RNA level that is detectable by standard techniques currently known in the art or those that become standard at some future time, and include, but are not limited to, differential display, RT (reverse transcriptase)-coupled polymerase chain reaction (PCR), Northern Blot, and/or RNase protection analyses. The degree of differences in expression levels need only be large enough to be visualized or measured via standard characterization techniques.

The term "transformed cell", as used herein, refers to any cell into which (or into predecessor or an ancestor of which) a nucleic acid molecule encoding a polypeptide of the invention has been introduced, by means of, for example, recombinant DNA techniques or viruses. The nucleic acid molecules of the invention, for example, the $P2X_7$ genes or their subsequences or miR-150 and/or miR-186, can be inserted into a vector which will facilitate expression of the insert. The nucleic acid molecules and the polypeptides they encode can be used directly as diagnostic or therapeutic agents, or can be used (directly in the case of the polypeptide or indirectly in the case of a nucleic acid molecule) to generate antibodies that, in turn, are clinically useful as a therapeutic or diagnostic agent. Accordingly, vectors containing the nucleic acids of the invention, cells transfected with these vectors, the polypeptides expressed, and antibodies generated against either the entire polypeptide or an antigenic fragment thereof, are among the aspects of the invention.

The term "structural gene" as used herein, refers to any DNA sequence that is transcribed into messenger RNA (mRNA) which is then translated into a sequence of amino acids characteristic of a specific polypeptide.

The term "isolated DNA molecule" as used herein, refers to any fragment of DNA that has been separated from the chromosomal or genomic DNA of an organism. Isolation also is defined to connote a degree of separation from original source or surroundings. Isolated DNA molecules can be subjected to procedures that remove contaminants such that the DNA molecule is considered purified, that is, towards a more homogeneous state.

The term "complementary DNA" as used herein, refers to any single-stranded DNA molecule that is formed from an mRNA template by the enzyme reverse transcriptase. Typically, a primer complementary to portions of the mRNA is employed for the initiation of reverse transcription.

The term "cDNA" as used herein, refers to any double-stranded DNA molecule that comprises a single-stranded complementary DNA molecule and its complement DNA strand.

The term "expression" as used herein, refers to any biosynthesis of a gene product. For example, in the case of a structural gene, expression involves transcription of the structural gene into mRNA and the translation of mRNA into one or more polypeptides.

The term "amplification" as used herein, refers to any duplication, multiplication, or multiple expression of nucleic acids or a gene, in vivo or in vitro, yielding at least about a 2.5 fold increase in copy number. For example, amplification of the $P2X_7$ gene resulting in a copy number greater than or equal to 2.5 is deemed to have been amplified. However, an increase in $P2X_7$ gene copy number less than 2.5 fold can still be considered as an amplification of the gene. The 2.5 fold figure is due to current detection limits, rather than a biological state.

The term "cloning vector" as used herein, refers to any nucleic acid molecule, for example, a plasmid, cosmid, or bacteriophage that has the capability of replicating autonomously in a host cell. Cloning vectors typically contain: (i) one or a small number of restriction endonuclease recognition sites at which foreign DNA sequences can be inserted in a determinable fashion without loss of an essential biological function of the vector; and (ii) a marker gene that is suitable for use in the identification and/or selection of cells transformed or transfected with the cloning vector. Marker genes, for example, may include genes that provide tetracycline resistance or ampicillin resistance.

The term "expression vector" as used herein, refers to any nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers.

The term "recombinant host" as used herein, refers to any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

The term "antisense" as used herein, refers to any first nucleic acid molecule that interacts with, inhibits, or interferes with a second nucleic acid. For example, an antisense RNA may inhibit the transcription of a DNA structural gene product (i.e., for example, mRNA). In eukaryotes, RNA polymerase catalyzes the transcription of a structural gene to produce mRNA. A DNA molecule can be designed to contain an RNA polymerase template in which the antisense RNA transcript has a sequence that is complementary to that of a transcribed mRNA.

The term "antisense nucleic acid" as used herein, refers to any nucleic acid molecule that binds to a target nucleic acid (i.e., for example, RNA) by means of RNA-RNA or RNA-DNA or RNA-peptide nucleic acid interactions, which alters the activity of the target nucleic acid. Antisense nucleic acids suitable for use in the present methods are single-stranded nucleic acids (e.g., RNA, DNA, RNA-DNA chimeras, PNA) that generally comprise a nucleic acid sequence complementary to a contiguous nucleic acid sequence in an miRNA gene product.

The term "enzymatic nucleic acid" as used herein, refers to any nucleic acid comprising a substrate binding region that has complementarity to a contiguous nucleic acid sequence of an miRNA gene product, and which is able to specifically cleave the miRNA gene product.

The term "operably linked" as used herein, refers to any connection between regulatory elements and a gene or its coding region. For example, gene expression is typically placed under the control of certain regulatory elements, including but not limited to constitutive or inducible promoters, tissue-specific regulatory elements, and enhancers. Such a gene or coding region is said to be "operably linked to" or "operatively linked to" or "operably associated with" the regulatory elements, meaning that the gene or coding region is controlled or influenced by the regulatory element.

The term "sequence homology" as used herein, refers to any sequence relationships between two or more nucleic acids, polynucleotides, proteins, or polypeptides, and is understood in the context of and in conjunction with the following terms:

(a) A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

(b) A "comparison window" includes reference to a contiguous and specified segment of a polynucleotide sequence, wherein the polynucleotide sequence may be compared to a reference sequence and wherein the portion of the polynucleotide sequence in the comparison window may comprise additions, substitutions, or deletions (i.e., gaps) compared to the reference sequence (which does not comprise additions, substitutions, or deletions) for optimal alignment of the two sequences. Generally, the comparison window is at least 20 contiguous nucleotides in length, and optionally can be 30, 40, 50, 100, or longer. Those of skill in the art understand that to avoid a misleadingly high similarity to a reference sequence due to inclusion of gaps in the polynucleotide sequence a gap penalty is typically introduced and is subtracted from the number of matches.

c) A "sequence alignment" may be determined by a variety of methods. For example, alignment of sequences for comparison may be conducted by the: i) local homology algorithm (Smith et al., *Adv. Appl. Math.,* 2: 482 (1981)); ii) homology alignment algorithm (Needleman et al., *Mol. Biol.,* 48: 443 (1970); iii) search for similarity method (Pearson et al., *Proc. Natl. Acad. Sci. USA,* 8:2444 (1988); iv) computerized implementations of these algorithms, including, but not limited to, GAP®, BESTFIT®, BLAST®, FASTA®, and TFASTA® in the Wisconsin Genetics Software Package, (Genetics Computer Group, 7 Science Dr., Madison, Wis., USA); and CLUSTAL® in the PC/Gene program (Intelligenetics, Mountain View, Calif.). Higgins et al., *Gene* 73: 237-244 (1988); Corpet et al., *Nucleic Acids Research,* 16:881-90 (1988); Huang et al., *Computer Applications in the Biosciences,* 8:1-6 (1992); and Pearson et al., *Methods in Molecular Biology* 24:7-331 (1994). The BLAST® family of programs can be used for database similarity searches and includes, but is not limited to: i) BLASTN® for nucleotide query sequences against nucleotide database sequences; ii) BLASTX® for nucleotide query sequences against protein database sequences; iii) BLASTP® for protein query sequences against protein database sequences; iv) TBLASTN® for protein query sequences against nucleotide database sequences; and v) TBLASTX® for nucleotide query sequences against nucleotide database sequences. In: *Current Protocols in Molecular Biology*, Chapter 19, Ausubel, et al., Eds., Greene Publishing and Wiley-Interscience, New York (1995).

(d) A "Sequence identity" or "identity" in the context of two nucleic acid or polypeptide sequences includes reference to the residues in the two sequences which are the same when aligned for maximum correspondence over a specified comparison window, and can take into consideration additions, deletions and substitutions. When percentage of sequence identity is used in reference to proteins residue positions which are not identical often differ by conservative amino acid substitutions, wherein amino acid residues are substituted for other amino acid residues with similar chemical properties (for example, charge or hydrophobicity) and therefore do not deleteriously change the functional properties of the molecule. Where sequences differ in conservative substitutions, the percent sequence identity may be adjusted upwards to correct for the conservative nature of the substitution. Sequences which differ by such conservative substitutions are said to have sequence similarity. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1.

(e) A "percentage of sequence identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "homologous", as used herein in their various grammatical forms in the context of polynucleotide sequences or protein sequences means that a sequence has a desired identity, for example, at least 60% identity, preferably at least 70% sequence identity, more preferably at least 80%, still more preferably at least 90% and even more preferably at least 95%, compared to a reference sequence using one of the alignment programs described using standard parameters. These values can be appropriately adjusted to determine corresponding identity of proteins encoded by two nucleotide sequences by taking into account nucleotide codon degeneracy, amino acid similarity, reading frame positioning and the like. Substantial identity of amino acid sequences for these purposes normally means sequence identity of at least 60%, more preferably at least 70%, 80%, 90%, and even more preferably at least 95%.

The term "hybridize" or "hybridization" as used herein, refers to the attachment of nucleotide sequences that are substantially identical under stringent conditions. However, nucleic acids which do not hybridize to each other under stringent condition's are still substantially identical if the polypeptides which they encode are substantially identical. This may occur, for example, when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid, although such cross-reactivity is not required for two polypeptides to be deemed substantially identical.

The term "organism" as used herein refers to any living entity including the Animal Kingdom and Plant Kingdom. An organism is typically of eukaryotic nature, for example, insects, protozoa, birds, fish, reptiles, and preferably a mammal, for example, rat, mouse, cow, dog, guinea pig, or rabbit, and more preferably a primate, for example, chimpanzees, or humans such as a patient in need of diagnostic review, treatment and/or monitoring of therapy. However, organisms also include agricultural plants including, but not limited to, grains, vegetables, fruits etc.

The term "biological sample" as used herein, refers to any sample obtained from an organism, including sample of biological tissue or fluid origin, obtained, reached, or collected in vivo or in situ. A biological sample also includes samples from a region of a biological subject containing pathophysiological tissues. Such samples can be, but are not limited to, organs, tissues, fractions and cells isolated from mammals including, humans such as a patient, mice, and rats. Biological samples also may include sections of the biological sample including tissues, for example, frozen sections taken for histologic purposes. A biological sample is typically of an eukaryotic origin, for example, insects, protozoa, birds, fish, reptiles, and preferably a mammal, for example, rat, mouse, cow, dog, guinea pig, or rabbit, and more preferably a primate, for example, chimpanzees or humans. Plant samples may include, but are not limited to, leafs, stems, stamens, pistels etc.

The term "overexpression" as used herein, refers to any detectable increase or elevated level of a polynucleotide or protein in comparison with a control level. Such a comparison may be carried out by statistical analyses on numeric measurements of the expression; or, it may be done through visual examination of experimental results by qualified researchers.

The term "inhibitor" or "modulator" as used herein, refers to any compound or molecule that can change the activity of an identified function. Such compounds or molecules may include, but are not limited to, small organic compounds, nucleic acids, peptides, polypeptides, proteins, peptide nucleic acids or the like. For example, a compound may inhibit the interaction of an miRNA (i.e., for example, miR-150) with an mRNA (i.e., for example, $P2X_7$ mRNA).

The terms "isolated," "purified," or "biologically pure" as used herein, refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified. Various levels of purity may be applied as needed according to this invention in the different methodologies set forth herein; the customary purity standards known in the art may be used if no standard is otherwise specified.

The term "isolated nucleic acid molecule" as used herein, refers to any nucleic acid molecule, depending upon the circumstance, that is separated from the 5' and 3' coding sequences of genes or gene fragments contiguous in the naturally occurring genome of an organism. The term "isolated nucleic acid molecule" also includes nucleic acid molecules which are not naturally occurring, for example, nucleic acid molecules created by recombinant DNA techniques.

The term "nucleic acid" as used herein, refers to any deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral methyl phosphonates, 2-O-methyl ribonucleotides, and peptide-nucleic acids (PNAs).

The term "host cell" as used herein, refers to any naturally occurring cell or a transformed cell or a transfected cell that contains an expression vector and supports the replication or expression of the expression vector. Host cells may be cultured cells, explants, cells in vivo, and the like. Host cells may be prokaryotic cells, for example, *E. coli*, or eukaryotic cells, for example, yeast, insect, amphibian, or mammalian cells, for example, Vero, CHO, HeLa, and others.

The term "amino acid" as used herein, refers to any naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, γ-carboxyglutamate, and O-phosphoserine, phosphothreonine.

The term "amino acid analogs" as used herein, refer to any compound that has the same basic chemical structure as a naturally occurring amino acid, i.e., a carbon that is bound to a hydrogen, a carboxyl group, an amino group, and an R group, for example, homoserine, norleucine, methionine sulfoxide, methionine methyl sulfonium. Such analogs have modified R groups (for example, norleucine) or modified peptide backbones, but retain the same basic chemical structure as a naturally occurring amino acid.

The term "amino acid mimetics" as used herein, refer to any chemical compounds that have a structure that is different from the general chemical structure of an amino acid, but that function in a manner similar to a naturally occurring amino acid.

The term "conservatively modified variants" as used herein, apply to both amino acid and nucleic acid sequences. With respect to particular nucleic acid sequences, conservatively modified variants refers to those nucleic acids which encode identical or similar amino acid sequences and include degenerate sequences. For example, the codons GCA, GCC, GCG and GCU all encode alanine. Thus, at every amino acid position where an alanine is specified, any of these codons can be used interchangeably in constructing a corresponding nucleotide sequence. The resulting nucleic acid variants are conservatively modified variants, since they encode the same protein (assuming that is the only alternation in the sequence). Each codon in a nucleic acid, except for AUG (sole codon for methionine) and UGG (tryptophan), can be modified conservatively to yield a functionally-identical peptide or protein molecule.

As to amino acid sequences, substitutions, deletions, or additions to a polypeptide or protein sequence which alter, add or delete a single amino acid or a small number (typically less than about ten) of amino acids is a "conservatively modified variant" where the alteration results in the substitution of an amino acid with a chemically similar amino acid. Conservative amino acid substitutions include, but are not limited to, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

The terms "protein", "peptide" and "polypeptide" as used herein, describe any chain of amino acids, regardless of length or post-translational modification (for example, glycosylation or phosphorylation). Thus, the terms can be used interchangeably herein to refer to a polymer of amino acid residues. The terms also apply to amino acid polymers in which one or more amino acid residue is an artificial chemical mimetic of a corresponding naturally occurring amino acid. Thus, the term "polypeptide" includes, but is not limited to, full-length, naturally occurring proteins as well as recombinantly or synthetically produced polypeptides that correspond to a full-length naturally occurring protein or to particular domains or portions of a naturally occurring protein. The term also encompasses mature proteins which have an added amino-terminal methionine to facilitate expression in prokaryotic cells.

The term "functional polypeptide" as used herein, refers to any polypeptide that possesses at least one biological function or activity. These functions or activities include the ability to bind some or all of the proteins which normally bind to $P2X_7$ protein. A functional polypeptide may also contain a primary amino acid sequence that has been modified from that considered to be the standard sequence of any protein described herein. Preferably these modifications are conservative amino acid substitutions, as described herein.

The term "nucleic acid probe", "oligonucleotide probe", or "probe" as used herein, refers to any nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Probes may bind target sequences lacking complete complementarity with the probe sequence depending upon the stringency of the hybridization conditions. The probes may comprise labels and/or markers including, but not limited to, isotopes, chromophores, lumiphores, chromogens, or biotin.

The term "selectively (or specifically) hybridizes to" as used herein, refers to any binding, duplexing, or hybridizing of a molecule only to a particular nucleotide sequence under stringent hybridization conditions when that sequence is present in a complex mixture (for example, total cellular or library DNA or RNA).

The term "stringent hybridization conditions" as used herein, refers any condition under which a probe will hybridize to its target complementary sequence, typically in a complex mixture of nucleic acids, but to no other sequences. Stringent conditions are sequence-dependent and circumstance-dependent; for example, longer sequences can hybridize with specificity at higher temperatures. In: *Techniques in Biochemistry and Molecular Biology-Hybridization with Nucleic Probes*, Tijssen et al., "Overview of principles of hybridization and the strategy of nucleic acid assays" (1993) (incorporated herein by reference in its entirety). For example, a "stringent hybridization condition" results in the stable hybridization of nucleotide sequences that are at least 60% homologous to each other. Preferably, the conditions are such that sequences at least about 65%, more preferably at least about 70%, and even more preferably at least about 75% or more homologous provide a stable hybridization of two nucleotide sequences.

Generally, stringent conditions are selected to be about 5 to 10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (for example, 10 to 50 nucleotides) and at least about 60° C. for long probes (for example, greater than 50 nucleotides). Stringent conditions also may be achieved with the addition of destabilizing agents, for example, formamide. For selective or specific hybridization, a positive signal is at least two times background, preferably 1× background hybridization.

Exemplary stringent hybridization conditions can be as following, for example: 50% formamide, 5×SSC and 1% SDS, incubating at 42° C., or 5×SSC and 1% SDS, incubating at 65° C., with wash in 0.2×SSC and 0.1% SDS at 65° C. Alternative conditions include, for example, conditions at least as stringent as hybridization at 68° C. for 20 hours, followed by washing in 2×SSC, 0.1% SDS, twice for 30 minutes at 55° C. and three times for 15 minutes at 60° C. Another alternative set of conditions is hybridization in 6×SSC at about 45° C., followed by one or more washes in 0.2×SSC, 0.1% SDS at 50-65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C. to 95° C. for 30 sec. to 2 min., an annealing phase lasting 30 sec. to 2 min., and an extension phase of about 72° C. for 1 to 2 min.

The term "moderately stringent hybridization conditions" as used herein, refers to any condition allowing hybridization of nucleic acids that do not hybridize to each other under stringent conditions but are still substantially identical (i.e., if the polypeptides which they encode are substantially identical). This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The term "about" or "approximately" as used herein, in the context of numerical values and ranges refers to values or ranges are close to the recited values or ranges such that the invention can perform as intended.

The term "antibody" refers to a polypeptide comprising a framework region encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 2 kDa) and one "heavy" chain (up to about 70 kDa). Antibodies exist, for example, as intact immunoglobulins or as a number of well-characterized fragments produced by digestion with various peptidases. While various antibody fragments are defined in terms of the digestion of an intact antibody, such fragments may be synthesized de novo chemically or via recombinant DNA methodologies. Thus, the term antibody, as used herein, also includes antibody fragments produced by the modification of whole antibodies, those synthesized de novo using recombinant DNA methodologies (for example, single chain Fv), humanized antibodies, and those identified using phage display libraries. For preparation of antibodies—recombinant, monoclonal, or polyclonal antibodies—any technique known in the art can be used with this invention (see, for example, Kohler et al., *Nature,* 256:495-497 (1975); Kozbor et al., *Immunology Today* 4:72 (1983); and Cole et al., In: *Monoclonal Antibodies and Cancer Therapy,* pp. 77-96, Alan R. Liss, Inc. (1998).

The term "tumor-cell killing" as used herein, refers to any inhibition of tumor cell proliferation by means of blocking a function or binding to block a pathway related to tumor-cell proliferation. For example, inhibition of miRNA (i.e., for example, miR-150) binding to mRNA (i.e., for example, $P2X_7$ mRNA) blocks a pathway resulting in tumor-cell proliferation.

The term "anti-$P2X_7$ antibody" as used herein, refers to any antibody or antibody fragment that specifically binds a polypeptide encoded by a $P2X_7$ gene, mRNA, cDNA, or a subsequence thereof. These antibodies can mediate anti-proliferative activity on tumor-cell growth.

The term "immunoassay" as used herein, refers to any assay that utilizes the binding interaction between an antibody and an antigen. Typically, an immunoassay uses the specific binding properties of a particular antibody to isolate, target, and/or quantify the antigen.

The term "specifically (or selectively) binds to an antibody" or "specifically (or selectively) immunoreactive with" as used herein, when referring to a protein or peptide, refers to any binding reaction that is determinative of the presence of the protein in a heterogeneous population of proteins and other biologics. For example, under designated immunoassay conditions, specified antibodies bind to a particular protein at a level at least two times the background and do not substantially bind in a significant amount to other proteins present in the sample. Specific binding to an antibody under such conditions may require an antibody that is selected for its specificity for a particular protein. For example, antibodies raised to a particular $P2X_7$ polypeptide can be selected to obtain only those antibodies that are specifically immunoreactive with a $P2X_7$ polypeptide, and not with other proteins, except for polymorphic variants, orthologs, and alleles of a specific $P2X_7$ polypeptide.

The term "miRNA" as used herein, refers to any microRNA, a class of small RNA molecules or a small non-coding RNA molecules, that are capable of causing interference, inhibition of RNA translation into protein, and can cause post-transcriptional silencing of specific genes in cells, for example, mammalian cells (including human cells) and in the body, for example, mammalian bodies (including humans). Zeng et al., *RNA,* 9:112-123 (2003); Kidner et al., *Trends Genet.* 19:13-16 (2003); Dennis C, *Nature,* 420:732 (2002); and Couzin J, *Science* 298:2296-2297 (2002).

The term "aptamer" as used herein, refers to any peptide/peptide-like molecule or any nucleic acid/nucleic acid-like molecule that is capable of binding to a specific molecule of interest (i.e., for example, $P2X_7$) with high affinity and specificity. An aptamer also can be a peptide or a nucleic acid molecule that mimics the three dimensional structure of active portions of the peptides or the nucleic acid molecules of the invention. James W., *Current Opinion in Pharmacology,* 1:540-546 (2001). An aptamer may also be a chemical mimetic; for example, a synthetic peptide aptamer or peptidomimetic. It is preferably a short oligomer selected for binding affinity and bioavailability having characteristics including, but not limited to, passage across the plasma and nuclear membranes, resistance to hydrolysis of oligomeric linkages, absorbance into cellular tissue, and resistance to metabolic breakdown. A chemical mimetic aptmer may be chemically synthesized with at least one non-natural analog of a nucleoside or amino acid (for example, modified base or ribose, designer or non-classical amino acid, D or L optical isomer). Modification also may take the form of acylation, glycosylation, methylation, phosphorylation, sulfation, or combinations thereof. Oligomeric linkages may be phosphodiester or peptide bonds; linkages comprised of a phosphorus, nitrogen, sulfur, oxygen, or carbon atom (for example, phosphorothionate, disulfide, lactam, or lactone bond); or combinations thereof. The chemical mimetic may have significant secondary structure (for example, a ribozyme) or be constrained (for example, a cyclic peptide).

The term "peptide aptamer" as used herein, refers to any polypeptide or polypeptide-like molecule that is capable of binding to a specific molecule of interest (i.e., for example, $P2X_7$) with high affinity and specificity. A peptide aptamer also can be a polypeptide molecule that mimics the three dimensional structure of active portions of the polypeptide molecules of the invention. A peptide-aptamer can be designed to mimic the recognition function of complementarity determining regions of immunoglobulins, for example. The aptamer can recognize different epitopes on the protein surface (i.e., for example, $P2X_7$) with dissociation equilibrium constants in the nanomolar range; those inhibit the protein (i.e., for example, $P2X_7$) activity. Peptide aptamers are analogous to monoclonal antibodies, with the advantages that they can be isolated together with their coding genes, that their small size facilitates solution of their structures, and that they can be designed to function inside cells. An peptide aptamer may typically range between about 3 and about 100 amino acids or the like in length. More commonly, a peptide aptamer is between about 10 and about 35 amino acids or the like in length. Peptide-aptamers may be prepared by any known method, including synthetic, recombinant, and purification methods. Colas et al., *Nature* 380:548-550 (1996) (incorporated herein by reference in its entirety).

The term "nucleic acid aptamer" as used herein, refers to any nucleic acid or a nucleic acid-like molecule that is capable of binding to a specific molecule of interest (i.e., for example, $P2X_7$) with high affinity and specificity. A nucleic acid aptamer also can be a nucleic acid molecule that mimics the three dimensional structure of active portions of the nucleic acid molecules of the invention. A nucleic acid aptamer may typically range between about 9 and about 300 nucleotides or the like in length. More commonly, a nucleic acid aptamer is between about 30 and about 100 nucleotides or the like in length. Nucleic acid-aptamers may be prepared by any known method, including synthetic, recombinant, and purification methods. Colas et al., *Nature* 380:548-550 (1996)(incorporated herein by reference in its entirety).

The term "effective amount" as used herein, refers to an amount of miRNA sufficient to reduce the symptoms of, and/or patient suffering from, a specific pathophysiological condition. For example, the symptoms of uterine cancer may be reduced by administering "an effective amount" of either miR-150 and/or miR-186 to a patient, wherein the proliferation of the cancer is reduced.

The term, "isolated miRNA" or "isolated mRNA gene product" as used herein, refers to any miRNA that is synthesized, altered, and/or removed from the natural state through human intervention. For example, an miRNA gene product naturally present in a living animal is not "isolated." Alternatively, a synthetic miRNA gene product, or an miRNA gene product partially, or completely, separated from the coexisting materials of its natural state, is "isolated." An isolated miRNA gene product can exist in substantially purified form, or can exist in a cell into which the miRNA gene product has been delivered (i.e., for example, by transfection and/or incorporation). Thus, an miRNA gene product which is deliberately delivered to, or expressed in, a cell is considered an "isolated" miRNA gene product. An miRNA gene product produced inside a cell by from an miRNA precursor molecule is also considered to be "isolated" molecule.

As used herein, "in operable connection with a polyT termination sequence" means that the nucleic acid sequences encoding the sense or antisense strands are immediately adjacent to the polyT termination signal in the 5' direction. During transcription of the miRNA sequences from the vector, the polyT termination signals act to terminate transcription.

Micrographs a-c: Cultures of normal human foreskin keratinocytes were either not hybridized with a probe (a); hybridized with a sense $P2X_7$ probe (b); or hybridized with an antisense $P2X_7$ probe (c). Specific hybridization of the $P2X_7$ probe in c is seen as an intense perinuclear and cytoplasmic reaction with the anti-digoxigenin antibody. The experiment was repeated twice with similar trends.

Micrographs d-k: Tetracycline repressor-expressing Madin-Darby canine kidney cells (MDCK) were transfected with either the $P2X_7$ cDNA or the $P2X_{7-j}$ cDNA, grown in the absence of doxycyline(Dox−) or presence (Dox+) of doxycyline, and hybridized either with the sense $P2X_7$ probe (S) or with the antisense $P2X_7$ probe (AS). Nuclei were not stained. Specific hybridization of the $P2X_7$ probe was seen only in doxycyline-treated cells transfected with the $P2X_7$ cDNA and hybridized with the antisense $P2X_7$ probe (g). The experiment was repeated twice with similar trends.

Micrographs 1-x: In situ hybridization with the antisense $P2X_7$ probe of cross-sections of human normal endometrial tissues (l, m); human adenocarcinoma endometrial tissues (m, o); human normal endocervical tissues (p, q); human adenocarcinoma endocervical tissues (r, s); human normal ectocervical tissues (t-v); and human squamous cell carcinoma ectocervical tissues (w, x). Magnifications: x4 (l, n, p, r, t, v, and w); or x20 (m, o, q, s, u, and x).

Micrograph v: Cross-section of a normal ectocervix hybridized with a sense $P2X_7$ probe.

Micrographs l, m, p, q, t, and u: Specific hybridization of an antisense $P2X_7$ probe was seen in the epithelia of the normal tissues.

These experiments were repeated three to five times with similar trends.

Figure 4:
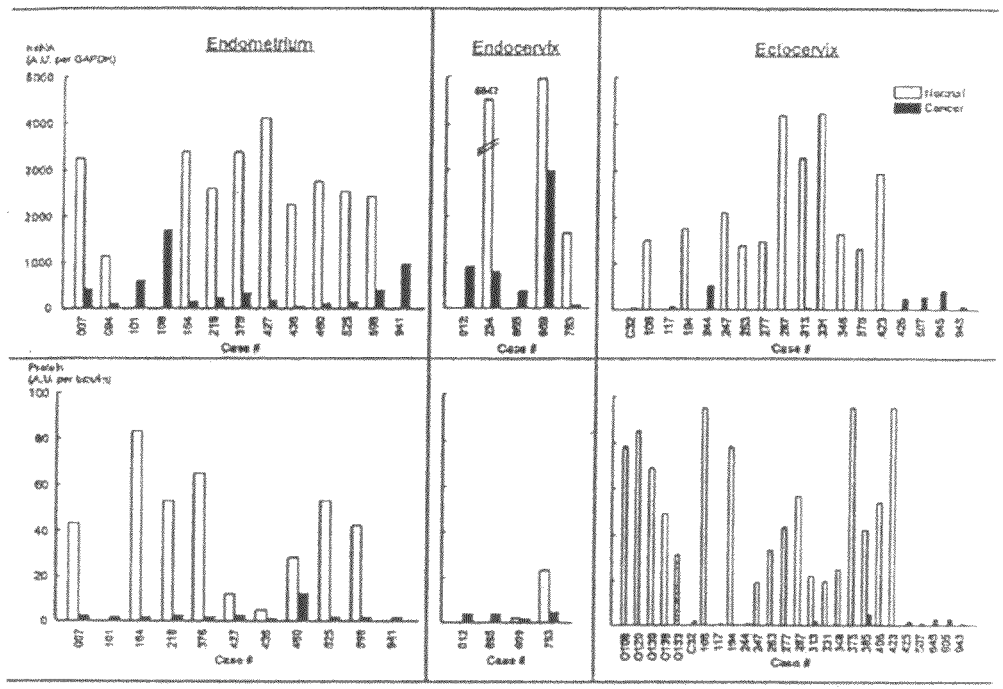

FIG. 4 illustrates one embodiment of a case-based analysis of tissue expression of $P2X_7$ mRNA (top) and $P2X_7$ protein (bottom). Endometrial, endocervical, and ectocervical tissues were obtained from the women identified with the designated codes. In some cases, normal (white columns) and cancer (cross-hatched columns) tissues were obtained from the same woman. $P2X_7$ mRNA levels in each tissue were normalized to glyceraldehyde-3-phosphate dehydrogenase (GAPDH) mRNA (determined by real-time PCR). $P2X_7$ protein levels were normalized to tubulin protein levels (determined by densitometry of the 65-85-kDa complex of the Western blots). AU=arbitrary units.

Figure 5:
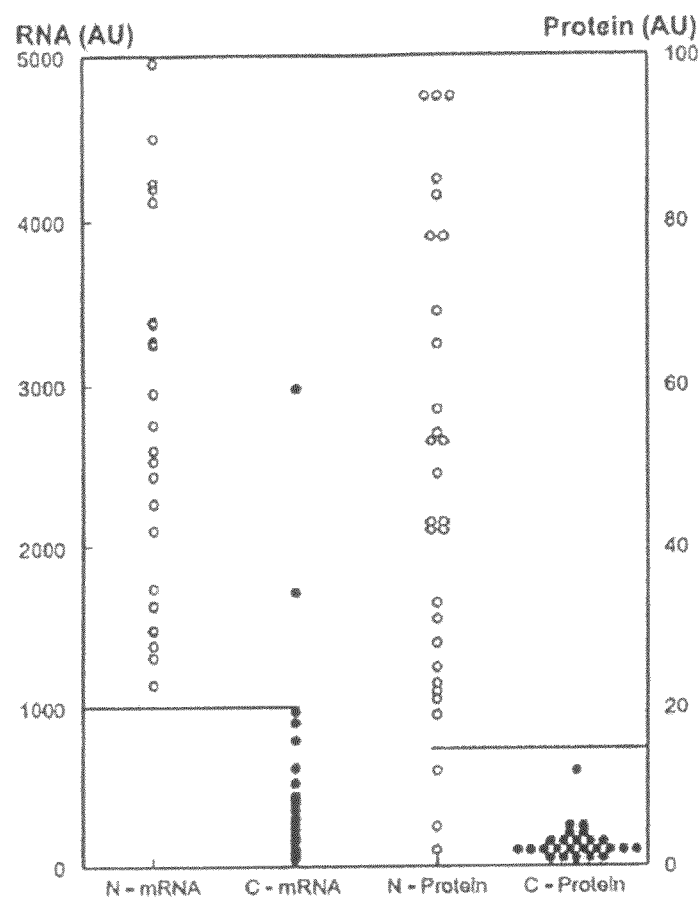

FIG. 5 presents a summary of the analysis presented in FIG. 4. Individual $P2X_7$ results for each tissue were grouped to normal (N: Open circles) or cancer (C: Crossed circles) for both mRNA and protein levels. The chosen cutoff points (horizontal lines) were as follows: positive detection of $P2X_7$ mRNA, ≥1,000; positive detection of $P2X_7$ protein, ≥15.

Figure 6:
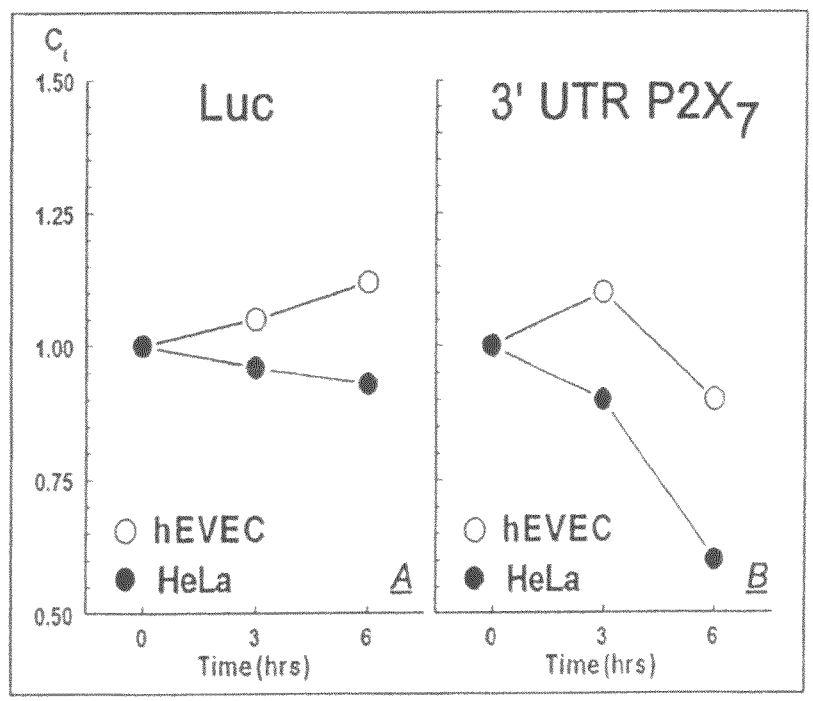

FIG. 6 presents exemplary data showing steady-state levels of luciferase mRNA in normal human ectocervical-vaginal epithelial cells (hEVEC, ○) and in cancer human cervical epithelial cells (HeLa, ●) transfected with either the luciferase reporter vector (Luc) or with the 3'UTR-$P2X_7$—luciferase vector. (means of two experiments)

Figure 7:
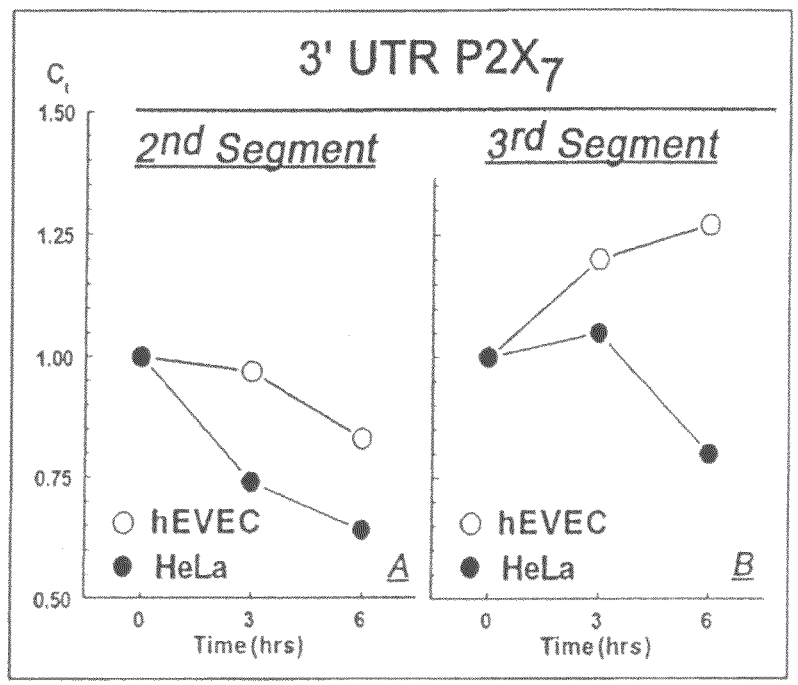

FIG. 7 presents exemplary data showing steady-state levels of luciferase mRNA in normal human ectocervical-vaginal epithelial cells (hEVEC, ○) and in cancer human cervical epithelial cells (HeLa, ●) transfected with either an miR-186 complementary segment or an miR-150 complementary segment of a 3'UTR-$P2X_7$ vector.

Figure 8:
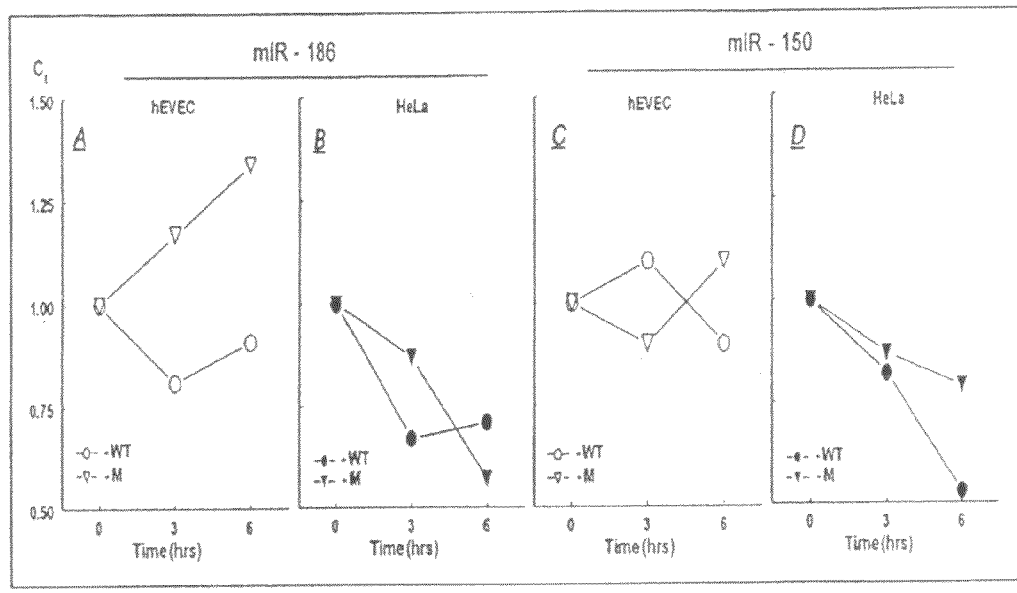

FIG. 8 presents exemplary data showing steady-state levels of luciferase mRNA in normal human ectocervical-vaginal epithelial cells (hEVEC, open symbols) and in cancer human cervical epithelial cells (HeLa, filled symbols) transfected with either an miR-186 complementary segment or a miR-150 complementary segment putative wild-type (WT, circles) or mutated (M, triangles) 3'UTR-$P2X_7$ vector.

Figure 9:
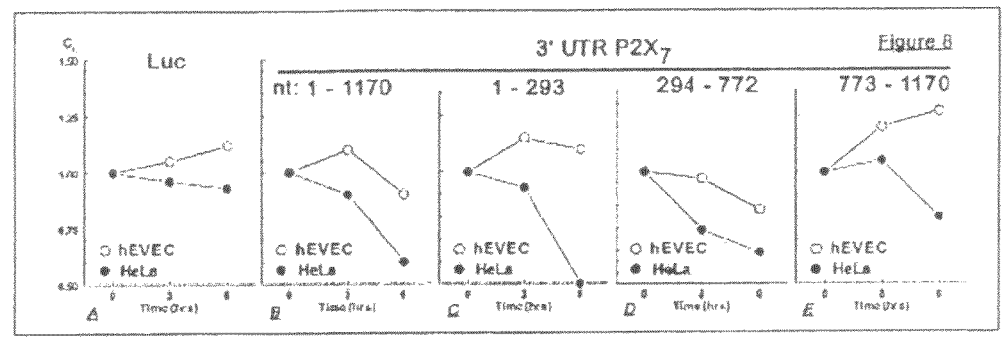

FIG. 9 presents an integrated graph of exemplary data showing steady-state levels of luciferase mRNA in in normal human ectocervical-vaginal epithelial cells (hEVEC, open symbols) and in cancer human cervical epithelial cells (HeLa, filled symbols) transfected with either an miR-186 complementary segment or a miR-150 complementary segment putative wild-type (WT, circles) or mutated (M, triangles) 3'UTR-$P2X_7$ vector.

Figure 10:
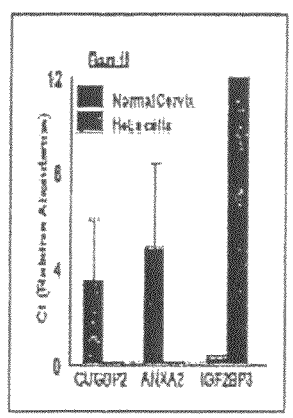

FIG. 10 presents exemplary data showing higher levels of RNA binding protein in cancer cells.

DETAILED DESCRIPTION

The present invention is related to the field of ribonucleic acid (RNA) regulation of pathophysiological states. In one embodiment, microRNAs (miRNAs) are involved in regulating pathophysiological conditions. In another embodiment, RNA Binding Proteins (RPBs) are involved in regulating pathophysiological conditions. In particular, RNAs may be used to screen, diagnose, treat, and/or provide prognoses for pathophysiologic conditions in either animals or plants. In one embodiment, an miRNA capable of hybridizing with a $P2X_7$ gene is selected from the group consisting of miR-150 and/or miR-186 and may be used to screen, diagnose, treat, and/or provide prognoses for uterine cancer.

I. The $P2X_7$ Gene

The $P2X_7$ is a member of the family of P2 nucleotide receptors and is an ATP-sensitive cation membrane-receptor channel. ATP, which is present normally in body extracellular fluids, is the naturally occurring ligand (activator), and activation of the $P2X_7$ receptor by extracellular ATP induces programmed cell death, apoptosis. $P2X_7$-mediated apoptosis is believed greater in normal than in cancer epithelial cells. Wang et al., "$P2X_7$-receptor mediated apoptosis of human cervical epithelial cells" *Am J. Physiol* 287:C1349-C1358 (2004); and Wang et al., "Anti-apototic effects of estrogen in normal and in cancer human cervical epithelial cells" *Endocrinology* 145:5568-5579 (2004). Since defective apoptosis may lead to cancer; the decreased cellular expression of $P2X_7$ could be one reason for the decreased apoptosis in cancer cells, and it could be causally related to the development of cancer.

Activation of the $P2X_7$ receptor protein by extracellular ATP stimulates formation of pores in the plasma membrane. Ralevic et al., "Receptors for purines and pyrimidines" *Pharmacol Rev* 50:413-492 (1998). Augmented influx of $Ca^{2+}$ via $P2X_7$-pores induces apoptosis mediated by the mitochondrial—caspase 9 pathway. Wang et al., "$P2X_7$-receptor mediated apoptosis of human cervical epithelial cells" *Am J Physiol* 287:C1349-1358 (2004); and Wang et al., "Anti-apoptotic effects of estrogen in normal and in cancer human cervical epithelial cells" *Endocrinology* 145:5568-5579 (2004). Therefore, decreased expression of $P2X_7$ protein activity in cancer cells may be one pathophysiological cellular mechanism involved in decreased apoptosis in cancer epithelial cells.

A. $P2X_7$ and Epithelial Cancer

Epithelia are tissues that line body surfaces. Epithelial cancers are common and usually display aggressive and fatal biological-clinical behavior. Although it is not necessary to understand the mechanism of an invention, it is believed that the present invention will lead to better understanding of how epithelial cancers develop. In one embodiment, the present invention contemplates a method for detecting cancers at early stage of development, consequently resulting in earlier treatment and improved survival rates. In one embodiment, the present invention contemplates methods of treating epithelial cancers. In one embodiment, the present invention contemplates methods of preventing epithelial cancers (i.e., for example, prophylactic treatments).

Levels of $P2X_7$ protein and $P2X_7$ messenger RNA ($P2X_7$ mRNA) are significantly reduced in cancer epithelial cells when compared to corresponding normal epithelial cells. These observations suggest that $P2X_7$ mRNA and $P2X_7$ protein could be used as biomarkers for pre-cancerous and cancerous conditions of epithelial tissues. Feng et al., "A truncated. $P2X_7$ receptor variant ($P2X_{7-j}$) endogenously expressed in cervical cancer cells antagonizes the full-length $P2X_7$ receptor through hetero-oligomerizaton" *J. Biol. Chem.* 281:17228-17237 (2006); and Li et al., "The $P2X_7$ receptor: A novel biomarker of uterine epithelial cancers. *Cancer Epidemiology Biomarkers and Prevention* 15:1906-1913 (2006): Human uterine epithelial cells express two $P2X_7$ isoforms: the full-length 85-65 kDa $P2X_7$ receptor ($P2X_7$), Wang et al., "EGF facilitates epinephrine inhibition of $P2X_7$-receptor mediated pore formation and apoptosis: a novel signaling network" *Endocrinology* 146:164-174 (2005); and an inactive 42 to 45-kDa truncated variant ($P2X_{7-j}$) that lacks the entire intracellular COOH terminus, the second transmembrane domain, and the distal third of the extracellular loop of the P2×7. Feng et al., "A truncated $P2X_7$ receptor variant ($P2X_{7-j}$) endogenously expressed in cervical cancer cells antagonizes the full-length $P2X_7$ receptor through hetero-oligomerization" *J Biol Chem* 281:17228-17237 (2006). The $P2X_{7-j}$ variant is deficient in ligand binding, pore formation, and mediation of apoptosis; however, it can interact and hetero-oligomerize with the full-length $P2X_7$. Because $P2X_7$ receptor functions depend on oligomerization of $P2X_7$ molecules into homotrimers, any interaction between the $P2X_{7-j}$ and the full-length $P2X_7$ can block $P2X_7$-mediated channel activity, pore formation, and induction of apoptosis.

Earlier studies showed that baseline and ligand-induced $P2X_7$-mediated apoptosis is greater in normal human ectocervical epithelial cells than in cancer human cervical cells. Wang et al., "$P2X_7$-receptor mediated apoptosis of human cervical epithelial cells" *Am J Physiol* 287:C1349-C1358 (2004). More recent results showed that normal and cancer human cervical cells express the variant $P2X_{7-j}$ but normal cells express higher levels of the full-length $P2X_7$ than cancer cells (i.e., cancer cells express similar levels of $P2X_{7-j}$ and $P2X_7$ proteins). Feng et al., "A truncated $P2X_7$ receptor variant ($P2X_{7-j}$) endogenously expressed in cervical cancer cells antagonizes the full-length $P2X_7$ receptor through hetero-oligomerization" *J Biol Chem* 281:17228-17237 (2006). These data provide a possible mechanistic explanation for the finding of lesser degree of $P2X_7$-mediated apoptosis in cancer cervical cells. Accordingly, normal cells that might express predominantly the $P2X_7$ isoform are more likely to form active $[(P2X_7)_3]$ homotrimers. In contrast, cancer cells that might express low levels of the $P2X_7$ isoform are more likely to form inactive heterotrimers, such as the $[(P2X_7)_2]/[(P2X_{7-j})]$ or the $[(P2X_7)]/[(P2X_{7-j})_2]$ or the inactive $[(P2X_{7-j})_3]$ homotrimers. Although it is not necessary to understand the mechanism of an invention, it is believed that the higher levels of $P2X_{7-j}$ in cancer cells prevent formation of an active $(P2X_7)_3$ homotrimer that is responsible for $Ca^{2+}$-activated apoptosis.

In one embodiment, the present invention contemplates the clinical significance of $P2X_7$ receptor expression in vivo in normal and cancer human uterine tissues. In one embodiment, the clinical significance comprises screening for human uterine cancer. In one embodiment, the clinical significance comprises diagnosing human uterine cancer. In one embodiment, the clinical significance comprises treating human uterine cancer. In one embodiment, the clinical significance comprises monitoring human uterine cancer. Using semiquantitative analyses, the levels of $P2X_7$ receptor mRNA and $P2X_7$ protein in tissues obtained from women with ectocervical, endocervical, and endometrial cancers are significantly lower than from the corresponding normal tissues. (infra).

1. $P2X_7$ and $P2X_{7-j}$ Expression $P2X_7$ expression in normal and cancer endometrial and cervical tissues was determined in terms of immunoreactivities with a anti-$P2X_7$ antibody that could be blocked by coincubation with a P2X$_7$ antigen. Specific P2X$_7$ immunoreactivities of a full-length P2X$_7$ protein (65-85 kDa) and of a truncated P2X$_{7-j}$ isoform protein (42-45 kDa) demonstrate their presence in uterine tissues. See, FIG. 1A. A loss of immunoreactivity with an anti-P2X$_7$ antibody are observed in samples coincubated with a P2X$_7$ antigen. See, FIG. 1B. Protein and mRNA levels of the truncated P2X$_{7-j}$ isoform demonstrated similar results from lysates of histologically normal, and cancerous endometrial or ectocervical tissues. Full-length P2X$_7$ protein and mRNA levels were significantly higher in histologically normal versus cancerous tissues. See, FIGS. 1A and 1C.

a. Normal Tissues

In normal uteri, P2X$_7$ immunoreactivity was localized predominantly in the endometrial, endocervical, and ectocervical epithelia as correlated and confirmed by costaining with the epithelial marker E-cadherin. See, FIG. 2; a-f, o-r, and w-zh. In all three types of epithelia, P2X$_7$ staining was observed both in membrane and cytoplasmic areas of epithelial cells. See, FIG. 2; c, q, and zg. In the endometrium and endocervix, the P2X$_7$ antibody stained the endometrial glands (See, FIG. 2; a-f) and the endocervical crypts (See, FIG. 2; o-r and w-z), respectively. P2X$_7$ staining was uniform in endometrial tissues of women ages <50 (See, FIG. 2; a-d); in women ages >51 (See, FIG. 2; e and f; age 67); in endocervical tissues of women ages <50 (See, FIG. 2; o-r and w-z); and in women ages >51 (data not shown).

Figure 2:
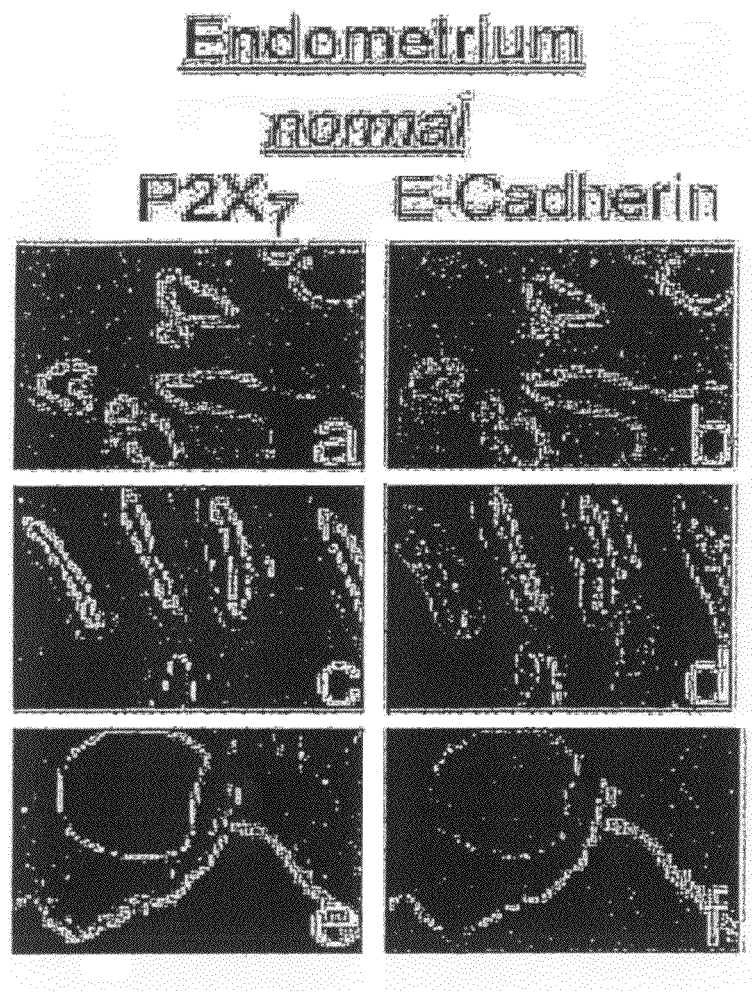
FIG. 2 presents exemplary data showing immunostaining with anti-$P2X_7$ antibody or anti-E-cadherin antibody of: i) endometrial tissues (a-n); ii) endocervical tissues (o-zb); and iii) ectocervical tissues (w-zv). Normal endometrial tissues (a-f); Normal endocervical tissues (o-r & w-zb; y arrowhead indicates a columnar-squamometaplasitc junction. za arrowhead indicates a squamometaplastic-squamous junction); Normal ectocervical tissues (zc-zh); Dysplasia ectocervical tissues (zi-zr; mild, moderate, & severe). Adenocarcinoma endometrial tissues (g-j); Mixed normal/adenometrial tissues (k-n); Adenocarcinoma endocervical tissues (s-v); Squamous cell carcinoma ectocervical tissues (zs-zv). Age ranges 35-47: a-d; o-r; and zi-zr. Age ranges 55-67: e, f, w-zb, zg, zh, and zs-zt. The experiments were repeated two to four times with similar trends. Magnification, x4 to x20.
Figure 2:
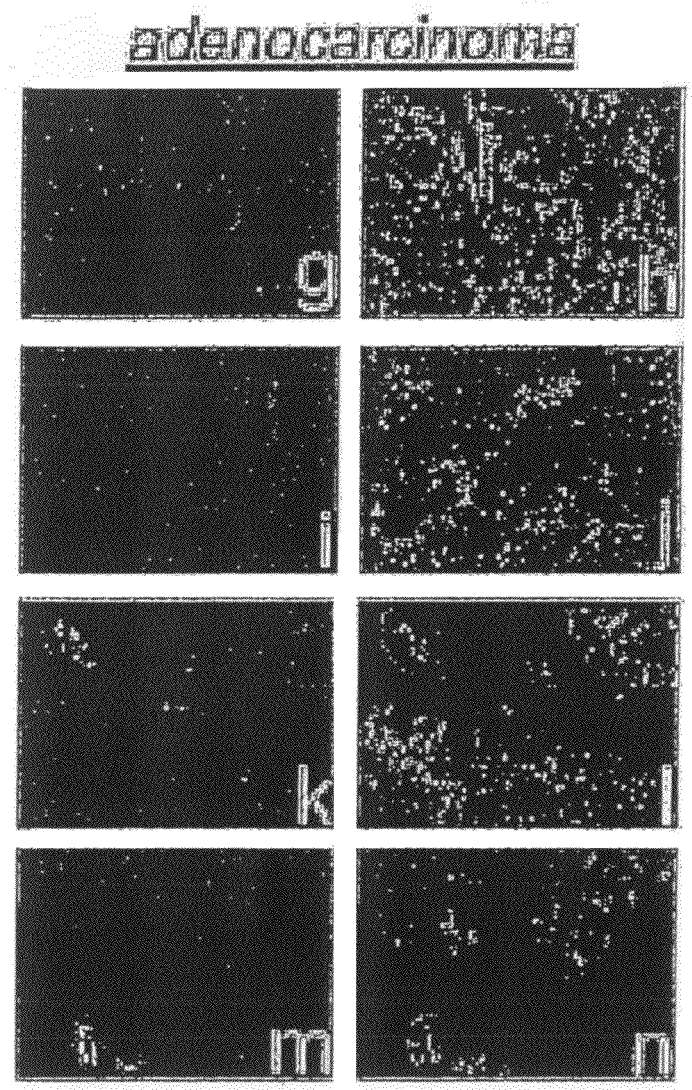
Figure 2:
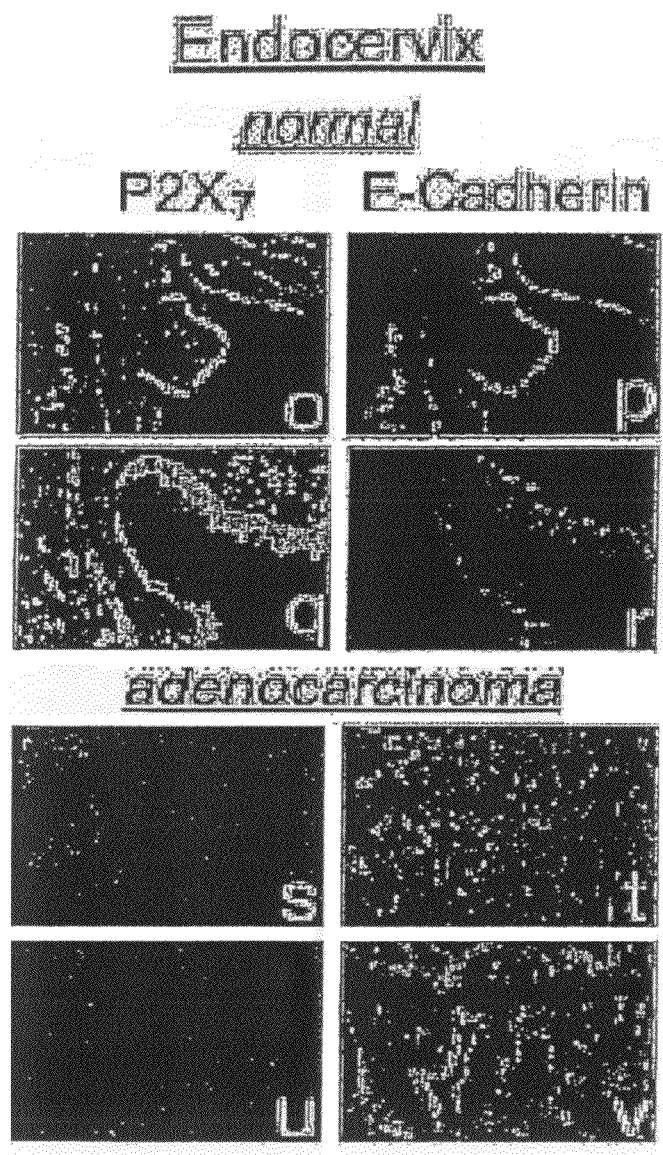
Figure 2:
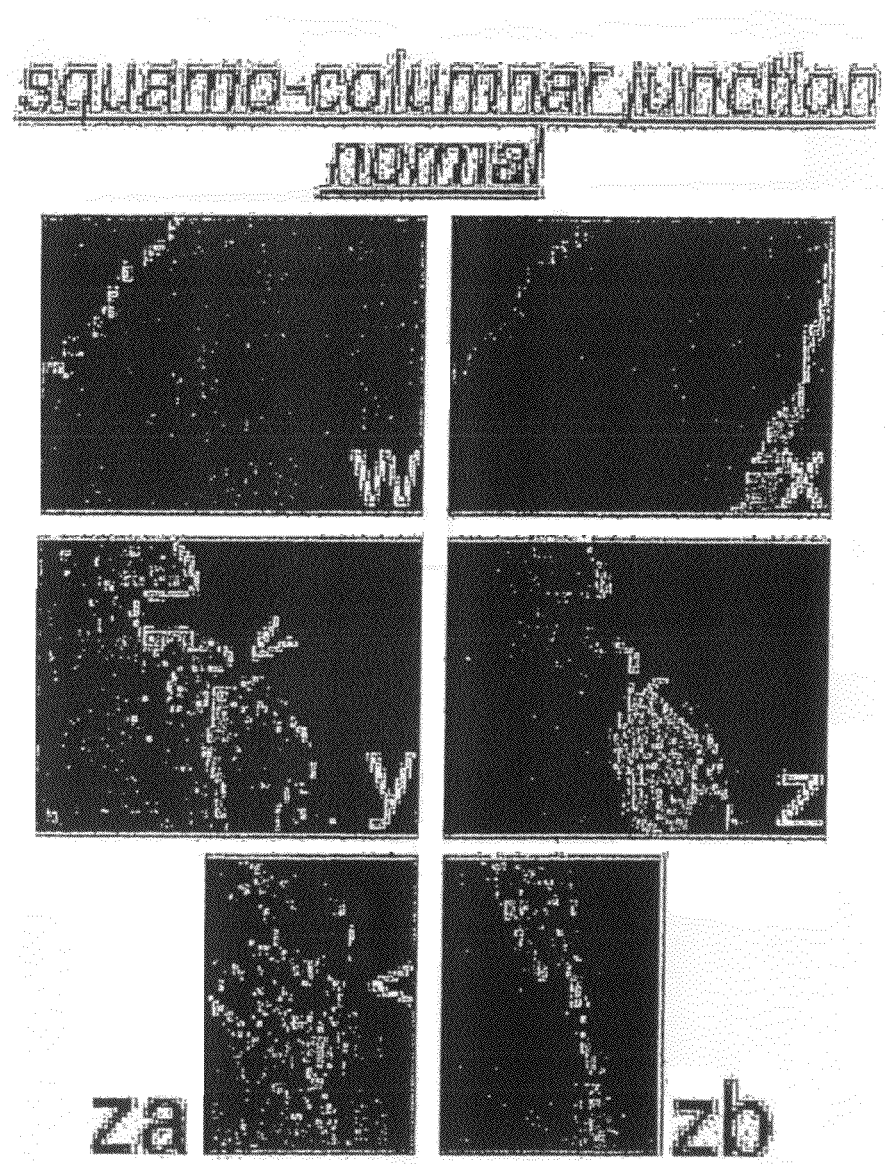
Figure 2:
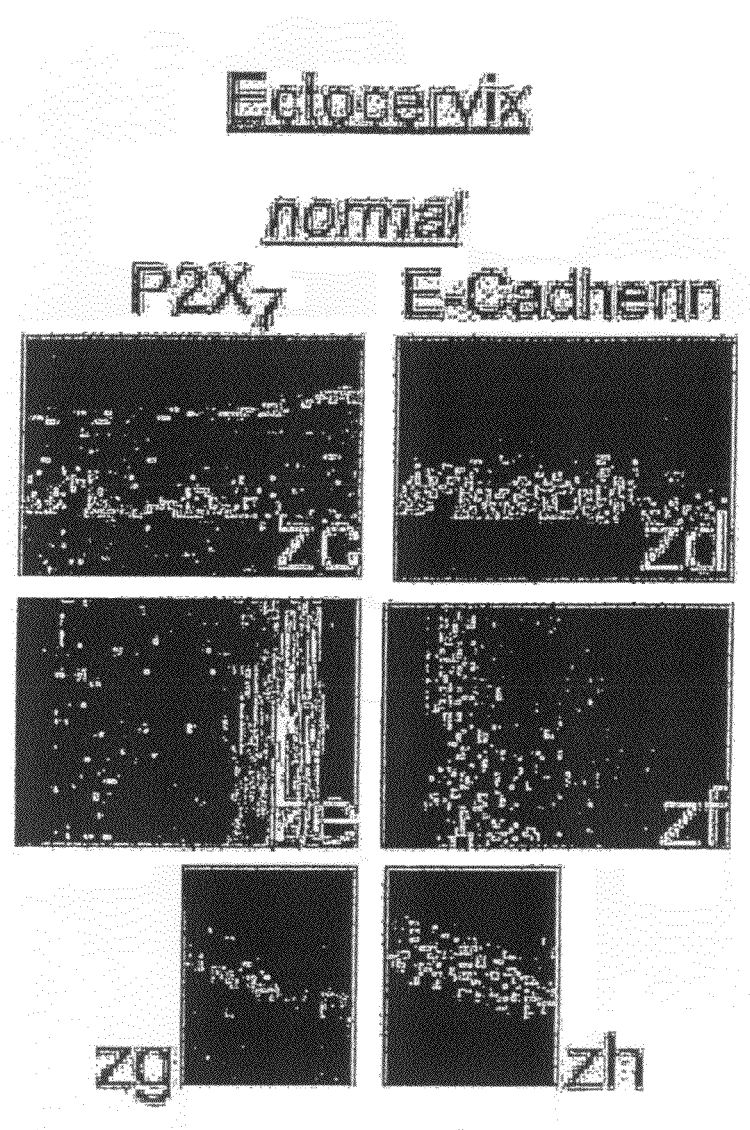
Figure 2:
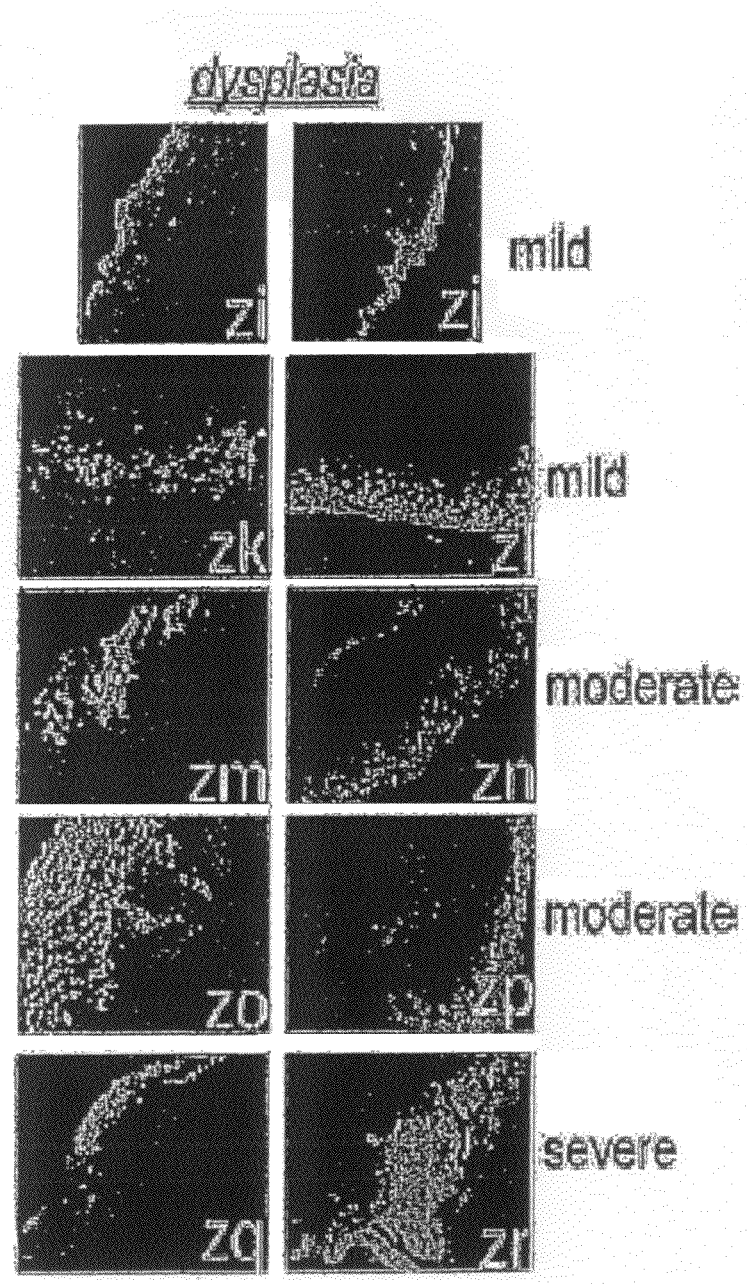
Figure 2:
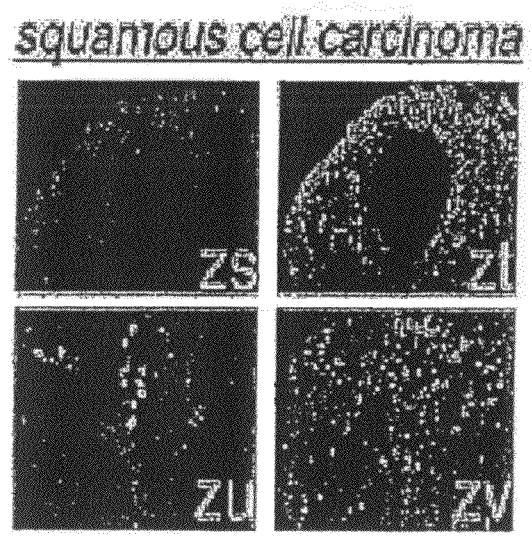

In normal uteri, strong P2X$_7$ staining was found at the transition zones of the columnar-endocervical and ectocervical-squamometaplastic epithelia (See, FIG. 2, y and z) and of the ectocervical squamometaplastic-squamous epithelia (See, FIG. 2; za and zb). In the normal ectocervix, P2X$_7$ staining was found predominantly in the epithelium, although some staining was also found in subepithelial tissues. See, FIG. 2; w-zb. In the ectocervical epithelium, P2X$_7$ staining was most abundant in the germinative (basal and parabasal) layers, both in tissues of women ages <50 (See, FIG. 2, zc-zf) and in women ages >51. See, FIG. 2; zg and zh. P2X$_7$ expression was diminished in suprabasal layers of the epithelium (See, FIG. 2; zc-zf), but enhanced expression was seen again in superficial layers (See, FIG. 2; zc-zf). Although it is not necessary to understand the mechanism of an invention, it is believed that this secondary expression probably results from trapped receptor in the superficial compact cells, also referred to as cornified envelopes. Gorodeski et al., "Retinoids, sex steroids, and glucocorticoids regulate ectocervical cell envelope formation but not the level of the envelope precursor, involucrin" *Differentiation* 42:75-80 (1989); See, FIG. 2; ze & zf showing hyperkeratosis. These observations are supported by results of in situ hybridization experiments where P2X$_7$ mRNA was found predominantly in the germinative layers of the ectocervical epithelium. See, FIG. 3; t and u.

b. Uterine Cancer Tissues

Uterine tissues comprising endometrial, endocervical, and ectocervical cancers lacked P2X$_7$ antibody staining. See, FIG. 2; g-n, s-v, and zs-zv, respectively. The endogenous positive controls were sections comprising a mix of endometrial cancer tissues and normal gland tissues in the same slice. See, FIG. 2; k-n. In those cases, the anti-P2X$_7$ antibody stained positively the normal gland tissues but did not stain the cancer tissues. Specifically, in sections containing normal endometrial glands plus endometrial cancer, the anti-P2X$_7$ antibody stained the normal glands (k: four glands in the middle; m: two glands at the left bottom corner) but not the adjacent cancerous tissues.

Analysis of tissues with different grades of ectocervical dysplasia showed that dysplastic lesions per se lacked P2X$_7$ staining. See, FIG. 2; zi-zr. In addition, when the cross-section was evaluated in its entirety, there was a gradual decrease in staining as the degree of abnormality progressed. Thus, in mild dysplasia, about one third of the epithelium in the basal side lacked P2X$_7$ staining. See, FIG. 2; zi-zl. In moderate dysplasia, about one half of the epithelium extending from the basal side lacked P2X$_7$ staining and pockets lacking staining could be seen projecting more superficially. See, FIG. 2; zm-zp. This was in contrast to the rather uniform graded staining in normal ectocervical epithelium. See, FIG. 2; zc. In severe dysplasia, about two thirds of the epithelium extending from the basal side lacked P2X$_7$ staining, and staining was observed only in the most superficial layer composed of superficial cells and envelopes. See, FIG. 2, zq and zr. Some cases of severe dysplasia lacked P2X$_7$ staining entirely (data not shown), similar to cases of cervical squamous cell carcinoma. See, FIG. 2; zs and zu.

Collectively, the data in FIG. 2 indicate that: (a) P2X$_7$ is expressed predominantly in the epithelial components of the uterus; (b) uterine epithelial cancerous lesions lack expression of P2X$_7$; and (c) in ectocervical dysplasia the dysplastic cells lacked P2X$_7$ staining and the total P2X$_7$ staining across the epithelium correlated reciprocally with the severity of the dysplasia.

2. P2X$_7$ mRNA Expression: In Situ Hybridization

The technique of in situ hybridization was used to determine the cellular distribution of P2X$_7$ mRNA in normal and cancer uterine tissues according to Example 2. The experiments focused on the expression of full-length P2X$_7$ using a cDNA template (probe) designed to hybridize specifically with full-length P2X$_7$. The sensitivity of the method was tested using human keratinocytes, which express endogenously a full-length P2X$_7$. No staining was obtained with an anti-digoxigenin antibody in cell preparations whether or not exposed to a sense P2X$_7$ probe. See, FIGS. 3A versus 3B. In contrast, hybridization with an antisense P2X$_7$ probe elicited significant perinuclear and cytoplasmic staining. See, FIGS. 3C versus 3A and/or 3B.

The specificity of the P2X$_7$ probe to distinguish P2X$_7$ and P2X$_{7-j}$ mRNA in situ was tested using Madin-Darby canine kidney cells that lack endogenous expression of the receptor. Madin-Darby canine kidney cells expressing a tetracycline repressor regulating system (to prevent potential toxic effects) were transfected with either P2X$_7$ or P2X$_{7-j}$ cDNAs. Cells were grown in the presence or absence of doxycyline which induces expression of P2X$_7$ and/or P2X$_{7-j}$ proteins. Feng et al., "A truncated P2X$_7$ receptor variant (P2X$_{7-j}$) endogenously expressed in cervical cancer cells antagonizes the full-length P2X$_7$ receptor through hetero-oligomerization" *J Biol Chem* 281:17228-17237 (2006). Cell preparations were hybridized either with a sense or with an antisense P2X$_7$ probe. Specific hybridization of a P2X$_7$ probe was seen only in doxycyline-treated cells transfected with the P2X$_7$ cDNA and hybridized with an antisense P2X$_7$ probe. See, FIGS. 3 *d-k*. Collectively, the results in FIG. 3 (*a-k*) validate the usefulness of the P2X$_7$ cDNA template for detection of a full-length P2X$_7$ mRNA using the in situ hybridization technique.

Figure 3:
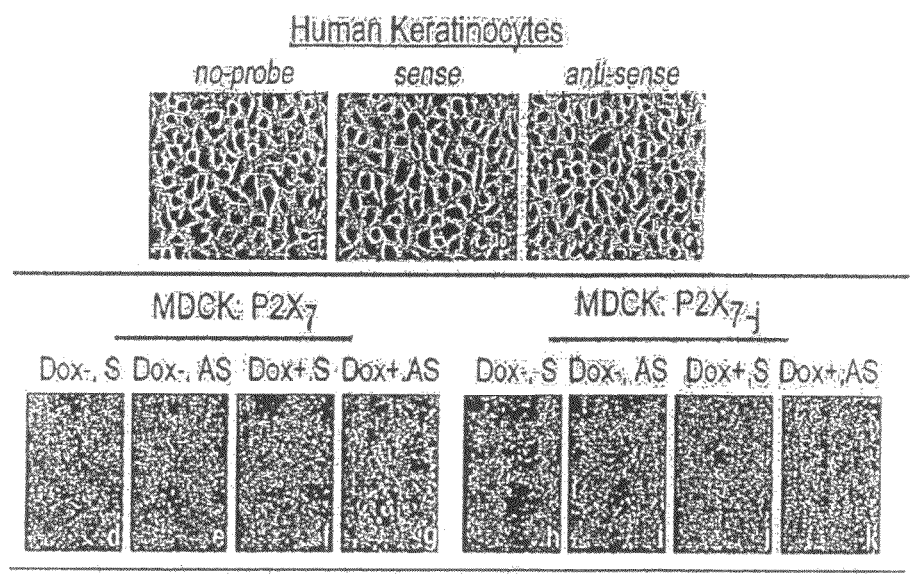
FIG. 3 presents exemplary data showing expression of $P2X_7$ mRNA using in situ hybridization performed according to Example 2.
Figure 3:
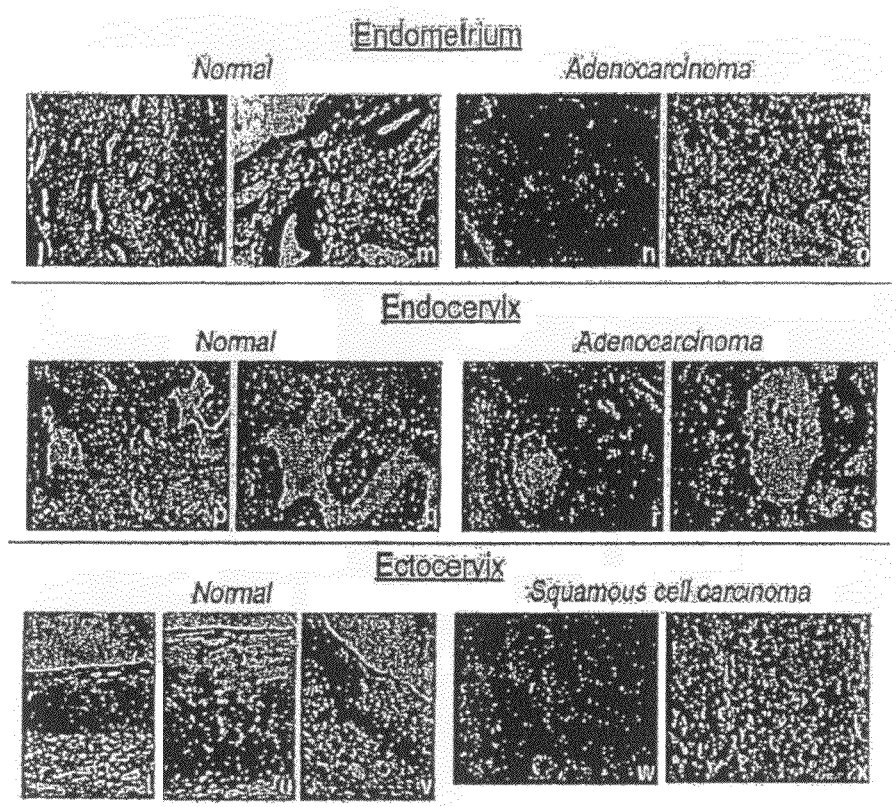

In cross-sections of human normal uterine tissues, specific intense perinuclear and cytoplasmic P2X$_7$ mRNA staining decorated the epithelial components of: i) endometrial glands, FIGS. 3 *i* and *m*; ii) endocervical crypts, FIGS. 3 *p* and *q*; and iii) ectocervix, FIGS. 3 *t* and *u*. The subepithelial regions of these tissues stained significantly less.

In cross-sections of human cancerous uterine tissues, no P2X$_7$ mRNA staining was found. See, FIGS. 3 *n, o, r, s, w*, and *x*. Although it is not necessary to understand the mechanism of an invention, it is believed that these data demonstrate that epithelial uterine cancer cells express minimal amounts of full-length $P2X_7$ mRNA (and concomitantly, minimal $P2X_7$ protein).

3. Quantification of $P2X_7$ Expression in Normal and Cancer Uterine Tissues

The data presented in FIG. 3 was then used to perform a semiquantitative analysis. See, FIG. 4. Full-length $P2X_7$ mRNA levels (top) and protein levels (bottom) in normal (white columns) and cancer uterine tissues (black columns) are illustrated. $P2X_7$ mRNA expression was determined in terms of $P2X_7$ mRNA quantitative PCR levels normalized in each tissue to the constitutive glyceraldehyde-3-phosphate dehydrogenase. See, FIG. 1C.

$P2X_7$ protein levels were determined in accordance with Example 3 by densitometry of the $P2X_7$ 65-85 kDa band normalized in each tissue to a constitutive tubulin. See, FIG. 1A. Included in the analysis for $P2X_7$ mRNA were a total of 50 tissues from 36 women, and in the analysis for $P2X_7$ protein a total of 54 tissues from 41 women. The semiquantitative analysis shows that $P2X_7$ mRNA and protein levels were higher in normal endometrial, normal endocervical, and normal ectocervical tissues when compared to cancerous endometrial, cancerous endocervical, and cancerous ectocervical tissues. Where normal and cancer tissues were obtained from the same woman, $P2X_7$ mRNA and protein levels were higher in the normal tissues versus cancer tissues. See, FIG. 4.

FIG. 5 summarizes the above semiquantitative analysis and groups the $P2X_7$ mRNA and protein results. Cutoff levels (horizontal lines) for both $P2X_7$ mRNA and protein were defined as those separating normal tissue levels (i.e., 'positive detection'; open circles) from cancerous tissue levels ("negative detection"; crossed circles). The cutoff values (arbitrary units—AU) were established as ≥1000 for $P2X_7$ mRNA and >15 for $P2X_7$ protein. The data of the 'positive detection' and 'negative detection' for $P2X_7$ mRNA and/or $P2X_7$ protein levels grouped by these categories were evaluated using $\chi^2$ analysis. See, Table 1.

TABLE 1

Chi Square Analysis Of Semiquantitative Data Analysis (See, FIG. 5)

| A. $P2X_7$ | Cancer | Normal | Total |
|---|---|---|---|
| mRNA | | | |
| Positive | $24^{TP}$ | $0^{FP}$ | 24 |
| Negative | $2^{FN}$ | $24^{TN}$ | 26 |
| Total | 26 | 25 | 50 |
| Protein | | | |
| Positive | $25^{TP}$ | $3^{FP}$ | 28 |
| Negative | $0^{FN}$ | $26^{TN}$ | 26 |
| Total | 25 | 29 | 54 |

| B. $P2X_7$ | RNA | Protein |
|---|---|---|
| Sensitivity | (24/26) 92% | (25/25) 100% |
| Specificity | (24/24) 100% | (26/29) 90% |
| Positive predictive value | (24/24) 100% | (25/28) 89% |
| Negative predictive value | (24/26) 92% | (26/26) 100% |
| False-positive ratio | (0/24) 0 | (3/28) 11% |
| False-negative ratio | (2/26) 8% | (0/26) 0 |

TABLE 1-continued

Chi Square Analysis Of Semiquantitative Data Analysis (See, FIG. 5)

| Likelihood ratio* | [92/(100 − 100)] = ∞ | [100/(100 − 90)] = 10 |
|---|---|---|
| 95% confidence interval | 3.43-49.25 | −∞ to +∞ |
| $\chi^2$ (Fisher's exact test) | P < 0.0001 | P < 0.0001 |

Abbreviations:
TP, true positive;
FP, false positive;
FN, false negative;
TN, true negative.
*Likelihood of having normal tissue if the test is positive.

The results indicate that the variables of $P2X_7$ mRNA and $P2X_7$ protein were sensitive (92% and 100%, respectively) and specific (100% and 90%, respectively) in differentiating normal and cancer uterine tissues. This analysis was not affected by the age, race, and ethnic origin of the woman or by the type, stage, or grade of the cancer (data not shown).

In summary, the above data indicate that full-length $P2X_7$ levels are lower in uterine epithelial cancer tissues than in corresponding normal tissues. In one embodiment, the present invention contemplates that tissue analysis of $P2X_7$ mRNA and protein levels could be used as a novel biomarker to differentiate normal and cancer uterine epithelial tissues. Because the results were similar regardless of tumor type (i.e., for example, adenocarcinomas, squamous cell carcinomas), it is possible that the differences in the expression of $P2X_7$ in normal versus cancer tissues are not limited to uterine tissues and that similar effects occur also in other types of epithelial neoplasia. For example, observations have already been made showing similar results in skin, breast, and prostrate tissues (data not shown). The present invention, also contemplates that $P2X_7$ mRNA and/or $P2X_7$ protein tissue levels may also be a biomarker for all epithelial neoplasias including, but not limited to, skin, breast, or prostate neoplasias.

4. Regulation of $P2X_7$ mRNA

It is generally believed that proteins are produced (translated) from mRNA. In epithelial tissues, it has been shown that there is a good correlation between $P2X_7$ protein and $P2X_7$ mRNA levels. Li et al., "The $P2X_7$ Receptor: A novel biomarker of uterine epithelial cancers" *Cancer Epidemiology Biomarkers and Prevention* 15:1-8 (2006). Therefore, low levels of $P2X_7$ protein in cancer cells might be a result of low expression of $P2X_7$ mRNA. Together, these observations indicate that a reduced $P2X_7$ protein expression and reduced $P2X_7$ mRNA levels in cancer cells as compared to normal epithelial cells might result from altered $P2X_7$ pre-translational control.

The human $P2X_7$ receptor gene has been suggested to be localized to chromosome 12q24 comprising 13 exons. Buell et al., "Gene structure and chromosomal localization of the human P2X7 receptor" *Receptors Channels* 5:347-354 (1998). Contrary to observed reduced $P2X_7$ mRNA concentrations in cancer cells, $P2X_{7-j}$ mRNA levels are similar in normal and cancer epithelial cells. Feng et al., "A truncated P2X7 receptor variant ($P2X_{7-j}$) endogenously expressed in cervical cancer cells antagonizes the full-length $P2X_7$ receptor through hetero-oligomerization" *J Biol Chem* 281:17228-17237 (2006). Although it is not necessary to understand the mechanism of an invention, it is believed that since the $P2X_7$ and $P2X_{7-j}$ mRNAs share the same promoter, it is unlikely that a low expression of full-length $P2X_7$ in cancer cells is the result of decreased transcription mediated through the 5' untranslated region (5'UTR) (i.e., for example, the promoter region of the gene). It is further believed that the $P2X_7$ and P2X$_{7-j}$ mRNA have different 3' untranslated regions (3'UTRs), a region often suggested to maintain mRNA stability. Mitchell et al., "mRNA turnover" *Curr Opin Biol* 13:320-325 (2001); and Guhaniyogi et al., "Regulation of mRNA stability in mammalian cells" *Gene* 265:11-23 (2001). In one embodiment, the present invention contemplates a P2X$_7$ 3'UTR comprising at least one region conferring instability to a P2X$_7$ mRNA transcript, wherein the P2X$_7$ mRNA is degraded at a faster rate in cancer cells than in normal epithelial cells. In another embodiment, the present invention contemplates a P2X$_7$ 3'UTR comprising at least one region conferring stability to a P2X$_7$ mRNA transcript, wherein a P2X$_7$ mRNA produced in normal epithelial cells is more stable than a P2X$_7$ mRNA produced in cancer epithelial cells. Although it is not necessary to understand the mechanism of an invention, it is believed that one of the mechanisms by which cancer cells control the expression of the P2X$_7$ tRNA is through faster degradation of a 3'UTR-P2X$_7$.

II. MicroRNAs

MicroRNAs (miRNAs) were previously referred to as small temporal RNAs (stRNAs) belonged to a class of noncoding microRNAs, which have been shown to control gene expression either by repressing translation or by degrading targeted mRNAs. Couzin J, *Science* 298:2296-2297 (2002). It is believed that about 400 different microRNAs (miRNAs) are encoded in the human genome. Cellular microRNAs (miRNAs) are a class of single-stranded RNA molecules that are expressed in cells from plants to animals. Bartel, D. P. "mRNAs: genomics, biogenesis, mechanism, and function" *Cell,* 116:281-297 (2004). mRNAs are expressed as long precursor RNAs that get processed by cellular nucleases (i.e., for example, Drosha) before being transported by an Exportin-5-dependent mechanism into the cytoplasm. Yi et al., "Exportin-5 mediates the nuclear export of pre-microRNAs and short hairpin RNAs" *Genes Dev.,* 17, 3011-3016 (2003). Once in the cytoplasm miRNAs are cleaved further by an enzyme (i.e., for example, DICER) the resulting miRNAs might associate with a cellular complex that is at least similar to a RNA-induced silencing complex that participates in RNA interference. Hutvagner et al., "A miRNA in a multiple-turnover RNAi enzyme complex" *Science* 297:2056-2060 (2002).

A single-stranded miRNA cellular complex may provide intracellular transportation to mRNAs comprising sequences that are at least partially complementary to the miRNA. Doench et al., "Specificity of microRNA target selection in translational repression" *Genes Dev.* 18:504-511 (2004). Very few miRNAs, however, have known cellular functions. For example, miRNA, lin-4, was first identified in *Caenorhabditis elegans*. Research revealed that lin-4 accumulates during the first and second larval stages and triggers passage to the third larval stage by repressing the translation of at least two genes, lin-14 and lin-28. The activity of lin-4 depends on partial homology of a miRNA to specific regions of a 3'-untranslated region (3'-UTR) of the lin-14 and lin-28 mRNAs. Ambros, V., "miRNAs: tiny regulators with great potential" *Cell* 107:823-826 (2001); Lee et al., "The *C. elegans* heterochronic gene lin-4 encodes small RNAs with antisense complementarity to lin-14" *Cell* 75:843-854 (1993); and Wightman et al., "Posttranscriptional regulation of the heterochronic gene lin-14 by lin-4 mediates temporal pattern formation in *C. elegans*" *Cell,* 75, 855-862 (1993). A second exemplary miRNA, let-7, accumulates during *C. elegans* larval development and triggers passage from late larval to adult cell fates. Reinhart et al., "The 21-nucleotide let-7 RNA regulates developmental timing in *Caenorhabditis elegans*" *Nature* 403:901-906 (2000).

Currently, only a few mammalian miRNAs have been shown to have a defined role in a biological process. In one example, a mammalian miRNA (miR-181) was found to be specifically expressed and dynamically regulated in hematopoietic cells, and its expression in hematopoietic stem/progenitor cells increased the fraction of B-cells in both tissue culture and adult mice. Chen et al., "mRNAs modulate hematopoietic lineage differentiation" *Science* 303: 83-86 (2004).

miRNA targets have also been proposed to exist in plants. Llave et al., "Cleavage of Scarecrow-like mRNA targets directed by a class of *Arabidopsis* miRNA" *Science* 297: 2053-2056 (2002); Rhoades et al., "Prediction of plant microRNA targets" *Cell* 110:513-520 (2002); and Bartel et al., "MicroRNAs: At the Root of Plant Development" *Plant Physiol* 132:709-717 (2003). Two mouse miRNAs (miR-127 and miR-136) show perfect antisense complementarity with the coding region of a retrotransposon-like gene (Rtl1). Seitz et al., "Imprinted microRNA genes transcribed antisense to a reciprocally imprinted retrotransposon-like gene" *Nat Genet* 34:261-262 (2003). In particular, genetic dissection of the heterochronic gene pathway in *C. elegans* identified the lin-14 and lin-28 mRNAs as targets for the lin-4 miRNA. Lee et al., "The *C. elegans* heterochronic gene lin-4 encodes small RNAs with antisense complementarity to lin-14" *Cell* 75:843-854 (1993); Wightman et al., Post-transcriptional regulation of the heterochronic gene lin-14 by lin-4 mediates temporal pattern formation in *C. elegans*" *Cell* 75:855-862 (1993); and Moss et al., "The cold shock domain protein LIN-28 controls developmental timing in *C. elegans* and is regulated by the lin-4 RNA" *Cell* 88:637-646 (1997). Similarly, lin-41 mRNA has been identified as a target for the let-7 miRNA. Reinhart et al., "The 21-nucleotide let-7 RNA regulates developmental timing in *Caenorhabditis elegans*" *Nature* 403:901-906 (2000).

A. Synthetic or Recombinant miRNAs

Isolated and/or recombinant miRNA gene products can be obtained using a number of standard techniques. For example, the miRNA gene products can be chemically synthesized using one of several methods. In one method, miRNA gene products are chemically synthesized using appropriately protected ribonucleoside phosphoramidites and a conventional DNA/RNA synthesizer. Commercial suppliers of synthetic RNA molecules or synthesis reagents include, but are not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, miRNA gene products can be expressed from recombinant circular or linear DNA plasmids using any suitable promoter. Suitable promoters for expressing RNA from a plasmid include, but are not limited to, the U6 or H1 RNA pol III promoter sequences, or the cytomegalovirus promoters. Recombinant plasmids may further comprise inducible or regulatable promoters for expression of the miRNA gene products in cancer cells.

miRNA gene products that are expressed from recombinant plasmids can be isolated from cultured cell expression systems by standard techniques. miRNA gene products which are expressed from recombinant plasmids can also be delivered to, and expressed directly in, cancer cells.

miRNA gene products can be expressed from a separate recombinant plasmid, or can be expressed from the same recombinant plasmid. Preferably, miRNA gene products are expressed as RNA precursor molecules from a single plasmid, and precursor molecules are processed into a functional miRNA gene product by a suitable processing system, including processing systems extant within a cancer cell. Other suitable processing systems include, but are not limited to; i) the in vitro *Drosophila* cell lysate system (U.S. Patent Application Publ. No. 2002/0086356 To Tuschl et al.); or ii) the *E. coli* RNAse III system (U.S. Patent Application Publ No. 2004/0014113 to Yang et al.) (both applications herein incorporated by reference).

Selection of plasmids suitable for expressing miRNA gene products, methods for inserting nucleic acid sequences into a plasmid to express gene products, and methods of delivering a recombinant plasmid into cells of interest may be considered from numerous publications. See, for example, Zeng et al., *Molecular Cell* 9:1327-1333 (2002); Tuschl, *Nat. Biotechnol* 20:446-448 (2002); Brummelkamp et al., *Science* 296:550-553 (2002); Miyagishi et al., *Nat. Biotechnol.* 20:497-500 ((2002); Paddison et al., *Genes Dev.* 16:948-958 (2002); Lee et al., *Nat. Biotechnol.* 20:500-505 (2002); and Paul et al., *Nat. Biotechnol.* 20:505-508 (2002), the entire disclosures of which are herein incorporated by reference.

In one embodiment, a plasmid expressing an miRNA gene product (i.e., for example, miR-150 and/or miR-186 and complementary sequences thereof) comprises a sequence encoding a miRNA precursor RNA under the control of the CMV intermediate-early promoter. As used herein, "under the control" of a promoter means that the nucleic acid sequences encoding the miRNA gene product are located 3' of the promoter, so that the promoter can initiate transcription of the miRNA gene product coding sequences.

miRNA gene products can also be expressed from recombinant viral vectors. It is contemplated that the miRNA gene products can be expressed from two separate recombinant viral vectors, or from the same viral vector. The RNA expressed from the recombinant viral vectors can either be isolated from cultured cell expression systems by standard techniques, or can be expressed directly in cancer cells.

Recombinant viral vectors may comprise sequences encoding the miRNA gene products and any suitable promoter for expressing the RNA sequences. Suitable promoters include, for example, the U6 or H1 RNA pol III promoter sequences, or the cytomegalovirus promoters. Recombinant viral vectors can also comprise inducible or regulatable promoters for expression of the miRNA gene products in a cancer cell.

Any viral vector capable of accepting coding sequences for miRNA gene products (or complementary sequences thereof) can be used, including, but not limited to, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors can be pseudotyped with surface proteins including, but not limited to, those from vesicular stomatitis virus (VSV), rabies, Ebola, Mokola, and the like. AAV vectors can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes may also be performed. Rabinowitz et al., *J Virol* 76:791-801 (2002), the entire disclosure of which is herein incorporated by reference.

Recombinant viral vectors are suitable for use with methods for inserting nucleic acid sequences for expressing RNA into the vector, methods of delivering the viral vector to the cells of interest, and recovery of the expressed RNA products are available by using several methodologies. Dornburg, *Gene Therap.* 2:301-310 (1995); Eglitis, *Biotechniques* 6:608-614 (1988); Miller, *Hum. Gene Therap.* 1:5-14 (1990); and Anderson, *Nature* 392:25-30 (1998), the entire disclosures of which are herein incorporated by reference.

Some viral vectors are those derived from AV and AAV. Suitable AV vectors for expressing the miRNA gene products, a method for constructing the recombinant AV vectors, and a method for delivering the vectors into target cells are described. Xia et al. *Nat. Biotech.* 20:1006-1010 (2002); the entire disclosure of which is herein incorporated by reference. Suitable AAV vectors for expressing the miRNA gene products, methods for constructing the recombinant AAV vector, and methods for delivering the vectors into target cells are described. Samulski et al. *J. Virol.* 61:3096-3101 (1987); Fisher et al., *J. Viral.*, 70:520-532 (1996); Samulski et al., *J. Virol.* 63:3822-3826 (1989); U.S. Pat. No. 5,252,479; U.S. Pat. No. 5,139,941; International Patent Application No. WO 94/13788; and International Patent Application No. WO 93/24641, the entire disclosures of which are herein incorporated by reference. In one embodiment, miRNA gene products (i.e., for example, miR-150 and/or miR-186 and complementary sequences thereof) are expressed from a single recombinant AAV vector comprising the CMV intermediate early promoter. In one embodiment, a recombinant AAV viral vector of the invention comprises a nucleic acid sequence encoding an miRNA precursor RNA in operable connection with a polyT termination sequence under the control of a human U6 RNA promoter.

Transfection methods for eukaryotic cells include, but are not limited to, direct injection of the nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

For example, cells can be transfected with a liposomal transfer compound (i.e., for example, DOTAP (N-[1-(2,3-dioleoyloxy)propyl]-N,N,N-trimethyl-ammonium methylsulfate, Boehringer-Mannheim) or an equivalent, such as Lipofectin®. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$.

In one embodiment, RNA molecules, e.g., siRNAs or miRNAs, and/or RISC inactivators are synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the ss-siRNA, miRNA or RISC inactivator.

Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses an RNA silencing agent, e.g., ss-siRNA, from a recombinant construct may be produced by introducing the construct into a zygote, an embryonic stem cell, or another multipotent cell derived from the appropriate organism.

B. miRNAs As Biomarkers

Some miRNAs may represent biomarkers for pre-cancerous and cancerous states as well as biomarkers and prognostic indicators for other physiologic and pathophysiologic conditions. These miRNA biomarkers may identify disease processes leading to earlier treatment and/or prevention of diseases that are associated with defective apoptosis.

Although it is not necessary to understand the mechanism of an invention, it is believed that that cells might control steady state intracellular levels of pathophysiological biomarkers (i.e., for example, the $P2X_7$ mRNA cancer biomarker) by altering mRNA degradation rates. It is further believed that conditions having reduced intracellular mRNA biomarker concentrations might reflect a faster degradation rate. In one embodiment, the present invention contemplates that hybridization of an miRNA to a 3'-UTR mRNA region (i.e., for example, an instability site) activates mRNA degradation, thereby reducing intracellular mRNA levels. In another embodiment, the present invention contemplates a pathophysiologic cell comprising an elevated miRNA level (i.e., for example, detectable) as compared to a normal cell (i.e., for example, not detectable). In one embodiment, the pathophysiologic cell comprises a cancer cell.

Degradation of mRNA can be mediated by at least two mechanisms; i) cis-dependent trans-acting regulatory proteins; and ii) microRNAs (miRNA). In this context, cis refers to the target side (i.e., for example, a $P2X_7$ molecule), while trans refers to the side opposite the cis (i.e., for example, molecules that interact with $P2X_7$).

The former mechanism (i.e., for example, RNA regulatory proteins) has been previously elucidated. The second mechanism (i.e., for example, miRNA), however, is not fully understood. Currently, approximately 400 different miRNAs are thought responsible for regulating approximately 30-92% of human genes. Lewis et al., "Conserved seed pairing, often flanked by adenosines, indicates that thousands of human genes are microRNA targets" *Cell* 120:15-20 (2005). The role of miRNAs in differentiation, apoptosis, and cancer has been suggested but no clear generalized role has been established. For example, i) miR-15 and miR-16 are non-functional in cases of type-B chronic lymphocytic leukemia, Wang et al., "MicroRNA: past and present" *Front Biosci;* 12:2316-2329 (2007); ii) miR-143 and miR-145 were found to be downregulated in colonic adenocarcinoma samples compared with matched, normal tissues, Ambros V., "The functions of animal microRNAs" *Nature* 431:350-355 (2004); iii) the miR-155 precursor was found in children with Burkitt's Lymphoma, but not in patients with leukemia, Croce et al., "miRNAs, cancer, and stem cell division" *Cell* 122:6-7 (2005); iv) knockdown of the miRNA processing protein RNASEN in esophageal cancer cell lines resulted in a reduction in cell number, Bartel D P., "MicroRNAs: genomics, biogenesis, mechanism, and function" *Cell* 116:281-297 (2004); v) upregulation of miR-21, miR-155 and downregulation of miR-10b, miR-125b, and miR-145 was observed in breast cancer tissues, Wienholds et al., "mRNA function in animal development" *FEBS Lett.* 579:5911-5922 (2005); vi) overexpression of miR-125a or miR-125b in breast cancer cells suppressed ERBB2 and ERBB3 at both the transcript and protein level, Metzler et al., "High expression of precursor miRNA-155/BIC RNA in children with Burkitt lymphoma" *Genes Chromosomes Cancer* 2:167-169 (2004); and vii) inhibition of miR-150 decreased cell growth and increased apoptosis in Hela cells (32), suggesting that miR-150 blocks apoptosis. Sugito et al., "RNASEN Regulates cell proliferation and affects survival in esophageal cancer patients" *Clin Cancer Res* 12:OF1-OF7 (2006).

In one embodiment, the present invention contemplates an mRNA comprising a 3'-UTR region, wherein the 3'UTR has a nucleotide sequence complementary with at least a portion of an miRNA. In one embodiment, the 3'UTR comprises at least one instability region. In one embodiment, the miRNA comprises miR-150. In one embodiment, the miRNA comprises miR-186. In one embodiment, the miRNAs are approximately 5-100 nucleotides long. In one embodiment, miRNAs are approximately 15-50 nucleotides long. In one embodiment, miRNAs are approximately 18-25 nucleotides long.

Although it is not necessary to understand the mechanism of an invention, it is believed that miRNAs are regulatory RNAs that attach and hybridize with a homologous sequence on an mRNA 3'-UTR region. In one embodiment, the present invention contemplates a composition comprising an miRNA binding to a $P2X_7$ 3'UTR region. In one embodiment, the present invention contemplates a method comprising creating an miRNA/mRNA binding pair under conditions such that mRNA degradation is stimulated.

Computational methods have been reported that attempt to predict microRNA targets existing on mRNA oligonucleotides. The algorithms are suggested to be able to design and synthesize novel microRNAs. Hatzigeorgiou et al., "Method and Systems For Identifying Micro-RNA Targets And Synthesizing Novel Micro-RNAs And Uses Of the Same" United States Patent Appln Publ. No. 2007/0026403 (herein incorporated by reference in its entirety). Many miRNAs hybridize by base pairing with mRNA-recognition elements (MREs) found in their mRNA targets and direct either: i) target RNA endonucleolytic cleavage (Elbashir et al., "RNA interference is mediated by 21- and 22-nucleotide RNAs" *Genes Dev* 15:188-200 (2001); and Hutvagner et al., "A microRNA in a multiple-turnover RNAi enzyme complex" *Science* 297:2056-2060 (2002); or ii) translational repression (Olsen et al., "The lin-4 regulatory RNA controls developmental timing in *Caenorhabditis elegans* by blocking LIN-14 protein synthesis after the initiation of translation" *Dev Biol* 216:671-680 (1999); Seggerson et al., "Two genetic circuits repress the *Caenorhabditis elegans* heterochronic gene lin-28 after translation initiation" *Dev Biol* 243:213-225 (2002); Zeng et al., "Both natural and designed micro RNAs can inhibit the expression of cognate mRNAs when expressed in human cells" *Mol. Cell.* 9:1327-1333 (2002); and Doench et al., "siRNAs can function as miRNAs" *Genes Dev.* 17:438-442 (2003). Although it is not necessary to understand the mechanism of an invention, it is believed that the manner by which a miRNA or siRNA base pairs with its mRNA target correlates with its function: for example, if the complementarity between a mRNA and its target is extensive, the RNA target is cleaved; alternatively, if the complementarity is partial, the stability of the target mRNA is not affected but its translation is repressed. However, how general this correlation is and the factors and mechanisms that determine the function of any given miRNA are unknown.

C. miRNAs and Cancer

Some studies have suggested involvement of some miRNAs in cancer, but the information is limited and vague. Aberrant miRNA expression has been correlated with cancer, cancer-associated genomic regions, and fragile sites in chromosomes.

A 13q14 deletion constitutes the most frequent chromosomal abnormality in chronic lymphocytic leukemia (CLL), suggesting the involvement of one or more tumor suppressor genes at this locus. Current genetic analyses utilizing techniques including extensive loss of heterozygosity, mutation, and expression studies, has not yet provided a consistent involvement of any of the 13q14 genes with open reading frames (i.e., for example, miR-15 or miR-16). Calin et al., "Frequent deletions and down-regulation of miRNA genes miR-15 and miR-16 at 13q14 in chronic lymphocytic leukemia" *Proc. Nail Acad. Sci. USA* 99:15524-15529 (2002).

Studies of miRNA expression in colonic adenocarcinoma and normal mucosa identified potential links between miRNA expression/maturation and cancer. It was reported that out of 28 miRNAs identified in human colorectal mucosa, two (miR-143 and miR-145) were significantly down-regulated in 12 adenocarcinoma samples compared with matched, normal tissues. Michael et al., (2003) "Reduced accumulation of specific miRNAs in colorectal neoplasia" *Mol. Cancer. Res.* 1:882-891 (2003).

The human BIC RNA encodes miR-155 and is believed elevated in children with Burkitt lymphoma. Metzler et al., "High expression of precursor miRNA-155/BIC RNA in children with Burkitt lymphoma" *Genes Chromosomes Cancer* 2:167-169 (2004).

The chromosomal locations of 186 miRNA genes were mapped, over 52% of which are in cancer-associated genomic regions or in fragile sites. This study also found that several miRNAs located in deleted regions are expressed at low levels in cancer samples. Lewis et al., "Prediction of mammalian miRNA targets" *Cell* 115:787-798 (2003).

In HeLa cells the inhibition of miRNA-150 decreased cell growth and increased apoptosis, suggesting that miRNA-150 blocks apoptosis thereby promoting cellular proliferation. Cheng et al., "Antisense inhibition of human mRNAs and indications for an involvement of miRNA in cell growth and apoptosis" *Nucleic Acids Research* 33:1290-1297 (2005).

miRNA genes and/or gene products have been used to identify specific mutations associated with genomic regions that harbor miRNA genes in chronic lymphocytic leukemia patients, thereby providing a diagnostic screen. Croce et al., "Diagnosis And Treatment Of Cancers With MicroRNA Located In Or Near Cancer Associated Chromosomal Features" United States Patent Application Publ. No. 2006/0105360.

None of these published studies, however, suggest that any miRNA may regulate P2X$_7$ expression in either normal or cancer cells. To better understand the potential role of miRNA involvement in regulation of P2X$_7$ mRNA, the sequence of the 3'UTR of the P2X$_7$ gene (presented below) was studied:

```
                  (SEQ ID NO: 19; Accession No. BC011913)
        agccaggcaccgtggctcacgtctgtaatcccagcgctttggga ggccgaggcaggcagatcacctgaggtcgggagttggagacccgcctggc taacaaggcgaaatcctgtctgtactaaaaatacaaaaatcagccagaca tggtggcatgcacctgcaatcccagctactcgggaggctgaggcacaaga atcacttgaacccgggaggcagaggttgtagtgagcccagattgtgccac tgctctccagcctgggaggcacagcaaactgtccccaaaaaaaaaaaa | gagtccttaccaatagcaggggctgcagtagccatgttaacatgacattt accagcaacttgaacttcacctgcaaagctctgtggccacattttcagcc aaagggaaatatgctttcatcttctgttgctctctgtgtctgagagcaaa gtgacctggttaaacaaaccagaatccctctacatggactcagagaaaag agattgagatgtaagtctcaactctgtccccaggaagttgtgtgaccccta ggcctctcacctctgtgcctctgtctccttgttgcccaactactatctca
```

-continued

```
gagatattgtgaggacaaattgagacagtgcacatgaactgtcttttaat gtgtaaagatctacatgaatgcaaaacatttcattatgaggtcagactag gataatgtccaactaaaaacaaacccttttcatcctggctggagaatgtg GAGAACTAAAGGTGGCCACAAATTCTTTGa | cactcaagtcccccaagac ctaagggttttatctcctcccttgaatatgggtggctctgattgcttta tccaaaagtggaagtgacattgtgtcagtttcagatcctgatcttaagag gctgacagcttctacttgctgtcccttggaactcttgctatcggggaagc cagacgccatttaaaagtctgcctatcctggccaggtgtggtggctcaCA CCTGTAATCCCAGCACTTTGGGAGAccaaggcgggcggatcacttaaagt caggagtccaagaccagactcgccaacatggtgaaaccgtatctctaata aaaatacaaaaattagctgggcatggtgcgggcacctgtagtcctagcta tcaagaggctgagacaggagaaacacttgaacctgggaggtggaggttgc attgagctgagatcgtgccactgcactccaggctgggtgacagagcgaga ctccatctcaaaaaaaaaaaaaagaaaaa.
```

Using two websites (microma.sanger.ac.uk/sequences/search.shtml and cbio.mskcc.org/cgi-bin/mirnaviewer/mirnaviewer.pl) sequences were found within SEQ ID NO: 19 that matched with at least two miRNAs (i.e., for example, miR-186 and miR-150). The nucleic acid sequences of these miRNAs are, respectively: miR-186: CAAAGAATTCTCC-TTTTGGGCTT (SEQ ID NO; 20) and miR-150 TCTCCCAACCCTTGTACCAGTG (SEQ ID NO: 21). The sequence portions underlined in each miRNA comprise a cis seed element sequence that is exactly complementary to one of the two underlined sequences in SEQ ID NO: 19. Based on a perfect match of these seed cis element sequences, and extended complementarity of additional sequences indicated by the non-underlined nucleic acids, these data suggest that regions in the 3'UTR human P2X$_7$ mRNA contain miRNA-dependent instability sites.

The potential role of miRNA involvement in regulation of P2X$_7$ mRNA, was studied by determining the stability of shorter segments of the P2X$_7$-3'UTR. Cells were transfected with luciferase vectors containing either the middle (second) segment of the 3'UTR-P2x7, delineated by the first and second vertical lines in SEQ ID NO:19 (i.e., for example, miR-186), or the distal (third) segment of the 3'UTR-P2X$_7$, delineated from the second vertical line onwards in SEQ ID NO: 19 (i.e., for example, miR-150). See, Example 5 & FIG. 8. Although it is not necessary to understand the mechanism of an invention, it is believed that the obtained data showing steady state luciferase mRNA levels (expressed from a P2X$_7$ vector) support the hypothesis that miR-186 and miR-150 alone, or in combination could function as a cis-acting site involved in degradation of the P2X$_7$ transcript.

Although it is not necessary to understand the mechanism of an invention, it is believed that the results in FIG. 8 can be interpreted in at least two possible ways. One such possibility, not ruling out other possible scenarios, is that miR-186 stabilizes P2X$_7$ mRNA in normal cells and destabilizes P2X$_7$ mRNA in cancer cells. Accordingly, a stabilizing effect in normal cells is dependent on a precise alignment of miR-186 with a homologous segment of a 3'UTR-P2X$_7$ (i.e., for example, a seed cis-element). This observation is supported by data showing that a mutation in a 3'UTR-P2X$_7$ miR-186 seed cis-element abolishes stabilization in normal cells. In contrast, in cancer cells the effect is less dependent on a precise alignment of a miR-186 with a 3'UTR-P2X$_7$ seed cis-element because a mutation in the region of a miR-186 seed cis-element has a lesser effect in cancer cells than in normal cells.

Another possible explanation (again, not ruling out other possible scenarios) is that miR-150 destabilizes P2X$_7$ mRNA. In this hypothesis, normal cells would not produce and/or produce limited amounts of miR-150, and therefore overexpression of a 3'-UTR comprising a complementary sequence to miR-150 would not be expected to decrease mRNA levels. The present data supports this concept because a luciferase reporter linked to either a 3'UTR-P2X$_7$ miR-150-WT complementary segment or a 3'UTR-P2X$_7$ miR-150-M complementary segment produced no effect on luciferase mRNA-P2X$_7$ levels in normal cells. In contrast, cancer cells would be expected to produce miR-150 thereby reducing mRNA levels (i.e., for example, by reduced expression and/or increased degradation). The present data supports this concept because overexpression of a luciferase reporter linked to a 3'UTR-P2X$_7$ miR-150-WT complementary segment is associated with decreased production of luciferase mRNA. Although it is not necessary to understand the mechanism of an invention, it is believed that miR-150 produced by cancer cells binds to a miR-150-WT complementary segment residing in front of the luciferase promoter thereby inhibiting transcription and/or increasing degradation of luciferase mRNA. Accordingly, overexpression of a 3'UTR-P2X$_7$ miR-150-M complementary segment is associated with a lesser inhibition of luciferase mRNA production (i.e., for example, slightly higher steady state levels). Although it is not necessary to understand the mechanism of an invention, it is believed that the miR-150 does not bind as effectively to the 3'UTR-P2X$_7$ miR-150-M complementary segment as compared to the 3'UTR-P2X$_7$ miR-150-WT complementary segment.

In one embodiment, the present invention contemplates a method comprising cancer epithelial cells degrading P2X$_7$ mRNA by activating instability domains located at a 3'UTR-P2X$_7$, wherein the activation is performed by miR-186 and/or miR-150. In one embodiment, the present invention contemplates a composition comprising a 3'UTR-P2X$_7$ gene having at least one hybridization site for miR-150 and/or miR-186. Although it is not necessary to understand the mechanism of an invention, it is believed that degradation of P2X$_7$ mRNA in cancer cells involves binding of either a miR-150 and/or miR-186 to a 3'UTR-P2X$_7$ hybridization site.

D. Screening for Pathophysiological Conditions with miRNAs

In one embodiment, the present invention contemplates a method for screening samples from a subject at risk for, or having a predisposition to develop, a cancer (i.e., for example, uterine cancer). In one embodiment, the method comprises detecting at least one miRNA (i.e., for example, miR-186 and/or miR-150) capable of binding to a P2X$_7$ mRNA. In one embodiment, the miRNA from the sample is measured by quantitatively reverse transcribing the miRNA to form a complementary target oligodeoxynucleotide, and hybridizing the target oligodeoxynucleotide to a microarray comprising a probe oligonucleotide specific for the miRNA. In another embodiment, the levels of multiple miRNA in a sample are measured in this fashion, by quantitatively reverse transcribing the miRNA to form complementary target oligodeoxynucleotides, and hybridizing the target oligodeoxynucleotides to a microarray comprising probe oligonucleotides specific for the miRNAs. In another embodiment, the multiple miRNAs are simultaneously reverse transcribed, and the resulting set of target oligodeoxynucleotides are simultaneously exposed to the microarray.

E. Diagnosing Pathophysiological Conditions with miRNAs

In one embodiment, the present invention contemplates a method of diagnosing cancer (i.e., for example, uterine cancer) in a subject. In one embodiment, the method comprises reverse transcribing total RNA from a sample from the subject to provide a set of labeled target oligodeoxynucleotides; hybridizing the target oligodeoxynucleotides to a microarray comprising miRNA-specific probe oligonucleotides (i.e., for example, miR-150 and/or miR-186) to provide a hybridization profile for the sample; and comparing the sample hybridization profile to the hybridization profile generated from a control sample. In one embodiment, an alteration in the subject's profile, as compared to the control profile, being indicative of the subject either having, or being at risk for developing, a cancer. The microarray of miRNA-specific probe oligonucleotides preferably comprises miRNA-specific probe oligonucleotides for a substantial portion of the human miRNA's (i.e., for example, the full complement of microRNA genes in a cell). In one embodiment, the microarray comprises at least about 60%, 70%, 80%, 90%, or 95% of the human miRNA's. In one embodiment, the cancer is associated with reduced P2X$_7$ mRNA. In one embodiment, the cancer comprises uterine cancer. In another embodiment, the cancer is associated with one or more adverse cancer biomarkers. In one embodiment, the uterine cancer is endometrial adenocarcinoma. In a particular embodiment, the uterine cancer is endocervical adenocarcinoma. In one embodiment, the uterine cancer is ectocervical squamous cell carcinoma. In one embodiment, the uterine cancer is ectocervical dysplasia.

F. Treating Pathophysiological Conditions with miRNAs

In one embodiment, the present invention contemplates a method of treating a cancer comprising elevated miRNA levels within a cancer cell, as compared to non-cancerous cells. In one embodiment, the treating comprises reducing the elevated miRNA levels. In one embodiment, the cancer cell further comprises reduced intracellular P2X$_7$ mRNA levels as compared to non-cancerous cells. In one embodiment, the elevated miRNA levels are reduced by administering to the cancer cell an effective amount of at least one compound capable of inhibiting expression of the miRNA, such that the intracellular P2X$_7$ mRNA levels are increased. In one embodiment, the administration of an miRNA expression inhibitor inhibits proliferation of cancer cells in the subject.

In one embodiment, the invention contemplates a method of treating cancer comprising the following steps: i) determining the amount of miRNA (i.e., for example, miR-150 and/or miR-186) expressed in a plurality of cancer cells relative to non-cancerous cells of the same type; ii) administering to the subject an effective amount of at least one compound for inhibiting expression of the miRNA, such that proliferation of cancer cells in the subject is inhibited. In one embodiment, the cancer is associated with reduced P2X$_7$ mRNA. In one embodiment, the cancer comprises uterine cancer. In another embodiment, the cancer is associated with one or more adverse cancer biomarkers. In one embodiment, the uterine cancer is endometrial adenocarcinoma. In a particular embodiment, the uterine cancer is endocervical adenocarcinoma. In one embodiment, the uterine cancer is ectocervical squamous cell carcinoma. In one embodiment, the uterine cancer is ectocervical dysplasia.

Thus, in the practice of the present treatment methods, an effective amount of at least one inhibitor of an miRNA can be administered to a subject. As used herein, an "effective amount" of an miRNA inhibitor is an amount sufficient to inhibit specific symptoms of a pathophysiological condition (i.e., for example, proliferation of a cancer cell in a subject suffering from a cancer). An effective amount of an miRNA inhibitor to be administered to a given subject can readily be determined by medical personnel by taking into account factors such as the size and weight of the subject; the extent of disease penetration; the age, health and sex of the subject; the route of administration; and whether the administration is regional or systemic.

For example, an effective amount of an miRNA inhibitor can be based on the approximate weight of a tumor mass to be treated. The approximate weight of a tumor mass can be determined by calculating the approximate volume of the mass, wherein one cubic centimeter of volume is roughly equivalent to one gram. An effective amount of an miRNA inhibitor based on the weight of a tumor mass can be at least about 10 micrograms/gram of tumor mass, and is preferably between about 10-500 micrograms/gram of tumor mass. More preferably, the effective amount is at least about 60 micrograms/gram of tumor mass. Particularly preferably, the effective amount is at least about 100 micrograms/gram of tumor mass. In one embodiment, an effective amount based on the weight of the tumor mass is injected directly into the tumor.

An effective amount of an miRNA inhibitor can also be based on the approximate or estimated body weight of a subject to be treated. For example, an effective amount of an miRNA inhibitor is administered to a subject can range from about 5-3000 micrograms/kg of body weight, and is preferably between about 700-1000 micrograms/kg of body weight, and is more preferably greater than about 1000 Micrograms/kg of body weight.

An appropriate dosage regimen for the administration of an miRNA inhibitor to a given subject can also be determined. For example, an miRNA inhibitor can be administered to the subject once (i.e., for example., as a single injection or a deposition for sustained controlled release). Alternatively, an miRNA inhibitor can be administered once or twice daily to a subject for a period of from about three to about twenty-eight days, more preferably from about seven to about ten days. In a preferred dosage regimen, an miRNA inhibitor is administered once a day for seven days. Where a dosage regimen comprises multiple administrations, it is understood that the effective amount of an miRNA inhibitor administered to the subject can comprise the total amount of inhibitor administered over the entire dosage regimen.

G. Providing Pathophysiological Condition Prognoses with miRNAs

In one embodiment, the present invention contemplates a method of providing a prognosis in a cancer subject, wherein the cancer is associated with reduced $P2X_7$ mRNA. In one embodiment, the cancer comprises elevated miRNA levels within a cancer cell, as compared to non-cancerous cells. In one embodiment, the prognoses comprises; i) determining an miRNA/mRNA ratio from a cancer cell; and ii) assigning a survivability score to the subject based upon the miRNA/mRNA ratio. In one embodiment, the mRNA comprises $P2X_7$ mRNA. In one embodiment, a high ratio, as compared to a non-cancerous cell, indicates a poor prognosis. In one embodiment, an equivalent and/or low ratio, as compared to a non-cancerous cell, indicates a good prognoses.

H. miRNA Inhibitors

Suitable compounds for miRNA inhibitors include, but are not limited to, double-stranded RNA (such as short- or small-interfering RNA or "siRNA"), antisense nucleic acids, and enzymatic RNA molecules such as ribozymes. Each of these compounds can be targeted to a given miRNA and destroy and/or induce the destruction of an miRNA. In one embodiment, an miRNA inhibitor is directed towards inhibiting the expression of miRNA including, but not limited to, miR-150 and/or miR-186.

For example, expression of any given miRNA gene can be inhibited by inducing RNA interference of the miRNA gene with an isolated double-stranded RNA ("dsRNA") molecule which has at least 90%, for example 95%, 98%, 99% or 100%, sequence homology with at least a portion of the miRNA gene product. In one embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length, but more preferable about 21 nucleotides. The siRNA comprise a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within a target miRNA gene product.

As used herein, a nucleic acid sequence in an siRNA which is "substantially identical" to a target sequence contained within a target mRNA is a nucleic acid sequence that is identical to the target sequence, or that differs from the target sequence by one or two nucleotides. The sense and antisense strands of an siRNA can comprise two complementary, single-stranded RNA molecules, or can comprise a single molecule in which two complementary portions are base-paired and are covalently linked by a single-stranded "hairpin" area.

An siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in one embodiment, an siRNA comprises at least one 3' overhang of from 1 to about 6 nucleotides (which includes ribonucleotides or deoxyribonucleotides) in length, preferably from 1 to about 5 nucleotides in length, more preferably from 1 to about 4 nucleotides in length, and particularly preferably from about 2 to about 4 nucleotides in length. In one embodiment, the 3' overhang is present on both strands of the siRNA, and is 2 nucleotides in length. For example, each strand of the siRNA can comprise 3' overhangs of dithymidylic acid ("TT") or diuridylic acid ("uu").

An siRNA can be produced chemically or biologically, or can be expressed from a recombinant plasmid or viral vector. Several methods for producing and testing dsRNA or siRNA molecules are described. U.S. Patent Application Publ. No., 2002/0173478 to Gewirtz; and U.S. Patent Application Publ. No. 2004/0018176 to Reich et al., the entire disclosures of which are herein incorporated by reference.

Expression of any given miRNA gene can also be inhibited by an antisense nucleic acid. Antisense nucleic acid usually comprise a nucleic acid sequence that is approximately between 50-100% complementary, more preferably 75-100% complementary, and most preferably 95-100% complementary to a contiguous nucleic acid sequence in an miRNA gene product. In one embodiment, nucleic acid sequences for a miRNA gene product to which antisense nucleic acid may be produced include, but are not limited to, SEQ ID NO: 1, SEQ ID NO: 2, SEQ ID NO: 3, SEQ ID NO: 20 and/or SEQ ID NO:21. Although it is not necessary to understand the mechanism of an invention, it is believed that antisense nucleic acids: i) sterically inhibit DNA transcription; ii) sterically inhibit ribozyme-associated RNA translation; and iii) activate RNase H and/or some other cellular nuclease that digests a miRNA gene product/antisense nucleic acid duplex.

Antisense nucleic acids can also contain modifications to their nucleic acid backbone or to their sugar and/or base moieties (or their equivalent) to enhance target specificity, nuclease resistance, delivery or other properties related to efficacy of the molecule. Such modifications include cholesterol moieties, duplex intercalators such as acridine or the inclusion of one or more nuclease-resistant groups.

Antisense nucleic acids can be produced chemically or biologically, or can be expressed from a recombinant plasmid or viral vector. Stein et al., *Science* 261:1004 (1993); and U.S. Pat. No. 5,849,902 to Woolf et al., the entire disclosures of which are herein incorporated by reference.

miRNA gene expression can also be inhibited by an enzymatic nucleic acid. Preferably, the enzymatic nucleic acid substrate binding region is 50-100% complementary, more preferably 75-100% complementary, and most preferably 95-100% complementary to a contiguous nucleic acid sequence in an miRNA gene product. The enzymatic nucleic acids can also comprise modifications at the base, sugar, and/or phosphate groups. An exemplary enzymatic nucleic acid for use in the present methods is a ribozyme. Enzymatic nucleic acids can be produced chemically or biologically, or can be expressed from a recombinant plasmid or viral vector. Exemplary methods for producing and testing dsRNA or siRNA molecules are described. Werner et al., *Nucl. Acids Res.* 23:2092-96 (1995); Hammann et al., *Antisense and Nucleic Acid Drug Dev.* 9:25-31 (1999); and U.S. Pat. No. 4,987,071 to Cech et al; the entire disclosures of which are herein incorporated by reference.

I. Administration of miRNA and/or miRNA Inhibitors miRNA gene products and/or miRNA gene expression-inhibiting compounds can be administered to a subject by any means suitable for delivering these compounds to a subject. For example, miRNA gene products and/or miRNA expression inhibiting compounds can be administered by methods suitable to transfect cells of a subject with these compounds, or with nucleic acids comprising sequences encoding these compounds. Preferably, cells are transfected with a plasmid or viral vector comprising sequences encoding at least one miRNA gene product or miRNA gene expression inhibiting compound.

An miRNA gene product and/or miRNA gene expression inhibiting compound can also be administered to a subject by any suitable enteral or parenteral administration route. Suitable enteral administration routes for the present methods include, but are not limited to, oral, rectal, or intranasal delivery. Suitable parenteral administration routes include, but are not limited to, intravascular administration (i.e., for example, intravenous bolus injection, intravenous infusion, intra-arterial bolus injection, intra-arterial infusion and catheter installation into the vasculature); peri- and intra-tissue injection (i.e., for example, peri-tumoral and intra-tumoral injection, intra-retinal injection, or subretinal injection); subcutaneous injection or deposition, including, but not limited to, subcutaneous infusion (i.e., for example, by osmotic pumps); direct application to the tissue of interest, for example by a catheter or other placement device (i.e., for example, a retinal pellet or a suppository or an implant comprising a porous, non-porous, or gelatinous material); and inhalation. Another administration route includes, but is not limited to, injection and/or infusion directly into a tumor.

In the present methods, an miRNA gene product or miRNA gene expression inhibiting compound can be administered to a subject either as naked RNA, in combination with a delivery reagent, or as a nucleic acid (i.e., for example, a recombinant plasmid or viral vector) comprising sequences that express an miRNA gene product or miRNA expression-inhibiting compound. Suitable delivery reagents include, but are not limited to, the Mirus Transit TKO® lipophilic reagent; lipofectin; lipofectamine; cellfectin; polycations (e.g., polylysine), or liposomes.

Liposomes are used to deliver an miRNA gene product or a miRNA gene expression-inhibiting compound (or nucleic acids comprising sequences encoding them) to a subject. Liposomes can also increase the blood half-life of the gene products or nucleic acids.

Liposomes suitable for use in the invention can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods can be used for preparing liposomes. Szoka et al., *Ann. Rev. Biophys. Bioeng.* 9:467 (1980); and U.S. Pat. Nos. 4,235,871, 4,501,728, 4,837,028, and 5,019,369, the entire disclosures of which are herein incorporated by reference.

The liposomes for use in the present methods can comprise a ligand molecule that targets the liposome to cancer cells. Ligands which bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES. U.S. Pat. No. 4,920,016, the entire disclosure of which is herein incorporated by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include, but are not limited to, polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to a liposome membrane. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example solid tumors, will efficiently accumulate these liposomes. Gabizon, et al., *Proc. Nail. Acad. Sci.*, USA, 18:6949-6953 (1988). In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miRNA gene products or miRNA gene expression inhibition compounds (or nucleic acids comprising sequences encoding them) to tumor cells.

J. miRNA and/or miRNA Inhibitors Pharmaceutical Formulations miRNA gene products and/or miRNA gene expression-inhibitor compounds are preferably formulated as pharmaceutical compositions, sometimes called "medicaments," prior to administering to a subject. Pharmaceutical compositions of the present invention are characterized as being at least sterile and pyrogen-free. As used herein, "pharmaceutical formulations" include, but are not limited to, formulations for human and veterinary use. Methods for preparing pharmaceutical compositions of the invention are described. In: *Remington's Pharmaceutical Science,* 17th ed., Mack Publishing Company, Easton, Pa. (1985), the entire disclosure of which is herein incorporated by reference.

Pharmaceutical formulations contemplated by the present invention comprise at least one miRNA gene product and/or miRNA gene expression inhibition compound (or at least one nucleic acid comprising sequences encoding them) (e.g., 0.1 to 90% by weight), or a physiologically acceptable salt thereof, mixed with a pharmaceutically-acceptable carrier. Pharmaceutical formulations of the invention may also comprise at least one miRNA gene product and/or miRNA gene expression inhibition compound (or at least one nucleic acid comprising sequences encoding them) which may be encapsulated by liposomes and/or a pharmaceutically-acceptable carrier. In one embodiment, a pharmaceutical composition comprises an miRNA gene expression inhibitor directed to an miRNA including, but not limited to, miR-150 and/or miR-186.

Preferred pharmaceutically-acceptable carriers are water, buffered water, normal saline, 0.4% saline, 0.3% glycine, hyaluronic acid and the like.

In one embodiment, a pharmaceutical composition of the present invention comprises at least one miRNA gene product or miRNA gene expression inhibitor compound (or at least one nucleic acid comprising sequences encoding them) which is resistant to degradation by nucleases. Nucleic acids may be synthesized that are nuclease resistant, for example by incorporating one or more ribonucleotides that are modified at the 2'-position. Suitable 2'-modified ribonucleotides include those modified at the 2'-position with fluoro, amino, alkyl, alkoxy, and O-allyl.

Pharmaceutical compositions of the invention can also comprise conventional pharmaceutical excipients and/or additives. Suitable pharmaceutical excipients include, but are not limited to, stabilizers, antioxidants, osmolality adjusting agents, buffers, and pH adjusting agents. Suitable additives include, but are not limited to, physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used including, but not limited to, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miRNA gene product and/or miRNA gene expression inhibition compound (or at least one nucleic acid comprising sequences encoding them). A pharmaceutical composition for aerosol (inhalational) administration can comprise 0.01-20% by weight, preferably 1%-10% by weight, of the at least one miRNA gene product and/or miRNA gene expression inhibition compound (or at least one nucleic acid comprising sequences encoding them) encapsulated in a liposome as described above, and a propellant. A carrier can also be included as desired; e.g., lecithin for intranasal delivery.

III. RNA Binding Proteins

The present invention contemplates that RNA binding proteins (RBPs) comprise potential targets for the screening, detecting, diagnosing, and prognosis of pathophysiologic condition. For example, it has been reported that RBPs may be involved in human autoimmune or genetic neurologic diseases. Notable examples among autoimmune disease include, but are not limited to, systemic lupus erythematosis, primary biliary cirrhosis (PBC) and Sjogren's syndrome, and among neurologic disease include the paraneoplastic neurologic antigens Nova and Hu, and the Fragile X mental retardation FMR1 protein, the spinal muscular atrophy SMN protein, the myotonic dystrophy CELF proteins, and the spinocerebellar ataxia SCA1 protein.

Understanding the role RPBs play in disease and normal biology requires methods to identify the set of RNAs they bind to in vivo, and the use of mouse models of these disorders for RNA target validation. Accordingly, the present invention utilizes methods for purifying RNA molecules interacting with an RNA. Darnell et al., "Method of purifying RNA binding protein-RNA complexes" United States Patent Application 2005/0227251 (herein incorporated by reference).

The regulation of gene expression and cellular function may be controlled at many different levels in eukaryotic cells. Evidence has been accumulated over the past few years pointing to the importance of mRNA stability, localization, and translation in these processes during development and maintenance of the differentiated phenotype. Ferrandon et al., *Cell* 79:1221-1232 (1994); and Hentze, M. W. *Curr. Op. Biol.* 7:393-398 ((1995), respectively. Central to the regulation of these processes are proteins which recognize and bind to specific primary sequences or secondary structures in nucleic acids. Increasing numbers of these proteins are being identified, and a variety of nucleic acid-binding motifs have been recognized. Burd et al., *Science* 265:615-621 (1994).

The present invention provides, in one embodiment, methods of purifying an RNA molecule interacting with an RBP of interest; comprising covalent cross-linking and immunoprecipitation, and the use of such methods to analyze association of an RNA transcript with an RBP. The invention also provides sequences of RNA molecules that mediate binding to an RBP, proteins encoded by the sequences, methods of identifying the sequences, and the use of the sequences in a screening assay to identify bioactive molecules. The invention also provides RNA motifs found among the sequences and compounds that bind to the RNA motifs. In addition, the invention provides methods of treating diseases associated with a function of an RNA binding protein In one embodiment, the present invention contemplates a method for purifying an RNA molecule interacting with an RBP of interest in a biological sample, comprising the steps of: (a) contacting the biological sample with an agent that creates a covalent bond between the RNA molecule and the RBP of interest, thereby generating a covalently bound RBP-RNA complex containing the RNA molecule; (b) cleaving the RNA molecule by contacting the RBP-RNA complex with an agent capable of cleaving a bond thereof, thereby generating a fragment of the RNA molecule; (c) selecting the RBP-RNA complex with a molecule that specifically interacts with a component of the RBP-RNA complex; and (d) purifying the RBP-RNA complex under stringent conditions, thereby purifying an RNA molecule interacting with an RBP of interest. The general term for methods of the present invention for purifying an RNA molecule interacting with an RBP of interest, comprising covalent cross-linking and immunoprecipitation, is "the CLIP method" (i.e., for example, cross-linking and immunoprecipitation method).

In one embodiment, the present invention contemplates that post-transcriptional regulation of gene expression may also be mediated by RNA binding proteins (RBPs). There are >750 unique human RBPs. Using Real-Time RT-PCR, a profile comprising expression of 75 RBPs, are contemplated by the present invention to detect changes in the mRNA levels of numerous RBPs in Hela cervical cancer cells compared to normal human cervical cells. For example, three RBPs have been identified showing altered expression in cancer cells. See, FIG. 10. Compared to normal cervical tissue, CUGBP2 and of ANXA2 have significantly decreased expression in the cervical cancer cell line, HeLa. In contrast, levels of IGF2BP3 were higher in HeLa cells than in normal cervical tissues. Although it is not necessary to understand the mechanism of an invention, it is believed that changes in concentration, distribution and/or modification of RBPs that bind the 3' UTR-$P_2X7$ regulatory regions could differentially affect $P2X_7$ mRNA degradation and expression in normal and cancer epithelial cells. Other RBPs may also be involved in the posttranscriptional regulation of $P2X_7$ mRNA.

The present invention contemplates RBP regulation of pathophysiological conditions by such RBPs including, but not limited to, those identified in Table 2.

TABLE 2

Representative RNA Binding Protiens Regulating Pathophysiological Conditions

| | | | |
|---|---|---|---|
| 1: TARBP2 Tar (HIV-1) RNA b . . . [GeneID: 6895] | 2: CUGBP2 CUG triplet repea . . . [GeneID: 10659] | 3: CUGBP1 CUG triplet repea . . . [GeneID: 10658] | 4: CIRBP cold inducible RN . . . [GeneID: 1153] |
| 5: RALY RNA binding prote . . . [GeneID: 22913] | 6: TAF15 TAF15 RNA polymer . . . [GeneID: 8148] | 7: HNRPD heterogeneous nuc . . . [GeneID: 3184] | 8: TARBP1 Tar (HIV-1) RNA b . . . [GeneID: 6894] |
| 9: RBM38 RNA binding motif . . . [GeneID: 55544] | 10: BRUNOL5 bruno-like 5, RNA . . . [GeneID: 60680] | 11: TIA1 TIA1 cytotoxic gr . . . [GeneID: 7072] | 12: BRUNOL6 bruno-like 6, RNA . . . [GeneID: 60677] |
| 13: QKI quaking homolog, . . . [GeneID: 9444] | 14: RBMS3 RNA binding motif . . . [GeneID: 27303] | 15: RBMY1A1 RNA binding motif . . . [GeneID: 5940] | 16: SRP14 signal recognitio . . . [GeneID: 6727] |
| 17: LOC652515 similar to Probab . . . [GeneID: 652515] | 18: RBPMS RNA binding prote . . . [GeneID: 11030] | 19: RBM23 RNA binding motif . . . [GeneID: 55147] | 20: AUH AU RNA binding pr . . . [GeneID: 549] |
| 21: RBM39 RNA binding motif . . . [GeneID: 9584] | 22: RBM10 RNA binding motif . . . [GeneID: 8241] | 23: RBM4B RNA binding motif . . . [GeneID: 83759] | 24: RDBP RD RNA binding pr . . . [GeneID: 7936] |
| 25: CSDC2 cold shock domain . . . [GeneID: 27254] | 26: DRB1 developmentally r . . . [GeneID: 129831] | 27: KHDRBS2 KH domain contain . . . [GeneID: 202559] | 28: RNPS1 RNA binding prote . . . [GeneID: 10921] |
| 29: TIAL1 TIA1 cytotoxic gr . . . [GeneID: 7073] | 30: RBM16 RNA binding motif . . . [GeneID: 22828] | 31: RBM25 RNA binding motif . . . [GeneID: 58517] | 32: RBPMS2 RNA binding prote . . . [GeneID: 348093] |
| 33: RBED1 RNA binding motif . . . [GeneID: 84173] | 34: BRUNOL4 bruno-like 4, RNA . . . [GeneID: 56853] | 35: STRBP spermatid perinuc . . . [GeneID: 55342] | 36: RBM24 RNA binding motif . . . [GeneID: 221662] |
| 37: LOC652783 similar to RNA bi . . . [GeneID: 652783] | 38: KHRBP1 KH-type RNA bindi . . . [GeneID: 80711] | 39: RBMS1 RNA binding motif . . . [GeneID: 5937] | 40: STAU1 staufen, RNA bind . . . [GeneID: 6780] |
| 41: RBM3 RNA binding motif . . . [GeneID: 5935] | 42: RBM4 RNA binding motif . . . [GeneID: 5936] | 43: RBM9 RNA binding motif . . . [GeneID: 23543] | 44: RBM35B RNA binding motif . . . [GeneID: 80004] |

TABLE 2-continued

Representative RNA Binding Proteins Regulating Pathophysiological Conditions

| | | | |
|---|---|---|---|
| 45: PTBP1 polypyrimidine tr . . . [GeneID: 5725] | 46: RBMX RNA binding motif . . . [GeneID: 27316] | 47: CSDE1 cold shock domain . . . [GeneID: 7812] | 48: POLDIP3 polymerase (DNA-d . . . [GeneID: 84271] |
| 49: C14orf156 chromosome 14 ope . . . [GeneID: 81892] | 50: ZRSR1 zinc finger (CCCH . . . [GeneID: 7310] | 51: ZRSR2 zinc finger (CCCH . . . [GeneID: 8233] | 52: RPL3 ribosomal protein L3 [GeneID: 6122] |
| 53: NONO non-POU domain co . . . [GeneID: 4841] | 54: EIF3S4 eukaryotic transi . . . [GeneID: 8666] | 55: SF4 splicing factor 4 [GeneID: 57794] | 56: ILF3 interleukin enhan . . . [GeneID: 3609] |
| 57: Tenr testis nuclear RN . . . [GeneID: 132612] | 58: LOC161931 testis nuclear RN . . . [GeneID: 161931] | 59: ZNF346 zinc finger prote . . . [GeneID: 23567] | 60: RBM8A RNA binding motif . . . [GeneID: 9939] |
| 61: RNPC3 RNA-binding regio . . . [GeneID: 55599] | 62: RBM13 RNA binding motif . . . [GeneID: 84549] | 63: RBMY1G RNA binding motif . . . [GeneID: 5943] | 64: RBMY1C RNA binding motif . . . [GeneID: 5942] |
| 65: RBMY1A2 RNA binding motif . . . [GeneID: 5941] | 66: LOC647082 similar to Hetero . . . [GeneID: 647082] | 67: LOC641705 similar to RNA-bi . . . [GeneID: 641705] | 68: LOC654340 RNA-binding regio . . . [GeneID: 654340] |
| 69: MKL1 megakaryoblastic . . . [GeneID: 57591] | 70: FLJ20273 RNA-binding protein [GeneID: 54502] | 71: LOC729102 similar to Hetero . . . [GeneID: 729102] | 72: LOC731623 similar to Hetero . . . [GeneID: 731623] |
| 73: LOC652309 similar to RNA-bi . . . [GeneID: 652309] | 74: LOC644584 similar to RNA-bi . . . [GeneID: 644584] | 75: LOC730246 similar to Hetero . . . [GeneID: 730246] | 76: LOC643167 similar to RNA-bi . . . [GeneID: 643167] |
| 77: LOC731363 similar to Hetero . . . [GeneID: 731363] | 78: LOC731307 similar to Hetero . . . [GeneID: 731307] | 79: LOC728732 similar to Hetero . . . [GeneID: 728732] | 80: LOC642958 similar to Hetero . . . [GeneID: 642958] |
| 81: LOC440125 similar to Hetero . . . [GeneID: 440125] | 82: LOC341333 similar to Hetero . . . [GeneID: 341333] | 83: LOC129402 similar to RNA-bi . . . [GeneID: 129402] | 84: LOC729984 similar to Hetero . . . [GeneID: 729984] |
| 85: LOC645347 similar to Hetero . . . [GeneID: 645347] | 86: LOC644037 similar to Hetero . . . [GeneID: 644037] | 87: LOC391804 similar to RNA-bi . . . [GeneID: 391804] | 88: EIF2C1 eukaryotic transl . . . [GeneID: 26523] |
| 89: LOC732365 similar to Hetero . . . [GeneID: 732365] | 90: LOC643989 similar to Hetero . . . [GeneID: 643989] | 91: LIN28 lin-28 homolog (C . . . [GeneID: 79727] | 92: LOC732259 similar to Hetero . . . [GeneID: 732259] |
| 93: LOC400769 similar to Hetero . . . [GeneID: 400769] | 94: LOC391689 similar to Hetero . . . [GeneID: 391689] | 95: LOC391670 similar to Hetero . . . [GeneID: 391670] | 96: LOC391640 similar to Hetero . . . [GeneID: 391640] |
| 97: LOC732182 similar to Hetero . . . [GeneID: 732182] | 98: LOC645001 similar to Hetero . . . [GeneID: 645001] | 99: LOC732014 similar to Hetero . . . [GeneID: 732014] | 100: LOC730746 similar to Hetero . . . [GeneID: 730746] |
| 101: LOC729423 similar to Hetero . . . [GeneID: 729423] | 102: LOC728170 similar to Hetero . . . [GeneID: 728170] | 103: LOC729366 similar to Hetero . . . [GeneID: 729366] | 104: LOC391378 similar to Hetero . . . [GeneID: 391378] |
| 105: PCBP4 poly(rC) binding . . . [GeneID: 57060] | 106: KHDRBS1 KH domain contain . . . [GeneID: 10657] | 107: RBM12 RNA binding motif . . . [GeneID: 10137] | 108: RBM15B RNA binding motif . . . [GeneID: 29890] |
| 109: RBMS2 RNA binding motif . . . [GeneID: 5939] | 110: RBMY1F RNA binding motif . . . [GeneID: 159163] | 111: SRBD1 S1 RNA binding do . . . [GeneID: 55133] | 112: RBM35A RNA binding motif . . . [GeneID: 54845] |
| 113: KHDRBS3 KH domain contain . . . [GeneID: 10656] | 114: RBM15 RNA binding motif . . . [GeneID: 64783] | 115: RBM22 RNA binding motif . . . [GeneID: 55696] | 116: RBM5 RNA binding motif . . . [GeneID: 10181] |
| 117: RBM6 RNA binding motif . . . [GeneID: 10180] | 118: RBM7 RNA binding motif . . . [GeneID: 10179] | 119: RBM12B RNA binding motif . . . [GeneID: 389677] | 120: ZCRB1 zinc finger CCHC- . . . [GeneID: 85437] |
| 121: RBMX2 RNA binding motif . . . [GeneID: 51634] | 122: RBM34 RNA binding motif . . . [GeneID: 23029] | 123: RBM43 RNA binding motif . . . [GeneID: 375287] | 124: RBM19 RNA binding motif . . . [GeneID: 9904] |
| 125: RBM33 RNA binding motif . . . [GeneID: 155435] | 126: RBM11 RNA binding motif . . . [GeneID: 54033] | 127: RBM41 RNA binding motif . . . [GeneID: 55285] | 128: RBM28 RNA binding motif . . . [GeneID: 55131] |
| 129: RBM17 RNA binding motif . . . [GeneID: 84991] | 130: RBM26 RNA binding motif . . . [GeneID: 64062] | 131: RBM18 RNA binding motif . . . [GeneID: 92400] | 132: RBM14 RNA binding motif . . . [GeneID: 10432] |
| 133: TUT1 terminal uridylyl . . . [GeneID: 64852] | 134: RBM27 RNA binding motif . . . [GeneID: 54439] | 135: PNO1 partner of NOB1 h . . . [GeneID: 56902] | 136: ZCCHC17 zinc finger, CCHC . . . [GeneID: 51538] |
| 137: NHP2L1 NHP2 non-histone . . . [GeneID: 4809] | 138: RBMY1H RNA binding motif . . . [GeneID: 5944] | 139: TDRKH tudor and KH doma . . . [GeneID: 11022] | 140: RKHD1 ring finger and K . . . [GeneID: 399664] |
| 141: DAZL deleted in azoosp . . . [GeneID: 1618] | 142: RBMY2BP RNA binding motif . . . [GeneID: 375850] | 143: ADAR adenosine deamina . . . [GeneID: 103] | 144: SFRS7 splicing factor, . . . [GeneID: 6432] |
| 145: SERBP1 SERPINE1 mRNA bin . . . [GeneID: 26135] | 146: SRRM2 serine/arginine r . . . [GeneID: 23524] | 147: STAU2 staufen, RNA bind . . . [GeneID: 27067] | 148: ZFR zinc finger RNA b . . . [GeneID: 51663] |

TABLE 2-continued

Representative RNA Binding Protiens Regulating Pathophysiological Conditions

| | | | |
|---|---|---|---|
| 149: RBMY1JRNA binding motif . . . [GeneID: 378951] | 150: RBMY1E RNA binding motif . . . [GeneID: 378950] | 151: RBMY1D RNA binding motif . . . [GeneID: 378949] | 152: RBMY1B RNA binding motif . . . [GeneID: 378948] |
| 153: RBMXL1 RNA binding motif . . . [GeneID: 494115] | 154: RBM20 RNA binding motif . . . [GeneID: 282996] | 155: RBM22P1 RNA binding motif . . . [GeneID: 406880] | 156: RBMY2CP RNA binding motif . . . [GeneID: 140123] |
| 157: RBMY2MP RNA binding motif . . . [GeneID: 140101] | 158: RBMY2KP RNA binding motif . . . [GeneID: 140100] | 159: RBM8B RNA binding motif . . . [GeneID: 112846] | 160: LOC731568 similar to RNA bi . . . [GeneID: 731568] |
| 161: RBM similar to RNA bi . . . [GeneID: 650805] | 162: RBMY3AP RNA binding motif . . . [GeneID: 64593] | 163: HNRPDL heterogeneous nuc . . . [GeneID: 9987] | 164: RBMY2YP RNA binding motif . . . [GeneID: 379024] |
| 165: RBMY2XP RNA binding motif . . . [GeneID: 379012] | 166: RBMY2WP RNA binding motif . . . [GeneID: 379011] | 167: RBMY2VP RNA binding motif . . . [GeneID: 379010] | 168: RBMY2UP RNA binding motif . . . [GeneID: 379009] |
| 169: RBMY2TP RNA binding motif . . . [GeneID: 379008] | 170: RBMY2SP RNA binding motif . . . [GeneID: 379007] | 171: RBMY2QP RNA binding motif . . . [GeneID: 379006] | 172: RBMY2OP RNA binding motif . . . [GeneID: 379005] |
| 173: RBPMSLP RNA binding prote . . . [GeneID: 54032] | 174: RBMY2AP RNA binding motif . . . [GeneID: 5945] | 175: RBMS1P RNA binding motif . . . [GeneID: 5938] | 176: LOC645420 similar to RNA bi . . . [GeneID: 645420] |
| 177: RBMXP2 RNA binding motif . . . [GeneID: 441391] | 178: RBMY2NP RNA binding motif . . . [GeneID: 378956] | 179: RBMY2JP RNA binding motif . . . [GeneID: 378955] | 180: RBMY2HP RNA binding motif . . . [GeneID: 378953] |
| 181: RBMY2GP RNA binding motif . . . [GeneID: 378952] | 182: RBMY1A3P RNA binding motif . . . [GeneID: 286557] | 183: RBMY2FP RNA binding motif . . . [GeneID: 159162] | 184: RBMY2EP RNA binding motif . . . [GeneID: 159125] |
| 185: RBMXP1 RNA binding motif . . . [GeneID: 3186] | 186: RBMY2DP RNA binding motif . . . [GeneID: 347598] | 187: HNRPDP heterogeneous nuc . . . [GeneID: 8251] | 188: LOC728303 similar to zinc f . . . [GeneID: 728303] |
| 189: TARBP2P Tar (HIV-1) RNA b . . . [GeneID: 6896] | 190: LOC650253 similar to RNA bi . . . [GeneID: 650253] | 191: SRP14P1 signal recognitio . . . [GeneID: 390284] | 192: LOC730732 similar to zinc f . . . [GeneID: 730732] |
| 193: LOC643494 similar to RNA bi . . . [GeneID: 643494] | 194: LOC643427 similar to RNA bi . . . [GeneID: 643427] | 195: LOC391136 RNA binding motif . . . [GeneID: 391136] | 196: LOC644509 similar to RNA bi . . . [GeneID: 644509] |
| 197: LOC646755 similar to RNA bi . . . [GeneID: 646755] | 198: LOC143543 RNA binding motif . . . [GeneID: 143543] | 199: ATF1 activating transc . . . [GeneID: 466] | 200: CCBL2 cysteine conjugat . . . [GeneID: 56267] |
| 201: LOC651594 similar to RNA bi . . . [GeneID: 651594] | 202: LOC643762 similar to RNA bi . . . [GeneID: 643762] | 203: LOC642389 similar to RNA bi . . . [GeneID: 642389] | 204: LOC642247 similar to RNA bi . . . [GeneID: 642247] |
| 205: EXOSC1 exosome component 1 [GeneID: 51013] | 206: PCBP2 poly(rC) binding . . . [GeneID: 5094] | 207: HNRPK heterogeneous nuc . . . [GeneID: 3190] | 208: IGF2BP3 insulin-like grow . . . [GeneID: 10643] |
| 209: PCBP3 poly(rC) binding . . . [GeneID: 54039] | 210: ADARB2 adenosine deamina . . . [GeneID: 105] | 211: ROD1 ROD1 regulator of . . . [GeneID: 9991] | 212: DAZ1 deleted in azoosp . . . [GeneID: 1617] |
| 213: MKI67IP MKI67 (FHA domain . . . [GeneID: 84365] | 214: RPS14 ribosomal protein . . . [GeneID: 6208] | 215: PPARGC1B peroxisome prolif . . . [GeneID: 133522] | 216: RPS2 ribosomal protein S2 [GeneID: 6187] |
| 217: NPM1 nucleophosmin (nu . . . [GeneID: 4869] | 218: ELAVL4 ELAV (embryonic l . . . [GeneID: 1996] | 219: HNRPL heterogeneous nuc . . . [GeneID: 3191] | 220: TROVE2 TROVE domain fami . . . [GeneID: 6738] |
| 221: SRP54 signal recognitio . . . [GeneID: 6729] | 222: SRP9 signal recognitio . . . [GeneID: 6726] | 223: EXOSC9 exosome component 9 [GeneID: 5393] | 224: SRrp35 serine-arginine r . . . [GeneID: 135295] |
| 225: ACO1 aconitase 1, soluble [GeneID: 48] | 226: ACF apobec-1 compleme . . . [GeneID: 29974] | 227: FMR1 fragile X mental . . . [GeneID: 2332] | 228: LARP1 La ribonucleoprot . . . [GeneID: 23367] |
| 229: PCBP1 poly(rC) binding . . . [GeneID: 5093] | 230: BICC1 bicaudal C homolo . . . [GeneID: 80114] | 231: IGF2BP2 insulin-like grow . . . [GeneID: 10644] | 232: FXR1 fragile X mental . . . [GeneID: 8087] |
| 233: SF1 splicing factor 1 [GeneID: 7536] | 234: FXR2 fragile X mental . . . [GeneID: 9513] | 235: EIF2AK2 eukaryotic transl . . . [GeneID: 5610] | 236: IGF2BP1 insulin-like grow . . . [GeneID: 10642] |
| 237: LARP4 La ribonucleoprot . . . [GeneID: 113251] | 238: PNPT1 polyribonucleotid . . . [GeneID: 87178] | 239: HTF9C HpaII tiny fragme . . . [GeneID: 27037] | 240: PABPC4 poly(A) binding p . . . [GeneID: 8761] |
| 241: NOVA2 neuro-oncological . . . [GeneID: 4858] | 242: TTC14 tetratricopeptide . . . [GeneID: 151613] | 243: LARP7 La ribonucleoprot . . . [GeneID: 51574] | 244: PDCD11 programmed cell d . . . [GeneID: 22984] |
| 245: EWSR1 Ewing sarcoma bre . . . [GeneID: 2130] | 246: KHSRP KH-type splicing . . . [GeneID: 8570] | 247: MATR3 matrin 3 [GeneID: 9782] | 248: ELAVL3 ELAV (embryonic l . . . [GeneID: 1995] |
| 249: ELAVL2 ELAV (embryonic l . . . [GeneID: 1993] | 250: LGTN ligatin [GeneID: 1939] | 251: PUM1 pumilio homolog 1 . . . [GeneID: 9698] | 252: HNRPU heterogeneous nuc . . . [GeneID: 3192] |
| 253: HNRPA2B1 | 254: PABPC5 poly(A) | 255: HDLBP high density | 256: EXOSC3 exosome |

TABLE 2-continued

Representative RNA Binding Protiens Regulating Pathophysiological Conditions

| | | | |
|---|---|---|---|
| heterogeneous nuc . . . [GeneID: 3181] | binding p . . . [GeneID: 140886] | lipo . . . [GeneID: 3069] | component 3 [GeneID: 51010] |
| 257: DDX1 DEAD (Asp-Glu-Ala . . . [GeneID: 1653] | 258: POLR2G polymerase (RNA) . . . [GeneID: 5436] | 259: SNRP70 small nuclear rib . . . [GeneID: 6625] | 260: CSTF3 cleavage stimulat . . . [GeneID: 1479] |
| 261: ZNF638 zinc finger prote . . . [GeneID: 27332] | 262: PPIE peptidylprolyl is . . . [GeneID: 10450] | 263: ADARB1 adenosine deamina . . . [GeneID: 104] | 264: DAZ4 deleted in azoosp . . . [GeneID: 57135] |
| 265: SFRS6 splicing factor, . . . [GeneID: 6431] | 266: FUS fusion (involved . . . [GeneID: 2521] | 267: PAPOLG poly(A) polymeras . . . [GeneID: 64895] | 268: DAZ3 deleted in azoosp . . . [GeneID: 57054] |
| 269: DDX28 DEAD (Asp-Glu-Ala . . . [GeneID: 55794] | 270: CSTF2T cleavage stimulat . . . [GeneID: 23283] | 271: SF3A1 splicing factor 3 . . . [GeneID: 10291] | 272: HNRPR heterogeneous nuc . . . [GeneID: 10236] |
| 273: PABPC3 poly(A) binding p . . . [GeneID: 5042] | 274: PA2G4 proliferation-ass . . . [GeneID: 5036] | 275: BOLL bol, boule-like ( . . . [GeneID: 66037] | 276: PAPOLB poly(A) polymeras . . . [GeneID: 56903] |
| 277: G3BP1 GTPase activating . . . [GeneID: 10146] | 278: XPO1 exportin 1 (CRM1 . . . [GeneID: 7514] | 279: PABPC1 poly(A) binding p . . . [GeneID: 26986] | 280: U2AF2 U2 small nuclear . . . [GeneID: 11338] |
| 281: RPS3 ribosomal protein S3 [GeneID: 6188] | 282: RPL7A ribosomal protein . . . [GeneID: 6130] | 283: RC3H1 ring finger and C . . . [GeneID: 149041] | 284: PPIL4 peptidylprolyl is . . . [GeneID: 85313] |
| 285: KIAA0020 KIAA0020 [GeneID: 9933] | 286: RNASEL ribonuclease L (2 . . . [GeneID: 6041] | 287: DDX53 DEAD (Asp-Glu-Ala . . . [GeneID: 168400] | 288: LARP6 La ribonucleoprot . . . [GeneID: 55323] |
| 289: HNRPUL1 heterogeneous nuc . . . [GeneID: 11100] | 290: HNRPM heterogeneous nuc . . . [GeneID: 4670] | 291: FBL fibrillarin [GeneID: 2091] | 292: TLR8 toll-like receptor 8 [GeneID: 51311] |
| 293: CPSF6 cleavage and poly . . . [GeneID: 11052] | 294: NUDT21 nudix (nucleoside . . . [GeneID: 11051] | 295: SART3 squamous cell car . . . [GeneID: 9733] | 296: EIF2S1 eukaryotic transl . . . [GeneID: 1965] |
| 297: TLR7 toll-like receptor 7 [GeneID: 51284] | 298: DAZAP1 DAZ associated pr . . . [GeneID: 26528] | 299: HNRPA0 heterogeneous nuc . . . [GeneID: 10949] | 300: PAPOLA poly(A) polymeras . . . [GeneID: 10914] |
| 301: TLR3 toll-like receptor 3 [GeneID: 7098] | 302: HNRPH3 heterogeneous nuc . . . [GeneID: 3189] | 303: HNRPH2 heterogeneous nuc . . . [GeneID: 3188] | 304: HNRPH1 heterogeneous nuc . . . [GeneID: 3187] |
| 305: HNRPF heterogeneous nuc . . . [GeneID: 3185] | 306: HNRPC heterogeneous nuc . . . [GeneID: 3183] | 307: HNRPA1 heterogeneous nuc . . . [GeneID: 3178] | 308: MASK-BP3 MASK-4E-BP3 alter . . . [GeneID: 404734] |
| 309: MCTS1 malignant T cell . . . [GeneID: 28985] | 310: ZNF239 zinc finger prote . . . [GeneID: 8187] | 311: AKAP1 A kinase (PRKA) a . . . [GeneID: 8165] | 312: SUPT6H suppressor of Ty . . . [GeneID: 6830] |
| 313: DHX8 DEAH (Asp-Glu-Ala . . . [GeneID: 1659] | 314: DDX3X DEAD (Asp-Glu-Ala . . . [GeneID: 1654] | 315: CPEB2 cytoplasmic polya . . . [GeneID: 132864] | 316: ANKHD1 ankyrin repeat an . . . [GeneID: 54882] |
| 317: SRP68 signal recognitio . . . [GeneID: 6730] | 318: NANOS1 nanos homolog 1 ( . . . [GeneID: 340719] | 319: A2BP1 ataxin 2-binding . . . [GeneID: 54715] | 320: DDX58 DEAD (Asp-Glu-Ala . . . [GeneID: 23586] |
| 321: CHERP calcium homeostas . . . [GeneID: 10523] | 322: SMN1 survival of motor . . . [GeneID: 6606] | 323: CSTF2 cleavage stimulat . . . [GeneID: 1478] | 324: NANOS2 nanos homolog 2 ( . . . [GeneID: 339345] |
| 325: NSUN6 NOL1/NOP2/Sun dom . . . [GeneID: 221078] | 326: NXF5 nuclear RNA expor . . . [GeneID: 55998] | 327: TARDBP TAR DNA binding p . . . [GeneID: 23435] | 328: LOC729293 similar to riboso . . . [GeneID: 729293] |
| 329: LOC401622 similar to LINE-1 . . . [GeneID: 401622] | 330: HNRPA3 heterogeneous nuc . . . [GeneID: 220988] | 331: RPUSD1 RNA pseudouridyla . . . [GeneID: 113000] | 332: RG9MTD2 RNA (guanine-9-) . . . [GeneID: 93587] |
| 333: MRPS5 mitochondrial rib . . . [GeneID: 64969] | 334: THOC2 THO complex 2 [GeneID: 57187] | 335: DDX49 DEAD (Asp-Glu-Ala . . . [GeneID: 54555] | 336: EXOSC4 exosome component 4 [GeneID: 54512] |
| 337: TRA2A transformer-2 alpha [GeneID: 29896] | 338: CPSF1 cleavage and poly . . . [GeneID: 29894] | 339: LSM3 LSM3 homolog, U6 . . . [GeneID: 27258] | 340: PDCD4 programmed cell d . . . [GeneID: 27250] |
| 341: THUMPD3 THUMP domain cont . . . [GeneID: 25917] | 342: PUM2 pumilio homolog 2 . . . [GeneID: 23369] | 343: SR140 U2-associated SR1 . . . [GeneID: 23350] | 344: EIF1AY eukaryotic transl . . . [GeneID: 9086] |
| 345: RPL14 ribosomal protein . . . [GeneID: 9045] | 346: SKIV2L superkiller viral . . . [GeneID: 6499] | 347: SFRS8 splicing factor, . . . [GeneID: 6433] | 348: SFRS5 splicing factor, . . . [GeneID: 6430] |
| 349: SFRS3 splicing factor, . . . [GeneID: 6428] | 350: SFRS2 splicing factor, . . . [GeneID: 6427] | 351: SFRS1 splicing factor, . . . [GeneID: 6426] | 352: SFPQ splicing factor p . . . [GeneID: 6421] |
| 353: LOC730445 similar to riboso . . . [GeneID: 730445] | 354: LOC440589 similar to riboso . . . [GeneID: 440589] | 355: LOC345630 similar to fibril . . . [GeneID: 345630] | 356: HNRPCL1 heterogeneous nuc . . . [GeneID: 343069] |

TABLE 2-continued

Representative RNA Binding Protiens Regulating Pathophysiological Conditions

| | | | |
|---|---|---|---|
| 357: EIF4E1B eukaryotic transl . . . [GeneID: 253314] | 358: LOC132430 similar to poly(A . . . [GeneID: 132430] | 359: RAVER1 ribonucleoprotein . . . [GeneID: 125950] | 360: THOC3 THO complex 3 [GeneID: 84321] |
| 361: DDX24 DEAD (Asp-Glu-Ala . . . [GeneID: 57062] | 362: XRN1 5'-3' exoribonucl . . . [GeneID: 54464] | 363: MOV10L1 Mov10l1, Moloney . . . [GeneID: 54456] | 364: RNUXA RNA U, small nucl . . . [GeneID: 51808] |
| 365: LSM4 LSM4 homolog, U6 . . . [GeneID: 25804] | 366: NOL3 nucleolar protein . . . [GeneID: 8996] | 367: ZNF74 zinc finger prote . . . [GeneID: 7625] | 368: ATXN1 ataxin 1 [GeneID: 6310] |
| 369: SARS seryl-tRNA synthe . . . [GeneID: 6301] | 370: PARN poly(A)-specific . . . [GeneID: 5073] | 371: NANOS3 nanos homolog 3 ( . . . [GeneID: 342977] | 372: MGC11102 hypothetical prot . . . [GeneID: 84285] |
| 373: C1orf25 chromosome 1 open . . . [GeneID: 81627] | 374: FIP1L1 FIP1 like 1 (S. c . . . [GeneID: 81608] | 375: C20orfl9 chromosome 20 ope . . . [GeneID: 80336] | 376: CPEB4 cytoplasmic polya . . . [GeneID: 80315] |
| 377: SECISBP2 SECIS binding pro . . . [GeneID: 79048] | 378: DDX54 DEAD (Asp-Glu-Ala . . . [GeneID: 79039] | 379: DDX50 DEAD (Asp-Glu-Ala . . . [GeneID: 79009] | 380: EXOSC5 exosome component 5 [GeneID: 56915] |
| 381: TRMT1 TRM1 tRNA methylt . . . [GeneID: 55621] | 382: RPUSD2 RNA pseudouridyla . . . [GeneID: 27079] | 383: THOC4 THO complex 4 [GeneID: 10189] | 384: SFRS14 splicing factor, . . . [GeneID: 10147] |
| 385: LRPPRC leucine-rich PPR- . . . [GeneID: 10128] | 386: EIF2S2 eukaryotic transl . . . [GeneID: 8894] | 387: DDX18 DEAD (Asp-Glu-Ala . . . [GeneID: 8886] | 388: SYNJ2 synaptojanin 2 [GeneID: 8871] |
| 389: SYNJ1 synaptojanin 1 [GeneID: 8867] | 390: SAFB scaffold attachme . . . [GeneID: 6294] | 391: RPS29 ribosomal protein . . . [GeneID: 6235] | 392: RPS27 ribosomal protein . . . [GeneID: 6232] |
| 393: RPS26 ribosomal protein . . . [GeneID: 6231] | 394: RPS25 ribosomal protein . . . [GeneID: 6230] | 395: RPS24 ribosomal protein . . . [GeneID: 6229] | 396: RPS23 ribosomal protein . . . [GeneID: 6228] |
| 397: RPS21 ribosomal protein . . . [GeneID: 6227] | 398: RPS20 ribosomal protein . . . [GeneID: 6224] | 399: RPS19 ribosomal protein . . . [GeneID: 6223] | 400: RPS17 ribosomal protein . . . [GeneID: 6218] |
| 401: RPS15A ribosomal protein . . . [GeneID: 6210] | 402: RPS13 ribosomal protein . . . [GeneID: 6207] | 403: RPS12 ribosomal protein . . . [GeneID: 6206] | 404: RPS10 ribosomal protein . . . [GeneID: 6204] |
| 405: RPS8 ribosomal protein S8 [GeneID: 6202] | 406: RPS7 ribosomal protein S7 [GeneID: 6201] | 407: OAS3 2'-5'-oligoadenyl . . . [GeneID: 4940] | 408: OAS2 2'-5'-oligoadenyl . . . [GeneID: 4939] |
| 409: OAS1 2',5'-oligoadenyl . . . [GeneID: 4938] | 410: YBX1 Y box binding pro . . . [GeneID: 4904] | 411: ISG20 interferon stimul . . . [GeneID: 3669] | 412: IREB2 iron-responsive e . . . [GeneID: 3658] |
| 413: LOC650901 similar to riboso . . . [GeneID: 650901] | 414: RG9MTD3 RNA (guanine-9-) . . . [GeneID: 158234] | 415: PRIC285 peroxisomal proli . . . [GeneID: 85441] | 416: PTBP2 polypyrimidine tr . . . [GeneID: 58155] |
| 417: DDX43 DEAD (Asp-Glu-Ala . . . [GeneID: 55510] | 418: CPSF3 cleavage and poly . . . [GeneID: 51692] | 419: LSM8 LSM8 homolog, U6 . . . [GeneID: 51691] | 420: LSM7 LSM7 homolog, U6 . . . [GeneID: 51690] |
| 421: SF3B14 splicing factor 3 . . . [GeneID: 51639] | 422: FNBP1 formin binding pr . . . [GeneID: 23048] | 423: EXOSC7 exosome component 7 [GeneID: 23016] | 424: SPEN spen homolog, tra . . . [GeneID: 23013] |
| 425: EXOSC8 exosome component 8 [GeneID: 11340] | 426: RNMT RNA (guanine-7-) . . . [GeneID: 8731] | 427: NOL4 nucleolar protein 4 [GeneID: 8715] | 428: EIF4H eukaryotic transl . . . [GeneID: 7458] |
| 429: RPS6 ribosomal protein S6 [GeneID: 6194] | 430: RPS5 ribosomal protein S5 [GeneID: 6193] | 431: RPS3A ribosomal protein . . . [GeneID: 6189] | 432: RPN1 ribophorin I [GeneID: 6184] |
| 433: MRPL12 mitochondrial rib . . . [GeneID: 6182] | 434: RPLP2 ribosomal protein . . . [GeneID: 6181] | 435: RPLP1 ribosomal protein . . . [GeneID: 6176] | 436: RPLP0 ribosomal protein . . . [GeneID: 6175] |
| 437: RPL41 ribosomal protein . . . [GeneID: 6171] | 438: RPL39 ribosomal protein . . . [GeneID: 6170] | 439: RPL38 ribosomal protein . . . [GeneID: 6169] | 440: RPL34 ribosomal protein . . . [GeneID: 6164] |
| 441: RPL31 ribosomal protein . . . [GeneID: 6160] | 442: RPL29 ribosomal protein . . . [GeneID: 6159] | 443: RPL28 ribosomal protein . . . [GeneID: 6158] | 444: RPL27A ribosomal protein . . . [GeneID: 6157] |
| 445: RPL30 ribosomal protein . . . [GeneID: 6156] | 446: RPL26 ribosomal protein . . . [GeneID: 6154] | 447: RPL24 ribosomal protein . . . [GeneID: 6152] | 448: MRPL23 mitochondrial rib . . . [GeneID: 6150] |
| 449: RPL22 ribosomal protein . . . [GeneID: 6146] | 450: RPL21 ribosomal protein . . . [GeneID: 6144] | 451: RPL19 ribosomal protein . . . [GeneID: 6143] | 452: RPL18A ribosomal protein . . . [GeneID: 6142] |
| 453: RPL18 ribosomal protein . . . [GeneID: 6141] | 454: RPL17 ribosomal protein . . . [GeneID: 6139] | 455: RPL15 ribosomal protein . . . [GeneID: 6138] | 456: RPL13 ribosomal protein . . . [GeneID: 6137] |
| 457: RPL12 ribosomal protein . . . [GeneID: 6136] | 458: RPL9 ribosomal protein L9 [GeneID: 6133] | 459: RPL7 ribosomal protein L7 [GeneID: 6129] | 460: RPL6 ribosomal protein L6 [GeneID: 6128] |
| 461: RPL4 ribosomal protein L4 [GeneID: 6124] | 462: RPL3L ribosomal protein . . . [GeneID: 6123] | 463: CNOT4 CCR4-NOT transcri . . . [GeneID: 4850] | 464: CDC5L CDC5 cell divisio . . . [GeneID: 988] |
| 465: FLJ45950 FLJ45950 protein [GeneID: 399975] | 466: U2AF1L4 U2 small nuclear . . . [GeneID: 199746] | 467: DCP2 DCP2 decapping en . . . [GeneID: 167227] | 468: DIS3L2 DIS3 mitotic cont . . . [GeneID: 129563] |

TABLE 2-continued

Representative RNA Binding Protiens Regulating Pathophysiological Conditions

| | | | |
|---|---|---|---|
| 469: ALKBH8 alkB, alkylation . . . [GeneID: 91801] | 470: CPEB1 cytoplasmic polya . . . [GeneID: 64506] | 471: DDX19B DEAD (Asp-Glu-Ala . . . [GeneID: 11269] | 472: MRPL3 mitochondrial rib . . . [GeneID: 11222] |
| 473: THOC1 THO complex 1 [GeneID: 9984] | 474: G3BP2 GTPase activating . . . [GeneID: 9908] | 475: SFRS9 splicing factor, . . . [GeneID: 8683] | 476: EIF4G3 eukaryotic transl . . . [GeneID: 8672] |
| 477: EIF3S9 eukaryotic transl . . . [GeneID: 8662] | 478: DDX3Y DEAD (Asp-Glu-Ala . . . [GeneID: 8653] | 479: RNASET2 ribonuclease T2 [GeneID: 8635] | 480: RTCD1 RNA terminal phos . . . [GeneID: 8634] |
| 481: U2AF1 U2 small nuclear . . . [GeneID: 7307] | 482: RNASE1 ribonuclease, RNa . . . [GeneID: 6035] | 483: FAU Finkel-Biskis-Rei . . . [GeneID: 2197] | 484: ETF1 eukaryotic transl . . . [GeneID: 2107] |
| 485: LOC646804 similar to CG1780 . . . [GeneID: 646804] | 486: DND1 dead end homolog . . . [GeneID: 373863] | 487: THEX1 three prime histo . . . [GeneID: 90459] | 488: NOM1 nucleolar protein . . . [GeneID: 64434] |
| 489: DDX19A DEAD (Asp-Glu-Ala . . . [GeneID: 55308] | 490: DDX41 DEAD (Asp-Glu-Ala . . . [GeneID: 51428] | 491: NUFIP1 nuclear fragile X . . . [GeneID: 26747] | 492: DIS3 DIS3 mitotic cont . . . [GeneID: 22894] |
| 493: CPEB3 cytoplasmic polya . . . [GeneID: 22849] | 494: LSM6 LSM6 homolog, U6 . . . [GeneID: 11157] | 495: DSCR1L2 Down syndrome cri . . . [GeneID: 11123] | 496: RPP14 ribonuclease P 14 . . . [GeneID: 11102] |
| 497: DDX46 DEAD (Asp-Glu-Ala . . . [GeneID: 9879] | 498: KIAA0427 KIAA0427 [GeneID: 9811] | 499: TSN translin [GeneID: 7247] | 500: UPF1 UPF1 regulator of . . . [GeneID: 5976] |
| 501: NCL nucleolin [GeneID: 4691] | 502: ERVK2 endogenous retrov . . . [GeneID: 2087] | 503: LOC650638 similar to signal . . . [GeneID: 650638] | 504: RPUSD3 RNA pseudouridyla . . . [GeneID: 285367] |
| 505: JAKMIP1 janus kinase and . . . [GeneID: 152789] | 506: HNRPLL heterogeneous nuc . . . [GeneID: 92906] | 507: MRM1 mitochondrial rRN . . . [GeneID: 79922] | 508: APOBEC3G apolipoprotein B . . . [GeneID: 60489] |
| 509: LSM2 LSM2 homolog, U6 . . . [GeneID: 57819] | 510: RAVER2 ribonucleoprotein . . . [GeneID: 55225] | 511: CPSF2 cleavage and poly . . . [GeneID: 53981] | 512: NIP7 nuclear import 7 . . . [GeneID: 51388] |
| 513: DDX52 DEAD (Asp-Glu-Ala . . . [GeneID: 11056] | 514: EIF4A3 eukaryotic transl . . . [GeneID: 9775] | 515: SETD1A SET domain contai . . . [GeneID: 9739] | 516: AQR aquarius homolog . . . [GeneID: 9716] |
| 517: DHX34 DEAH (Asp-Glu-Ala . . . [GeneID: 9704] | 518: RAE1 RAE1 RNA export 1 . . . [GeneID: 8480] | 519: DUSP11 dual specificity . . . [GeneID: 8446] | 520: HSP90B1 heat shock protei . . . [GeneID: 7184] |
| 521: HRB HIV-1 Rev binding . . . [GeneID: 3267] | 522: EIF4G2 eukaryotic transl . . . [GeneID: 1982] | 523: EIF4G1 eukaryotic transl . . . [GeneID: 1981] | 524: EIF4B eukaryotic transl . . . [GeneID: 1975] |
| 525: EIF4A2 eukaryotic transl . . . [GeneID: 1974] | 526: EIF1AX eukaryotic transl . . . [GeneID: 1964] | 527: BFSP1 beaded filament s . . . [GeneID: 631] | 528: DDX51 DEAD (Asp-Glu-Ala . . . [GeneID: 317781] |
| 529: RNASEH1 ribonuclease H1 [GeneID: 246243] | 530: UHMK1 U2AF homology mot . . . [GeneID: 127933] | 531: hCG__1992539 hCG1992539 [GeneID: 91561] | 532: FLJ12529 pre-mRNA cleavage . . . [GeneID: 79869] |
| 533: KIAA1604 KIAA1604 protein [GeneID: 57703] | 534: DNAJC17 DnaJ (Hsp40) homo . . . [GeneID: 55192] | 535: RNMTL1 RNA methyltransfe . . . [GeneID: 55178] | 536: PAPD1 PAP associated do . . . [GeneID: 55149] |
| 537: FLJ10292 mago-nashi homolog 2 [GeneID: 55110] | 538: SCAND1 SCAN domain conta . . . [GeneID: 51282] | 539: DDX25 DEAD (Asp-Glu-Ala . . . [GeneID: 29118] | 540: APOBEC2 apolipoprotein B . . . [GeneID: 10930] |
| 541: SAFB2 scaffold attachme . . . [GeneID: 9667] | 542: DZIP3 zinc finger DAZ i . . . [GeneID: 9666] | 543: TERT telomerase revers . . . [GeneID: 7015] | 544: TEP1 telomerase-associ . . . [GeneID: 7011] |
| 545: BARD1 BRCA1 associated . . . [GeneID: 580] | 546: LOC651789 similar to poly(A . . . [GeneID: 651789] | 547: LOC649163 similar to Splici . . . [GeneID: 649163] | 548: EIF4E3 eukaryotic transl . . . [GeneID: 317649] |
| 549: CNOT6L CCR4-NOT transcri . . . [GeneID: 246175] | 550: LSM11 LSM11, U7 small n . . . [GeneID: 134353] | 551: LSM10 LSM10, U7 small n . . . [GeneID: 84967] | 552: ZBP1 Z-DNA binding pro . . . [GeneID: 81030] |
| 553: IFIH1 interferon induce . . . [GeneID: 64135] | 554: DDX55 DEAD (Asp-Glu-Ala . . . [GeneID: 57696] | 555: METTL3 methyltransferase . . . [GeneID: 56339] | 556: MRPL20 mitochondrial rib . . . [GeneID: 55052] |
| 557: C14orf102 chromosome 14 ope . . . [GeneID: 55051] | 558: CCDC40 coiled-coil domai . . . [GeneID: 55036] | 559: NOL8 nucleolar protein 8 [GeneID: 55035] | 560: CPSF4 cleavage and poly . . . [GeneID: 10898] |
| 561: PPARGC1A peroxisome prolif . . . [GeneID: 10891] | 562: PSMA6 proteasome (proso . . . [GeneID: 5687] | 563: PSMA1 proteasome (proso . . . [GeneID: 5682] | 564: TRDMT1 tRNA aspartic aci . . . [GeneID: 1787] |
| 565: DKC1 dyskeratosis cong . . . [GeneID: 1736] | 566: LOC645139 similar to poly(A . . . [GeneID: 645139] | 567: FLJ45337 FLJ45337 protein [GeneID: 400754] | 568: TIMM50 translocase of in . . . [GeneID: 92609] |
| 569: RPUSD4 RNA pseudouridyla . . . [GeneID: 84881] | 570: ERVK6 endogenous retrov . . . [GeneID: 64006] | 571: NUFIP2 nuclear fragile X . . . [GeneID: 57532] | 572: LOC56251 hypothetical prot . . . [GeneID: 56251] |

TABLE 2-continued

Representative RNA Binding Protiens Regulating Pathophysiological Conditions

| | | | |
|---|---|---|---|
| 573: RG9MTD1 RNA (guanine-9-) . . . [GeneID: 54931] | 574: RPP25 ribonuclease P 25 . . . [GeneID: 54913] | 575: MRPS28 mitachondrial rib . . . [GeneID: 28957] | 576: POP4 processing of pre . . . [GeneID: 10775] |
| 577: ZRANB2 zinc finger, RAN- . . . [GeneID: 9406] | 578: PABPN1 poly(A) binding p . . . [GeneID: 8106] | 579: SURF6 surfeit 6 [GeneID: 6838] | 580: SUPV3L1 suppressor of var . . . [GeneID: 6832] |
| 581: PPP1R10 protein phosphata . . . [GeneID: 5514] | 582: PPP1R8 protein phosphata . . . [GeneID: 5511] | 583: CTAGE5 CTAGE family, mem . . . [GeneID: 4253] | 584: MEF2D MADS box transcri . . . [GeneID: 4209] |
| 585: GTF3A general transcrip . . . [GeneID: 2971] | 586: DDX11 DEAD/H (Asp-Glu-A . . . [GeneID: 1663] | 587: DDX10 DEAD (Asp-Glu-Ala . . . [GeneID: 1662] | 588: DDX6 DEAD (Asp-Glu-Ala . . . [GeneID: 1656] |
| 589: DDX5 DEAD (Asp-Glu-Ala . . . [GeneID: 1655] | 590: APOBEC1 apolipoprotein B . . . [GeneID: 339] | 591: MGC70863 similar to RPL23A . . . [GeneID: 284942] | 592: MGC27348 ribosomal protein . . . [GeneID: 256355] |
| 593: MRPL21 mitochandrial rib . . . [GeneID: 219927] | 594: C14orf21 chromosome 14 ope . . . [GeneID: 161424] | 595: CNOT6 CCR4-NOT transcri . . . [GeneID: 57472] | 596: SFRS15 splicing factor, . . . [GeneID: 57466] |
| 597: MIF4GD MIF4G domain cont . . . [GeneID: 57409] | 598: GALNT8 UDP-N-acetyl-alph . . . [GeneID: 26290] | 599: ERAL1 Era G-protein-lik . . . [GeneID: 26284] | 600: LSM5 LSM5 homolog, U6 . . . [GeneID: 23658] |
| 601: RAD51AP1 RAD51 associated . . . [GeneID: 10635] | 602: PAIP1 poly(A) binding p . . . [GeneID: 10605] | 603: TPIM21 tripartite motif- . . . [GeneID: 6737] | 604: SRPR signal recognitio . . . [GeneID: 6734] |
| 605: POU6F1 POU domain, class . . . [GeneID: 5463] | 606: MAZ MYC-associated zi . . . [GeneID: 4150] | 607: MAGOH mago-nashi homolo . . . [GeneID: 4116] | 608: hCG__20417 mitochondrial rib . . . [GeneID: 642393] |
| 609: EXOSC6 exosome component 6 [GeneID: 118460] | 610: UPF3A UPF3 regulator of . . . [GeneID: 65110] | 611: UPF3B UPF3 regulator of . . . [GeneID: 65109] | 612: NXF2 nuclear RNA expor . . . [GeneID: 56001] |
| 613: MYEF2 myelin expression . . . [GeneID: 50804] | 614: ADAT1 adenosine deamina . . . [GeneID: 23536] | 615: RNASEH2A ribonuclease H2, . . . [GeneID: 10535] | 616: NOL5A nucleolar protein . . . [GeneID: 10528] |
| 617: DDX17 DEAD (Asp-Glu-Ala . . . [GeneID: 10521] | 618: SFRS11 splicing factor, . . . [GeneID: 9295] | 619: BAT1 HLA-B associated . . . [GeneID: 7919] | 620: DEK DEK oncogene (DNA . . . [GeneID: 7913] |
| 621: SPI1 spleen focus form . . . [GeneID: 6688] | 622: SNRPN small nuclear rib . . . [GeneID: 6638] | 623: SNRPG small nuclear rib . . . [GeneID: 6637] | 624: SNRPF small nuclear rib . . . [GeneID: 6636] |
| 625: SNRPE small nuclear rib . . . [GeneID: 6635] | 626: SNRPD1 small nuclear rib . . . [GeneID: 6632] | 627: SNRPC small nuclear rib . . . [GeneID: 6631] | 628: SNRPB2 small nuclear rib . . . [GeneID: 6629] |
| 629: SNRPB small nuclear rib . . . [GeneID: 6628] | 630: SNRPA1 small nuclear rib . . . [GeneID: 6627] | 631: SNRPA small nuclear rib . . . [GeneID: 6626] | 632: EXOSC10 exosome component 10 [GeneID: 5394] |
| 633: CSTF1 cleavage stimulat . . . [GeneID: 1477] | 634: NR0B1 nuclear receptor . . . [GeneID: 190] | 635: DIS3L DIS3 mitotic cont . . . [GeneID: 115752] | 636: MRPL1 mitochondrial rib . . . [GeneID: 65008] |
| 637: DDX56 DEAD (Asp-Glu-Ala . . . [GeneID: 54606] | 638: APOBEC3C apolipoprotein B . . . [GeneID: 27350] | 639: CTA-126B4.3 CGI-96 protein [GeneID: 27341] | 640: HTATSF1 HIV-1 Tat specifi . . . [GeneID: 27336] |
| 641: TNRC6A trinucleotide rep . . . [GeneID: 27327] | 642: UPF2 UPF2 regulator of . . . [GeneID: 26019] | 643: SYNCRIP synaptotagmin bin . . . [GeneID: 10492] | 644: DDX21 DEAD (Asp-Glu-Ala . . . [GeneID: 9188] |
| 645: RRP9 RRP9, small subun . . . [GeneID: 9136] | 646: DHX9 DEAH (Asp-Glu-Ala . . . [GeneID: 1660] | 647: ELAVL1 ELAV (embryonic 1 . . . [GeneID: 1994] | 648: NOVA1 neuro-oncological . . . [GeneID: 4857] |
| 649: PRKRA protein kinase, i . . . [GeneID: 8575] | 650: RNASEN ribonuclease III, . . . [GeneID: 29102] | 651: DUS2L dihydrouridine sy . . . [GeneID: 54920] | 652: SON SON DNA binding p . . . [GeneID: 6651] |
| 653: EXOSC2 exosome component 2 [GeneID: 23404] | 654: MDM2 Mdm2, transformed . . . [GeneID: 4193] | 655: DGCR8 DiGeorge syndrome . . . [GeneID: 54487] | 656: CDKN2AIP CDKN2A interactin . . . [GeneID: 55602] |
| 657: ZFP36 zinc finger prote.. [GeneID: 7538] | 658: ILF2 interleukin enhan . . . [GeneID: 3608] | 659: SLC4A1AP solute carrier fa . . . [GeneID: 22950] | 660: DHX30 DEAH (Asp-Glu-Ala . . . [GeneID: 22907] |
| 661: OASL 2'-5'-oligoadenyl . . . [GeneID: 8638] | 662: DLX2 distal-less homeo . . . [GeneID: 1746] | 663: SRP19 signal recognitio . . . [GeneID: 6728] | 664: MBNL1 muscleblind-like . . . [GeneID: 4154] |
| 665: LOC643631 similar to dicer1 [GeneID: 643631] | 666: PIWIL1 piwi-like 1 (Dros . . . [GeneID: 9271] | 667: LRRFIP1 leucine rich repe . . . [GeneID: 9208] | 668: MRPL44 mitochondrial rib . . . [GeneID: 65080] |
| 669: NKRF NF-kappaB repress . . . [GeneID: 55922] | 670: DICER1 Dicer1, Dcr-1 hom . . . [GeneID: 23405] | 671: LARP1 La ribonucleoprot . . . [GeneID: 55132] | 672: ARID4A AT rich interacti . . . [GeneID: 5926] |
| 673: TP53 tumor protein p53 . . . [GeneID: 7157] | 674: PHF20L1 PHD finger protei . . . [GeneID: 51105] | 675: ZMAT1 zinc finger, matr . . . [GeneID: 84460] | 676: NOLA1 nucleolar protein . . . [GeneID: 54433] |

TABLE 2-continued

Representative RNA Binding Protiens Regulating Pathophysiological Conditions

| | | | |
|---|---|---|---|
| 677: SRRM1 serine/arginine r . . . [GeneID: 10250] | 678: CD96 CD96 molecule [GeneID: 10225] | 679: FUBP3 far upstream elem.. [GeneID: 8939] | 680: RKHD3 ring finger and K . . . [GeneID: 84206] |
| 681: ARID4B AT rich interacti . . . [GeneID: 51742] | 682: CDKN1A cyclin-dependent . . . [GeneID: 1026] | 683: RPS4X ribosomal protein . . . [GeneID: 6191] | 684: RPL8 ribosomal protein L8 [GeneID: 6132] |
| 685: UBA52 ubiquitin A-52 re . . . [GeneID: 7311] | 686: LOC390748 similar to poly(A . . . [GeneID: 390748] | 687: KRR1 KRR1, small subun . . . [GeneID: 11103] | 688: ZMAT3 zinc finger, matr . . . [GeneID: 64393] |
| 689: QARS glutaminyl-tRNA s . . . [GeneID: 5859] | 690: PRMT1 protein arginine . . . [GeneID: 3276] | 691: MSI1 musashi homolog 1 . . . [GeneID: 4440] | 692: DNAJA5 DnaJ homology sub . . . [GeneID: 134218] |
| 693: PHF19 PHD finger protei . . . [GeneID: 26147] | 694: CARHSP1 calcium regulated . . . [GeneID: 23589] | 695: MORC3 MORC family CW-ty . . . [GeneID: 23515] | 696: ANKRD17 ankyrin repeat do . . . [GeneID: 26057] |
| 697: NXF1 nuclear RNA expor . . . [GeneID: 10482] | 698: PHF1 PHD finger protein 1 [GeneID: 5252] | 699: LBR lamin B receptor [GeneID: 3930] | 700: LRP2BP LRP2 binding protein [GeneID: 55805] |
| 701: HNRNPG-T testes-specific h . . . [GeneID: 27288] | 702: ZNF385 zinc finger prote . . . [GeneID: 25946] | 703: SFRS10 splicing factor, . . . [GeneID: 6434] | 704: DAZ2 deleted in azoosp . . . [GeneID: 57055] |
| 705: SF3B4 splicing factor 3 . . . [GeneID: 10262] | 706: CPNE1 copine I [GeneID: 8904] | 707: P4HA1 procollagen-proli . . . [GeneID: 5033] | 708: MSI2 musashi homolog 2 . . . [GeneID: 124540] |
| 709: LUC7L LUC7-like (S. cer . . . [GeneID: 55692] | 710: LARP5 La ribonucleoprot . . . [GeneID: 23185] | 711: FUBP1 far upstream elem . . . [GeneID: 8880] | 712: CNBP CCHC-type zinc fi . . . [GeneID: 7555] |
| 713: S100B S100 calcium bind . . . [GeneID: 6285] | 714: CXCL10 chemokine (C-X-C . . . [GeneID: 3627] | 715: CDKN2A cyclin-dependent . . . [GeneID: 1029] | 716: LOC201181 similar to hypoth . . . [GeneID: 201181] |
| 717: TDRD3 tudor domain cont . . . [GeneID: 81550] | 718: NOLA3 nucleolar protein . . . [GeneID: 55505] | 719: JMJD2C jumonji domain co . . . [GeneID: 23081] | 720: JMJD2B jumonji domain co . . . [GeneID: 23030] |
| 721: WT1 Wilms tumor 1 [GeneID: 7490] | 722: VHL von Hippel-Lindau . . . [GeneID: 7428] | 723: NCBP2 nuclear cap bindi . . . [GeneID: 22916] | 724: EIF3S7 eukaryotic transl . . . [GeneID: 8664] |
| 725: NF2 neurofibromin 2 ( . . . [GeneID: 4771] | 726: SERF1B small EDRK-rich f . . . [GeneID: 56617] | 727: ZNF318 zinc finger prote . . . [GeneID: 24149] | 728: KIAA0907 KIAA0907 [GeneID: 22889] |
| 729: DZIP1 DAZ interacting p . . . [GeneID: 22873] | 730: MTF2 metal response el . . . [GeneID: 22823] | 731: PKP3 plakophilin 3 [GeneID: 11187] | 732: SETDB1 SET domain, bifur . . . [GeneID: 9869] |
| 733: DAZAP2 DAZ associated pr . . . [GeneID: 9802] | 734: CSDA cold shock domain . . . [GeneID: 8531] | 735: HSPA1B heat shock 70 kDa . . . [GeneID: 3304] | 736: HSPA1A heat shock 70 kDa . . . [GeneID: 3303] |
| 737: CCDC16 coiled-coil domai . . . [GeneID: 91603] | 738: BXDC2 brix domain conta . . . [GeneID: 55299] | 739: PELO pelota homolog (D . . . [GeneID: 53918] | 740: CRNKL1 crooked neck pre- . . . [GeneID: 51340] |
| 741: RKHD2 ring finger and K . . . [GeneID: 51320] | 742: TP53BP1 tumor protein p53 . . . [GeneID: 7158] | 743: PURB purine-rich eleme . . . [GeneID: 5814] | 744: PURA purine-rich eleme . . . [GeneID: 5813] |
| 745: PHF20 PHD finger protei . . . [GeneID: 51230] | 746: SFRS2B splicing factor, . . . [GeneID: 10929] | 747: FASTK Fas-activated ser . . . [GeneID: 10922] | 748: JMJD2A jumonji domain co . . . [GeneID: 9682] |
| 749: PTGS2 prostaglandin-end . . . [GeneID: 5743] | 750: SFRS12 splicing factor, . . . [GeneID: 140890] | 751: PRPF39 PRP39 pre-mRNA pr . . . [GeneID: 55015] | 752: ZNF291 zinc finger prote . . . [GeneID: 49855] |
| 753: SERF1A small EDRK-rich f . . . [GeneID: 8293] | 754: ZNF533 zinc finger prote . . . [GeneID: 151126] | 755: ZMAT4 zinc finger, matr . . . [GeneID: 79698] | 756: MRPL2 mitochondrial rib . . . [GeneID: 51069] |
| 757: ASCC1 activating signal . . . [GeneID: 51008] | 758: PRKCA protein kinase C, . . . [GeneID: 5578] | 759: ANXA2 annexin A2 [GeneID: 302] | 760: TRIT1 tRNA isopentenylt . . . [GeneID: 54802] |
| 761: SSB Sjogren syndrome . . . [GeneID: 6741] | 762: POLR2D polymerase (RNA) . . . [GeneID: 5433] | 763: PNN pinin, desmosome . . . [GeneID: 5411] | 764: ZMAT2 zinc finger, matr . . . [GeneID: 153527] |
| 765: NXF3 nuclear RNA expor . . . [GeneID: 56000] | 766: CCT4 chaperonin contai . . . [GeneID: 10575] | 767: SOLH small optic lobes . . . [GeneID: 6650] | 768: SMN2 survival of motor . . . [GeneID: 6607] |
| 769: PURG purine-rich eleme . . . [GeneID: 29942] | 770: EIF3S12 eukaryotic transl . . . [GeneID: 27335] | 771: SDCCAG1 serologically def . . . [GeneID: 9147] | 772: GARS glycyl-tRNA synth . . . [GeneID: 2617] |

IV. Detection of Nucleic Acids

Many methods for determining nucleic acid levels (i.e., for example, DNA, miRNA and/or mRNA levels) in cells from a biological sample are available. For example, a tissue sample can be provided from subjects by conventional biopsy techniques. These tissue samples may be either normal tissue, tissue that is suspected of being cancerous, or tissue that is known to be cancerous. In another example, a blood sample can be removed from the subject, and white blood cells isolated for DNA extraction by standard techniques.

Blood or tissue samples from an affected area are usually obtained from a subject known to have, or suspected of having a pathophysiological conditions before the initiation of a therapeutic treatment (i.e., for example, radiotherapy, chemotherapy or pharmaceutical treatment). A corresponding control tissue or blood sample can be obtained from unaffected tissues of the subject, from a normal human individual or population of normal individuals, or from cultured cells corresponding to the majority of cells in the subject's sample. The control tissue or blood sample may then processed along with the sample from the subject, so that the levels of nucleic acid levels from the subject's sample can be compared to the corresponding nucleic acid levels from cells of the control sample.

For example, relative miRNA levels between control and normal samples can be conveniently determined with respect to one or more RNA expression standards. The standards can comprise, for example, a zero miRNA expression level, an miRNA expression level in a standard cell line, or an average level of miRNA expression previously obtained for a population of normal human controls.

Many suitable techniques for determining the level of RNA transcripts of a particular gene in cells are available. According to one such method, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters by, e.g., the so-called "Northern" blotting technique. The RNA is then immobilized on the filters by heating. Detection and quantification of specific RNA is accomplished using appropriately labeled DNA or RNA probes complementary to the RNA in question. See, for example, In: *Molecular Cloning: A Laboratory Manual*, J. Sambrook et al., eds., 2nd edition, Cold Spring Harbor Laboratory Press, 1989, Chapter 7, the entire disclosure of which is incorporated by reference.

Suitable probes for Northern blot hybridization of a given nucleic acid can be produced from the nucleic acid sequences including, but not limited to, SEQ ID NO: 20, SEQ ID NO: 21,

```
miR-150
                                           (SEQ ID NO: 1)
CCCTGTCTCCCAACCCTTGTACCAGTGCTGGGCTCAGACCCTGGTACA

GGCCTGGGGACAGGG, mirR-186
                                           (SEQ ID NO: 2)
TGCTTGTAACTTTCGAAAGAATTCTCCTTTTGGGCTTTCTGGTTTTATTT TAAGCCCAAAGGTGAATTTTTTGGG AAGTTTGAGCT,
and, miR-186
                                           (SEQ ID NO: 3)
ACTTTCCAAAGAATTCTCCTTTTGGGCTTTCTGGTTTTATTTTAAGGCC

AAAGGTGAATTTTTTGGGAAGT.
```

Methods for preparation of labeled DNA and RNA probes, and the conditions for hybridization thereof to target nucleotide sequences are described. In: *Molecular Cloning: A Laboratory Manual*, J. Sambrook et al., eds., 2nd edition, Cold Spring Harbor Laboratory Press, 1989, Chapters 10 and 11, the disclosures of which are herein incorporated by reference.

For example, a nucleic acid probe can be labeled with, e.g., a radionuclide such as $^3H$, $^{32}P$, $^{33}P$, $^{14}C$, or $^{35}S$; a heavy metal; or a ligand capable of functioning as a specific binding pair member for a labeled ligand (i.e., for example, biotin, avidin or an antibody), a fluorescent molecule, a chemiluminescent molecule, an enzyme or the like.

Southern blot hybridization techniques may also be used to detect nucleic acids. For example, genomic DNA isolated from a subject's sample can be digested with restriction endonucleases. This digestion generates restriction fragments of the genomic DNA that can be separated by electrophoresis, for example, on an agarose gel. The restriction fragments are then blotted onto a hybridization membrane (e.g., nitrocellulose or nylon), and hybridized with labeled probes specific for a given miRNA gene or genes. A deletion or mutation of these genes is indicated by an alteration of the restriction fragment patterns on the hybridization membrane, as compared to DNA from a control sample that has been treated identically to the DNA from the subject's sample. Probe labeling and hybridization conditions suitable for detecting alterations in gene structure or sequence suitable for this technique are described herein. The miRNA gene nucleic acid probes for Southern blot hybridization can be designed based upon nucleic acid sequences including, but not limited to, SEQ ID NO: 1, SEQ ID NO: 2, SEQ ID NO: 3, SEQ ID NO: 20, and/or SEQ ID NO: 21. Nucleic acid probe hybridization can then be detected by exposing hybridized filters to photographic film, or by employing computerized imaging systems including, but not limited to, a Molecular Dynamics 400-B 2D Phosphorimager® (Amersham Biosciences, Piscataway, N.J.).

Nucleic acid probes can be labeled to high specific activity by either the nick translation method of or by the random priming method. Rigby et al., *J. Mol. Biol.* 113:237-251 (1977); and Fienberg et al., *Anal. Biochem.* 132:6-13 (1983) respectively (the entire disclosures of which are herein incorporated by reference). Feinberg et al. discloses synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of RNA transcript levels (i.e., for example, miRNA transcript levels). Using another approach, miRNA transcript levels can be quantified by computerized imaging systems using equipment including, but not limited to, Molecular Dynamics 400-B 2D Phosphorimager® (Amersham Biosciences, Piscataway, N.J.).

Where radionuclide labeling of DNA or RNA probes is not practical, the random-primer method can be used to incorporate a nucleic acid analogue (i.e., for example, a dTTP analogue 5-(N-(N-biotinyl-epsilon-aminocaproyl)-3-aminoally) deoxyuridine triphosphate) into the probe molecule. A biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA blotting hybridization techniques, determining the levels of RNA transcripts can be accomplished using the technique of in situ hybridization. U.S. Pat. No. 5,427,916 (herein incorporated by reference). This technique requires fewer cells than the Northern blotting technique, and involves depositing whole cells onto a microscope cover slip and probing the nucleic acid content of the cell with a solution containing radioactive or otherwise labeled nucleic acid (i.e., for example, cDNA or RNA)

probes. This technique is particularly well-suited for analyzing tissue biopsy samples from subjects. Suitable probes for in situ hybridization of a given miRNA can be produced from nucleic acid sequences including, but not limited to, SEQ ID NO: 1, SEQ ID NO: 2, SEQ ID NO: 3, SEQ ID NO: 20, and/or SEQ ID NO: 21.

The relative number of RNA transcripts (i.e., for example, miRNA transcripts) in cells can also be determined by reverse transcription and amplification by polymerase chain reaction (RT-PCR). The levels of RNA transcripts can be quantified in comparison with an internal standard, for example, the level of mRNA from a "housekeeping" gene present in the same sample. A suitable "housekeeping" gene for use as an internal standard includes, but is not limited to, myosin or glyceraldehyde-3-phosphate dehydrogenase (G3PDH).

In some instances, it may be desirable to simultaneously determine the expression level of a plurality of different of RNA genes in a sample. In certain instances, it may be desirable to determine the expression level of transcripts for all known miRNA genes correlated with a specific pathophysiological condition (i.e., for example, uterine cancer). Assessing cancer-specific expression levels for hundreds of miRNA genes is time consuming and requires a large amount of total RNA (at least 20 μg for each Northern blot) and autoradiographic techniques that require radioactive isotopes.

To overcome these limitations, an oligolibrary in microchip format may be constructed containing a set of probe oligonucleotides specific for a set of miRNA genes. In one embodiment, an oligolibrary contains probes corresponding to all known miRNAs from the human genome. A microchip oligolibrary may be expanded to include additional miRNAs as they are discovered. A microchip is prepared from gene-specific oligonucleotide probes generated from known miRNAs. According to one embodiment, an array comprises two different oligonucleotide probes for each miRNA. In one embodiment, the miRNA oligonucleotide probe comprises an active nucleic acid sequence. In one embodiment, the miRNA oligonucleotide probe comprises an miRNA precursor nucleic acid sequence. An array may also contain controls such as one or more mouse sequences differing from human orthologs by only a few bases, which can serve as controls for hybridization stringency conditions. Transfer RNAs (tRNAs) from different species may also be printed on the microchip, providing an internal, relatively stable positive control for specific hybridization. One or more appropriate controls for non-specific hybridization may also be included on the microchip. For this purpose, sequences are selected based upon the absence of any homology with any known miRNAs.

A microchip may be fabricated by one of several techniques. For example, probe oligonucleotides of an appropriate length (i.e., for example, 40 nucleotides), are 5'-amine modified at position C6 and printed using commercially available microarray systems (GeneMachine OmniGrid® 100 Microarrayer) and activated slides (Amersham CodeLink®). Labeled cDNA oligomer corresponding to the target RNAs may be prepared by reverse transcribing the target RNA with labeled primer. Following first strand synthesis, the RNA/DNA hybrids can be denatured to degrade the RNA templates. The labeled target cDNAs thus prepared are then hybridized to the microarray chip under hybridizing conditions (i.e., for example, 6×SSPE/30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRNAs, in the patient sample. According to one embodiment, the labeled cDNA oligomer is a biotin-labeled cDNA, prepared from a biotin-labeled primer. The microarray may then processed by direct detection of the biotin-containing transcripts using, e.g., Streptavidin-Alexa647 conjugate, and scanned utilizing conventional scanning methods. Images intensities of each spot on the array are proportional to the abundance of the corresponding miRNA in the patient sample.

The use of an array has several advantages for miRNA expression detection. First, global expression of several hundred genes can be identified in a same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 μg of total RNA. The relatively limited number of miRNAs (a few hundred per species) allows construction of a common microarray comprising several species, with distinct oligonucleotide probes for each. Such a tool would allow for analysis of trans-species expression for each known miRNA under various conditions.

In addition to use for quantitative expression level assays of specific miRNAs, a microchip containing miRNA-specific probe oligonucleotides corresponding to a substantial portion of genomic miRNA's, preferably all genomic miRNA's, may be employed to carry out miRNA gene expression profiling, for analysis of miRNA expression patterns. Distinct miRNA signatures may be associated with established disease markers (i.e., for example, the $P2X_7$ gene and/or gene products), or directly with a disease state (i.e., for example, uterine cancer). As described hereinafter, human uterine cancer samples are associated with reductions of $P2X_7$ mRNA expression. As further described, elevated miRNA signatures are associated with prognostic markers of uterine cancer progression including, but not limited to, miRNA-150 and/or miRNA-186 expression. Therefore, miRNA gene expression profiles can be used for diagnosing the disease state of a cancer, such as whether a cancer is malignant or benign, based on whether or not a given profile is representative of a cancer that is associated with one or more established adverse prognostic markers.

According to an expression profiling method in one embodiment, total RNA from a sample from a subject suspected of having a cancer is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, i.e., noncancerous, control sample. An alteration in the signal is indicative of the presence of the cancer in the subject.

miRNAs may also be detected using various techniques involving coincidence binding of one or more probes. These techniques include, but are not limited to, dual labeled probes, fluorescence resonance energy transfer, primer extension analysis, or universal nucleic acid hybridizations. These techniques have demonstrated that miRNAs levels may be reduced in various forms of cancers. Neely et al., "Single Molecule MIRNA-Based Disease Diagnostic Methods" United States Patent Application Publication No. 2006/0292616 (herein incorporated by reference in its entirety).

EXPERIMENTAL

Example 1

Preparation of Uterine Cell Cultures

Discarded human uterine tissues from women undergoing hysterectomy for indications unrelated to the present study were obtained according to Institutional Review Board protocols 12-03-50 and 03-90-300 from the Human Tissue Procurement Facility of University Hospitals of Cleveland and the Comprehensive Cancer Center Tissue Procurement Core Facility (Case Western Reserve University, Cleveland, Ohio) and from the Cooperative Human Tissue Network (National Cancer Institute, Bethesda, Md.) through the Human Tissue Resource Network (Department of Pathology, Ohio State University, Columbus, Ohio). Tissues were collected over a period of 6 months based on availability.

On removal, uterine specimens were delivered to the Department of Pathology at University Hospitals of Cleveland or at the Ohio State University where the bulk of the tissue was used to establish the histologic diagnosis. Tissues selected by the pathologists for the purpose of the present study were snap frozen in liquid nitrogen, shipped on dry ice, and stored at −80° C. until assayed. Some tissues were fixed and embedded in paraffin according to standard procedures. Tissue processing for standard RNA and protein assays were also performed. Feng et al., "A truncated $P2X_7$ receptor variant ($P2X_{7-j}$) endogenously expressed in cervical cancer cells antagonizes the full-length $P2X_7$ receptor through hetero-oligomerization. *J Biol Chem* 281:17228-17237 (2006).

Tissues were obtained from a total of 72 women ages 25 to 75: Histologically Normal—15 endometrial, 3 endocervical, and 24 ectocervical tissues; Histologically Cancerous—29 endometrial cancers (28 endometrioid adenocarcinomas and 1 mixed adenomatous-mullerian cancer), 6 endocervical cancers (all adenocarcinomas), and 10 ectocervical cancers (all squamous cell carcinomas). Normal and cancer tissues were retrieved from uterine specimens of 15 women: 10 endometrial, 3 endocervical, and 2 ectocervical. The histologic diagnoses were assigned by the Departments of Pathology at University Hospitals of Cleveland or at the Ohio State University.

Cell culture techniques of normal human keratinocytes and the transformed cervical cancer cell line CaSki and the method of doxycyline-inducible expression of $P2X_7$ or P2X7-j in Madin-Darby canine kidney cells were followed as previously described. Gorodeski et al., "Human uterine cervical epithelial cells grown on permeable support—a new model for the study of differentiation and transepithelial transport" *Differentiation* 56:107-118 (1994). Gorodeski et al., "Characterization of paracellular permeability in cultured human cervical epithelium: regulation by extracellular ATP" *J Soc Gynecol Investig* 1:225-233 (1994); and Feng et al., "A truncated $P2X_7$ receptor variant ($P2X_{7-j}$) endogenously expressed in cervical cancer cells antagonizes the full-length P2X7 receptor through hetero-oligomerization. *J Biol Chem* 281:17228-17237 (2006).

Example 2

$P2X_7$ Gene Polymerase Chain Reaction Amplification

Quantitative PCR assays, including specific primers and conditions for amplification of the human full-length $P2X_7$ gene (Genbank Y09561), the truncated variant $P2X_{7-j}$ (Genbank DQ399293), as well as the constitutive glyceraldehyde-3-phosphate dehydrogenase, were performed as previously described. Feng et al., "A truncated $P2X_7$ receptor variant ($P2X_{7-j}$) endogenously expressed in cervical cancer cells antagonizes the full-length P2X7 receptor through hetero-oligomerization. *J Biol Chem* 281:17228-17237 (2006). Quantitative PCR results were calculated using the comparative threshold cycle (Ct) method of relative quantitation (RQ). Verification of reverse transcription was done by sequencing the PCR products using the above antisense primers.

For the full-length $P2X_7$ fragment, the conjunction sequences of exon 8 (bold letters) and exon 9 (italics) were confirmed as follows:

(SEQ ID NO: 7)
CCTTGTACCCTGGCTACAACTTCAGA*TACGCCAAGTACTACAAGGAAA* →
(856 bp).

For the truncated P2X7-j fragment, the conjunction sequences of exon 7 (bold letters) and exon 9 (italics) were confirmed as follows:

(SEQ ID NO: 8)
TTCAGATGTGGCAATTCAG*ATACGCCAAGTACTACAAGGGAAA* →
(726 bp).

Full-length $P2X_7$ cDNA template primers: (synthesized by Invitrogen, Carlsbad, Calif.) were:
Sense Strands (SEQ ID NO: 9)
(T7)-5-TGTAATACGACTCACTATAGGGCAATTCAGGGCGGAATAATGG GCAT;
and (SEQ ID NO: 10)
3-AGGGTACAAGGACACGTTGG, Antisense Strands (SEQ ID NO: 11)
5-CAATTCAGGGCGGAATAATG,
and (SEQ ID NO: 12)
(T7)-3-TGTAATACGACTCACTATAGGGTAGCCAGGGTAGAAGGACACG

TTGG.

The probes were synthesized by using 100 ng PCR fragments plus 2 AL DIG® labeling mix (Roche, Indianapolis, Ind.), 2 µL transcription buffer, 40 units of T7 polymerase (Roche), and $H_2O$ in a total volume of 20 µL. The mixture was incubated at 37° C. overnight, and the reaction was stopped by adding 0.8 µL of 0.5 mol/L EDTA. For ethanol precipitation, 2.5 µL of 4 mol/L lithium chloride plus 75 µl, prechilled (−20° C.) ethanol were added to the mixture followed by incubation at −80° C. for 2 hours and recentrifugation at 13,000×g for 5 minutes at 4° C. The pellet was dried, dissolved in 50 µL diethyl pyrocarbonate water, and stored at −80° C.

Tissue slices on slides were deparaffinized, rehydrated, and postfixed with 4% paraformaldehyde. After treatment with 0.04 N HCl for 20 minutes at room temperature, tissues were digested with 20 µg/mL proteinase K for 20 minutes at 37° C. Cultured cells were plated on polylysine-coated coverslips and grown in culture medium to subconfluence. After fixation with 4% paraformaldehyde/PBS for 15 minutes at room temperature, cells were washed with PBS containing 0.1% active diethyl pyrocarbonate. The cells were permeabilized with 0.1% Triton X-100/PBS/diethyl pyrocarbonate for 5 minutes and equilibrate with 5×SSC/diethyl pyrocarbonate for 15 minutes. Specimens (tissues or cells) were prehybridized for 2 hours at 58° C. in hybridization mix containing 5×SSC/50% formamide/40 µg/mL salmon sperm. DNA and hybridized at 58° C. overnight with 150 ng/µL sense or antisenseprobes for the full-length P2X$_7$ in hybridization mix solution. Following the incubation, specimens were washed in 2×SSC for 15 minutes at room temperature, then in the same buffer for 50 minutes at 65° C., and in 0.1×SSC for 1 hour at 65° C. and equilibrated with TN buffer containing 100 mmol/L Tris and 150 mmol/L NaCl (pH 7.5). Specimens were incubated with alkaline phosphatase—conjugated anti-digoxigenin antibody (1:1,000; Roche) in blocking solution for 2 hours at room temperature. Excess antibody was removed by two 15-minute washes in washing buffer and once by washing with detection buffer (Roche).

Color development was done at room temperature in BM Purple® alkaline phosphatase substrate (Roche) for 20 minutes in the dark, and staining was stopped with detection buffer. For cell cultures, nuclei were counterstained with methyl green or fast red and slides were dried with ethanol and mounted with VectaMount® (Vector Laboratories, Burlingame, Calif.). Straining was evaluated using Nikon Eclipse 80i® microscope (Nikon, Melville, N.Y.).

Example 3

P2X$_2$ Western Blots

Western blots, immunostaining and densitometry were done as previously described. Feng et al., "ATP ligation stimulates GRK-3-mediated phosphorylation and β-arrestin-2- and dynamin-dependent internalization of the P2X$_7$-receptor" *Am J Physiol* 288:C1342-C1356 (2005). Aliquots of postnuclear supernatants of cell lysates were normalized to 15 µg protein, separated in SDS-PAGE, and blotted by Western analysis.

P2X$_7$ receptor polypeptides (P2X$_7$ and P2X$_{7-j}$) were visualized using rabbit polyclonal anti-P2X$_7$ receptor in the absence or presence of its antigen peptide (Alomone Laboratories, Jerusalem, Israel). The anti-tubulin and anti-E-cadherin antibodies as well as secondary antibodies were previously described. Wang et al., "EGF facilitates epinephrine inhibition of P2X$_7$-receptor mediated pore formation and apoptosis: a novel signaling network" *Endocrinology* 146: 164-174 (2005); Feng et al., "ATP ligation stimulates GRK-3-mediated phosphorylation and h-arrestin-2- and dynamin-dependent internalization of the P2×7-receptor" *Am J Physiol* 288:C1342-1356 (2005); Zeng et al., "Estrogen abrogates transcervical tight junctional resistance by acceleration of occludin modulation" *J Clin Endocrinol Metab* 89:5145-5155 (2004); and Zhu et al., "Changes in tight junctional resistance of the cervical epithelium are associated with modulation of content and phosphorylation of occludin 65-kilodalton and 50-kilodalton forms" *Endocrinology* 147: 977-989 (2006).

All chemicals, unless specified otherwise, were obtained from Sigma Chemical (St. Louis, Mo.). Data were tabulated in contingency tables, and significance of differences between groups was estimated by $\chi^2$ test.

Example 4

Enhanced Degradation of 3'UTR-P2X$_7$ in Cancer Epithelial Cells

Primers for the full-length 3' untranslated region (3'UTR) of human P2X$_7$ gene (Genebank NM 002562) were as follows. For fragment one, Xba I forward primer: TTT TT TCT AGA AGC CAG GCA CCG TGG CTC ACG TCT GTA A (SEQ ID NO: 13); reverse primer: AGC CAG GAT GAA AAG GGT TT (SEQ ID NO: 14); For fragment two, forward primer: CTG TCC CCA GGA AGT TGT GT (SEQ ID NO: 15); Xba I reverse primer: TTT TT TCT AGA TTT TTT ITT TTT TTT GAG ATG GAG TCT CGC TCT GTC ACC CAG C (SEQ ID NO: 16): The corresponding cDNAs were synthesized by reverse transcription using human keratinocyte RNA with Oligo dT. Lewis et al., "Conserved seed pairing, often flanked by adenosines, indicates that thousands of human genes are microRNA targets" *Cell* 120:15-20 (2005). The two PCR fragments were digested with Xba I and Stu I and ligated together into pGL3 promoter Luciferase Reporter vector (SV-40 promoter, Promega, Madison, Wis.) containing Xba I-5' and Xba I-3' sites after digestion by Xba I using Rapid Ligation Kit (Roche, Indianapolis, Ind.) obtaining a PCR product of 1272 bp. The construct was confirmed for structure and orientation by sequencing.

Control plasmids (luciferase, 5010 bp) or test plasmids (P2X$_7$-3'UTR-luciferase, 6282 bp) were transfected into hEVEC or HeLa cells. Cells were plated in the evening before transfection in 6-well plates at a density of 2×10$^5$ cells per well, resulting in subconfluent cultures. After 14 hrs of incubation the culture medium was replaced with fresh medium plus 100 µl serum free medium (per well) containing 2.5 µl Fugene 6 (Roche) and 750 ng DNA of the control or test vectors. After 48 hrs of transfection-incubation cells were shifted to fresh medium lacking added plasmids and at times 0, 3 his, and 6 hrs cells were harvested in RNA lysis buffer (Qiagen RNeasy Mini Kit®). Total RNA was extracted and luciferase mRNA levels were determined by the one-step Real-time RT-PCR as described above, using the following sets of primers: 5'-TAT GAA GAG ATA CGC CCT GGT T-3' (SEQ ID NO: 17) and 3'-GCC CAT ATC GTT TCA TAG CTT C-5' (SEQ ID NO: 18). qPCR utilized 600 ng RNA/sample (50° C./30 min, 95° C./15 min, 60° C./1 min, 40 cycle). mRNA steady-state levels in cells transfected with the 3'UTR-P2X$_7$-luciferase vector were normalized to 0 hr results in cells transfected with the control vector.

Experiments were conducted using human ectocervical-vaginal epithelial (hEVEC) cells (normal) and HeLa (cancer) uterine cervical epithelial cells. A cDNA corresponding to the 3'UTR region of the human P2X$_7$ gene was ligated upstream of SV40 promoter/luciferase reporter vector, and the construct cDNA was transfected into hEVEC or HeLa cells. Control experiments included cells transfected with the luciferase reporter vector only.

Figure 1:
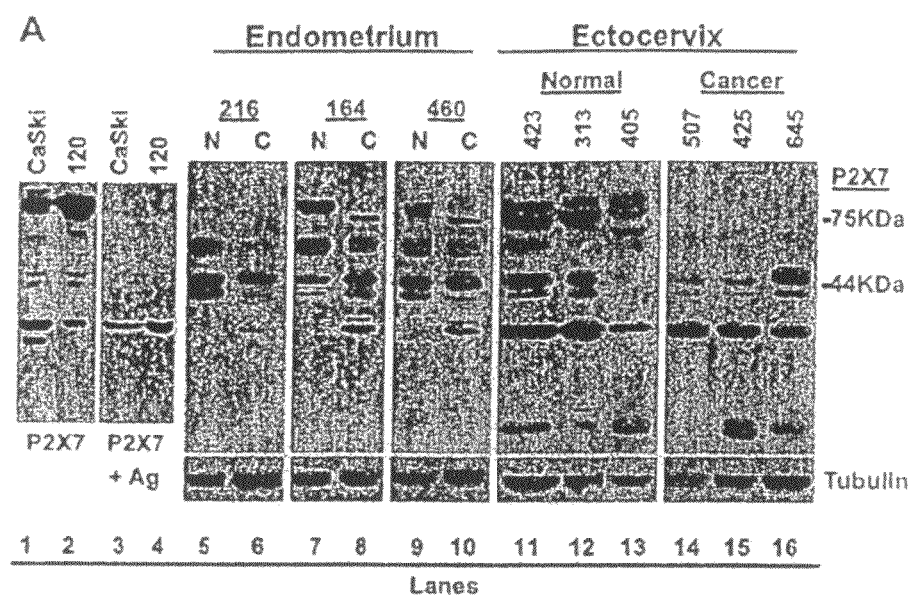
FIG. 1A presents exemplary Western blot data using the anti-$P2X_7$ antibody in the absence (lanes 1, 2, and 5-16) or presence (lanes 3 and 4) of the $P2X_7$ antigen (+Ag). Numbers at the top of the figures are patient identifier codes. Case 120 was normal endometrium. In cases 216, 164, and 460, endometrial normal (N) and cancer (C) tissues were obtained from the same patient. Where indicated, gels were reprobed with anti-tubulin antibody (Tubulin). Coincubation of the anti-$P2X_7$ antibody with the $P2X_7$ antigen blocked expression of the 65 to 85-kDa ($P2X_7$) and the 42 to 45-kDa ($P2X_{7-j}$) immunoreactivities.
FIG. 1B presents exemplary data showing immunostaining of normal endometrium with anti-$P2X_7$ antibody in the presence (+Ag) or absence of the $P2X_7$ antigen. The experiment was repeated three times with similar trends.
FIG. 1C presents exemplary data showing mRNA assayed by real-time reverse transcription-PCR using normal and cancer endometrial tissues obtained from patients with the designated codes. Cross-hatched columns: $P2X_7$. Open columns: $P2X_{7-j}$.
Figure 1:
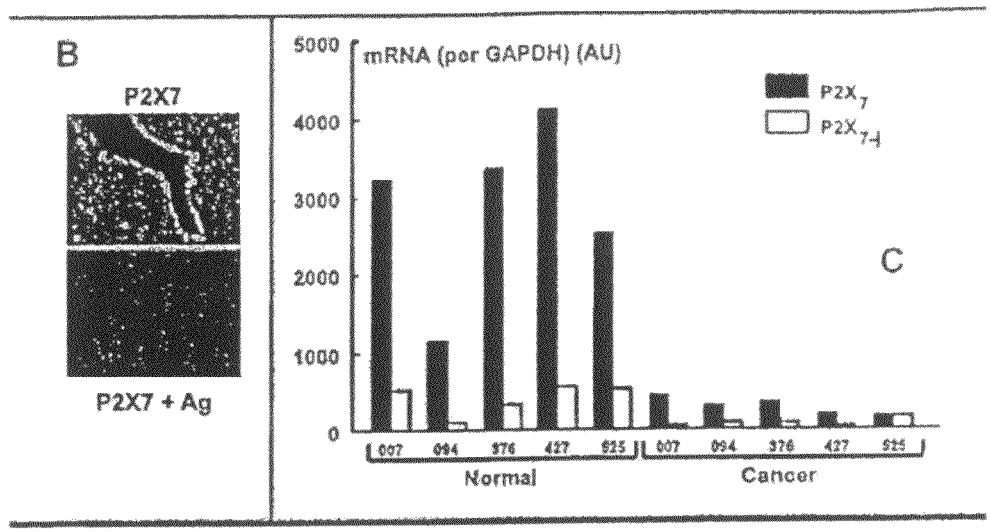

In hEVEC, or HeLa cells, transfected with the control luciferase reporter vector, steady-state levels of luciferase mRNA did not change significantly over a 6 hours incubation period FIG. 6A. In hEVEC cells transfected with the 3'UTR-P2X$_7$-luciferase vector, steady-state levels of luciferase mRNA also did not change significantly over a 6 hours incubation period FIG. 1B. In contrast, in HeLa cells transfected with the 3'UTR-P2X$_7$-luciferase vector, steady-state levels of the luciferase mRNA decreased significantly. FIG. 1B.

These results show a greater degree of degradation of overexpressed 3'UTR-P2X$_7$ in the cancer epithelial cells than in the normal epithelial cells, suggesting that regions at the 3'UTR-P2X$_7$ gene contain instability sites, and that the faster degradation of the P2X7 mRNA in cancer cells is the result of activation of instability domains located at the 3'UTR.

Example 5

Differential miRNA Stability in Normal and Cancer Cells

Luciferase containing 3'UTR-P2X$_7$ vectors comprising a complementary segment for either miR-186 or miR-150 were constructed in accordance with Example 4. In cells transfected with a complementary segment for miR-186 (SEQ ID NO: 20), decreases in luciferase mRNA were observed both in hEVEC and HeLa cells, but the decrease in HeLa cells occurred earlier and was greater than in hEVEC cells. FIG. 7A. In hEVEC cells transfected with a complementary segment for miR-150 (SEQ ID NO: 21) luciferase mRNA increased over the 6 firs incubation period. FIG. 7B. In contrast, in HeLa cells transfected with a complementary segment for miR-150, luciferase mRNA decreased after 6 hrs. FIG. 7B.

The potential role of miR-186 and miR-150 in regulation of P2X$_7$ mRNA was assessed by testing the stability of short segments of a 3'UTR-P2X$_7$ containing complementary miRNA segments. These wild-type segments (WT) were compared to mutated (M) sequences (compare underlined portions between the sequences below):

```
miR-186 WT:
GAGAACTAAAGGTGGCCACAAATTCTTTGACACT    (SEQ ID NO: 22)

miR-186 M:
GAGAACTAAAGGTGGCCACAAATAGATTGACACT    (SEQ ID NO: 23)

miR-150 WT:
CACCTGTAATCCCAGGACTTTGGGAGA           (SEQ ID NO: 24)

miR-150 M:
CACCTGTAATCCCAGCACTTTCCCAGA           (SEQ ID NO: 25)
```

The vectors comprising SEQ ID NOs: 22-25 were transfected into hEVEC and/or Hela cells and overexpressed in accordance with Example 4. The results of these studies are as follows (See, FIG. 8):

a. No significance changes in luciferase mRNA were observed in hEVEC cells transfected with luciferase vector containing a miR-186-WT complementary segment (FIG. 5A ○).

b. Luciferase mRNA increased in hEVEC cells transfected with luciferase vector containing a miR-186-M complementary segment (FIG. 5A △).

c. Luciferase mRNA decreased in HeLa cells transfected with luciferase vectors containing either a miR-186-WT complementary segment (FIG. 5B ●) or a miR-186-M complementary segment (FIG. 5B ▲).

d. No significance changes in luciferase mRNA were observed in hEVEC cells transfected with luciferase vectors containing either the miR-150-WT complementary segment (FIG. 5C ⊙) or a miR-186-M (FIG. 5C A) complementary segment.

e. Luciferase mRNA decreased in HeLa cells transfected with luciferase vectors containing either a miR-150-WT complementary segment (FIG. 5D ●) or a miR-150-M complementary segment (FIG. 5D ▲), but the decrease was smaller in cells transfected with the miR-150-M complementary segment than with the miR-150-WT complementary segment (FIG. 5D).

These data suggest that miR-186 and/or miR-150 regulate the stability of the P2X$_7$ mRNA. An overall comparasion of equivalent data can be seen in FIG. 9.

Example 6 miRNA as a Biomarker for Uterine Cancer

This experiment outlines a method to show that uterine cancer cells have higher levels of miR-150 and/or miR-186 than corresponding normal uterine cells.

Tissue samples will be collected in accordance with Example I. miRNA levels will be compared between non-cancerous uterine tissues and cancerous uterine tissues. Specifically, the experiment will compare miRNA-186 and miRNA-150. The results will show that cancerous uterine cells contain higher levels of both miRNA-186 and miRNA-150 than the non-cancerous uterine cells.

We claim:

1. A composition comprising a pathophysiological microRNA biomarker oligonucleotide probe and a reverse transcribed $P2X_7$ mRNA, said mRNA being derived from a uterine cell, wherein said biomarker oligonucleotide probe is hybridized to said reverse transcribed $P2X_7$ mRNA 3' UTR.

2. The composition of claim 1, wherein said reverse transcribed $P2X_7$ mRNA 3' UTR comprises a label.

3. The composition of claim 1, wherein said uterine cell is a normal uterine cell.

4. The composition of claim 1, wherein said biomarker probe oligonucleotide comprises miR-150.

5. The composition of claim 1, wherein said biomarker probe oligonucleotide comprises miR-186.

6. The composition of claim 1, wherein said uterine cell is a cancer uterine cell.

7. The composition of claim 2, wherein said label is biotin.

8. The composition of claim 5, wherein said miR-186 hybridizes to said reverse transcribed P2X7 mRNA 3' UTR at an AATTCTTTG sequence.

9. The composition of claim 4, wherein said miR-150 hybridizes to said reverse transcribed P2X7 mRNA 3' UTR at an TTGGGAGA sequence.

* * * * *